US010545041B2

United States Patent
Ajay et al.

(10) Patent No.: US 10,545,041 B2
(45) Date of Patent: Jan. 28, 2020

(54) ADDRESSABILITY IN PARTICLE DETECTION

(71) Applicant: Xtralis Technologies, Ltd., Nassau (BS)

(72) Inventors: Kemal Ajay, Mount Waverley (AU); Ron Knox, Mount Eliza (AU); Brian Alexander, Wantirna (AU); Karl Boettger, Mount Waverley (AU); Rajiv Kumar Singh, Glen Waverley (AU); Thor North, Melbourne (AU); Stephen James Pattinson, Surrey Hills (AU); Peter Massingberd-Mundy, Leighton Buzzard (GB)

(73) Assignee: Xtralis Technologies, Ltd., Nassau (BS)

( * ) Notice: Subject to any disclaimer, the term of this patent is extended or adjusted under 35 U.S.C. 154(b) by 0 days.

(21) Appl. No.: 14/433,201

(22) PCT Filed: Oct. 16, 2013

(86) PCT No.: PCT/AU2013/001201
§ 371 (c)(1),
(2) Date: Apr. 2, 2015

(87) PCT Pub. No.: WO2014/059479
PCT Pub. Date: Apr. 24, 2014

(65) Prior Publication Data
US 2015/0253165 A1 Sep. 10, 2015

(30) Foreign Application Priority Data

Oct. 16, 2012 (AU) ................................. 2012904516
Nov. 2, 2012 (AU) ................................. 2012904854

(Continued)

(51) Int. Cl.
*G01F 1/66* (2006.01)
*G01N 15/14* (2006.01)

(52) U.S. Cl.
CPC ........... *G01F 1/66* (2013.01); *G01N 15/1434* (2013.01)

(58) Field of Classification Search
CPC ........ G01F 1/66; G01N 15/1434; G01N 1/24; G01N 2001/245; G01N 15/06; G01N 2015/0046; G08B 17/10; G08B 17/113
See application file for complete search history.

(56) References Cited

U.S. PATENT DOCUMENTS 5,000,052 A * 3/1991 Sipin .................... G01N 1/2202
73/863.03
5,103,212 A 4/1992 Notarianni et al.
(Continued)

FOREIGN PATENT DOCUMENTS

AU 2011202538 A1 6/2011
EP 1811478 A1 7/2007
(Continued)

*Primary Examiner* — Xin Y Zhong
(74) *Attorney, Agent, or Firm* — Brooks, Cameron & Huebsch, PLLC

(57) ABSTRACT

A method of determining at least one point of entry of smoke into a smoke detection system, the system having a sampling pipe network including at least one sampling pipe and a plurality of sampling inlets through which an air sample can enter the at least one sampling pipe of the smoke detection system for analysis by a particle detector, said method including: determining a volume of sample air that has passed through at least part of the smoke detection system since a predetermined event or a value corresponding to said volume; and determining through which sampling inlet of the plurality of sampling inlets the smoke entered the smoke detection system based, at least in part, on the determined (Continued)

volume or value. Systems for implementing such a method and related methods are also described.

24 Claims, 25 Drawing Sheets

(30) Foreign Application Priority Data

Jan. 21, 2013 (AU) ................................ 2013200353
Jun. 7, 2013 (AU) ................................ 2013902076
Jul. 11, 2013 (AU) ................................ 2013902570

(56) References Cited

U.S. PATENT DOCUMENTS

| 5,708,218 | A | 1/1998 | Jax | |
|---|---|---|---|---|
| 7,375,642 | B2 * | 5/2008 | Siemens | ................ G08B 17/10 340/628 |
| 8,035,527 | B2 | 10/2011 | Powell | |
| 8,065,922 | B2 | 11/2011 | Ajay et al. | |
| 8,224,621 | B2 | 7/2012 | Ajay et al. | |
| 2007/0008157 | A1 * | 1/2007 | Siemens | ................ G08B 17/10 340/577 |
| 2007/0084286 | A1 * | 4/2007 | Ajay | ....................... G01F 1/667 73/597 |
| 2007/0168140 | A1 | 7/2007 | Knox | |
| 2010/0171625 | A1 | 7/2010 | Calio | |
| 2010/0194575 | A1 | 8/2010 | Rodriguez | |
| 2012/0079871 | A1 | 4/2012 | Williamson | |
| 2012/0319853 | A1 * | 12/2012 | Goulet | ................ G08B 17/113 340/632 |

FOREIGN PATENT DOCUMENTS

| FR | 2 276 577 | A1 | 1/1976 |
|---|---|---|---|
| JP | S53-146687 | A | 12/1978 |
| JP | S55-131379 | A | 10/1980 |
| JP | H08-184536 | A | 7/1996 |
| TW | 201105946 | A1 | 2/2011 |
| WO | 2004/102499 | A1 | 11/2004 |
| WO | 2014/059479 | A1 | 4/2014 |

* cited by examiner

| Location | Grey code address | Smoke detected? | | | |
|---|---|---|---|---|---|
| | | Pipe 1 | Pipe 2 | Pipe 3 | Pipe 4 |
| 1 | 0001 | No | No | No | Yes |
| 2 | 0011 | No | No | Yes | Yes |
| 3 | 0010 | No | No | Yes | No |
| 4 | 0110 | No | Yes | Yes | No |
| 5 | 0111 | No | Yes | Yes | Yes |
| 6 | 0101 | No | Yes | No | Yes |
| 7 | 0100 | No | Yes | No | No |
| 8 | 1100 | Yes | Yes | No | No |
| 9 | 1101 | Yes | Yes | No | Yes |
| 10 | 1111 | Yes | Yes | Yes | Yes |
| 11 | 1110 | Yes | Yes | Yes | No |
| 12 | 1010 | Yes | No | Yes | No |
| 13 | 1011 | Yes | No | Yes | Yes |
| 14 | 1001 | Yes | No | No | Yes |
| 15 | 1000 | Yes | No | No | No |

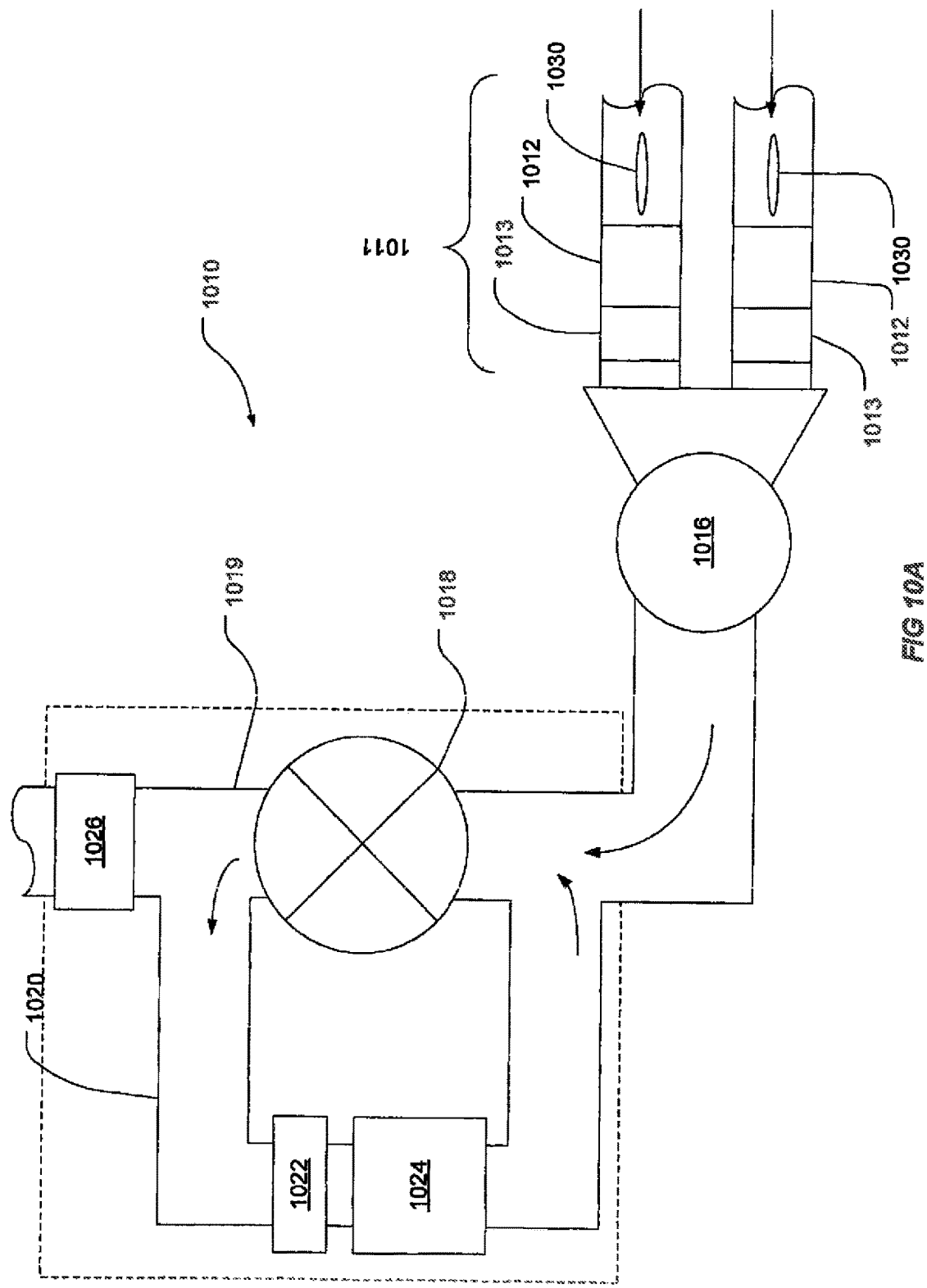

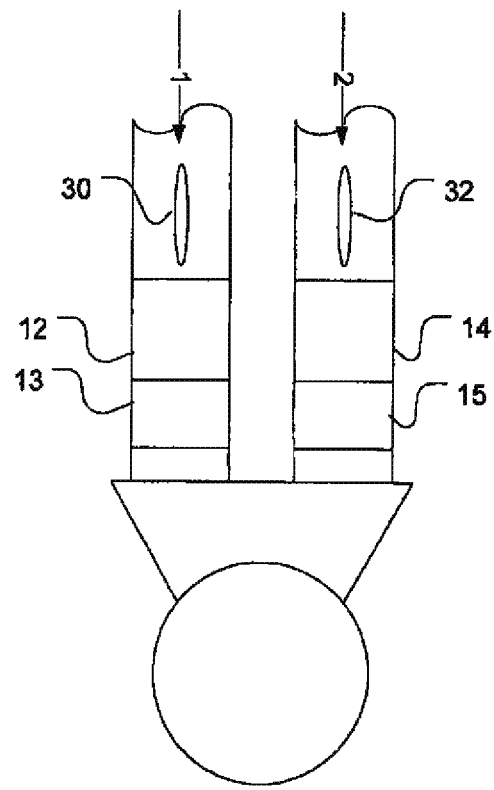
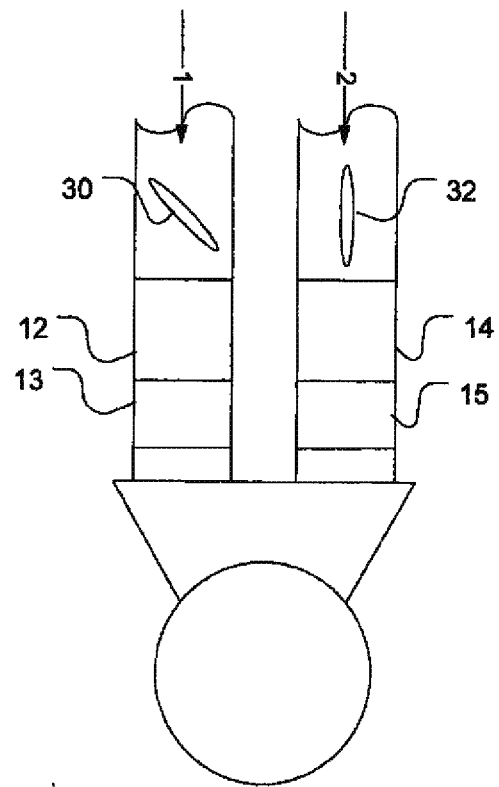
FIG 10B
FIG 10C
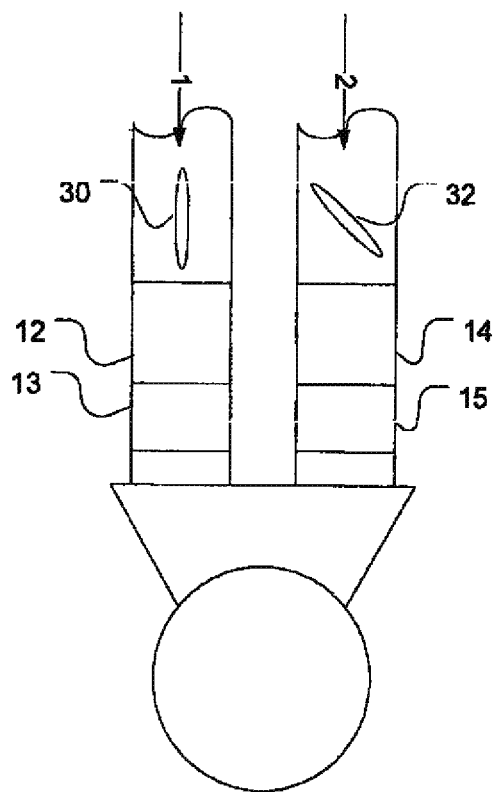
FIG 10D

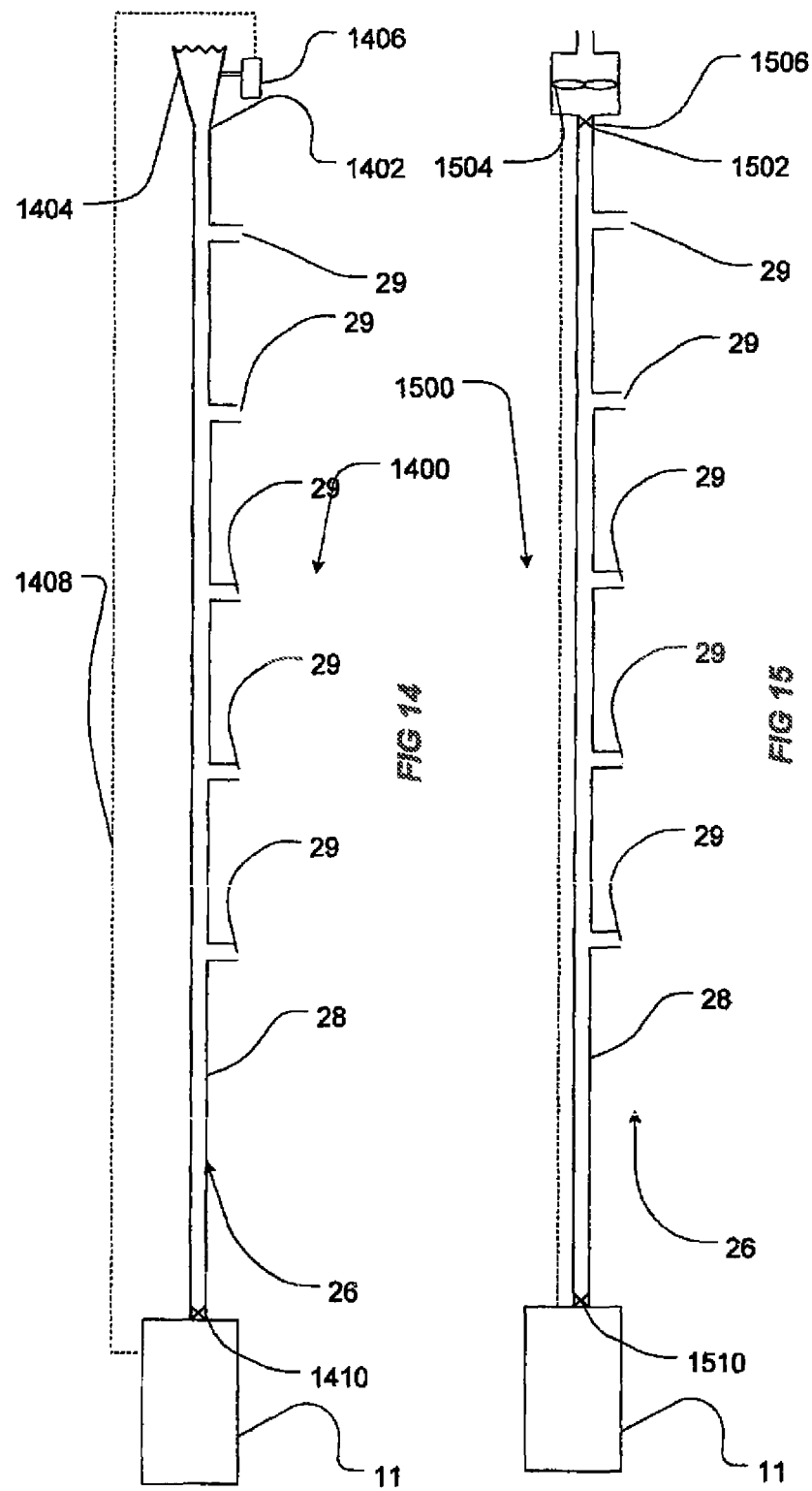

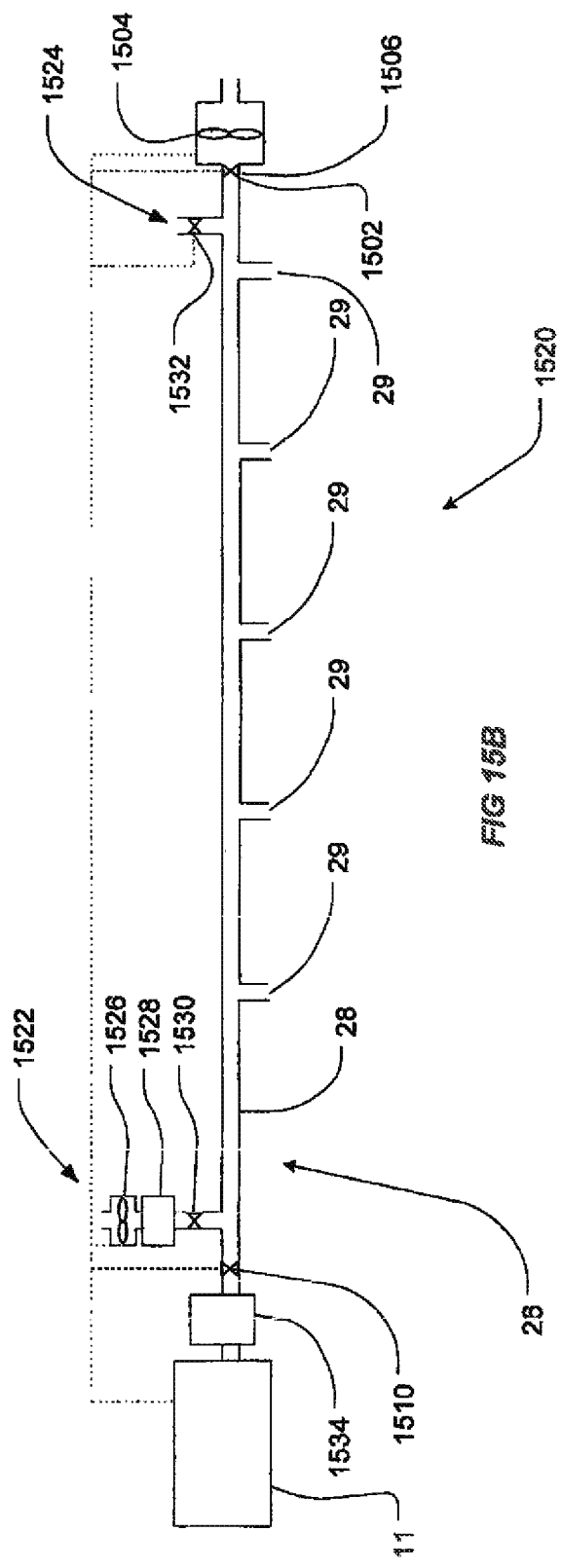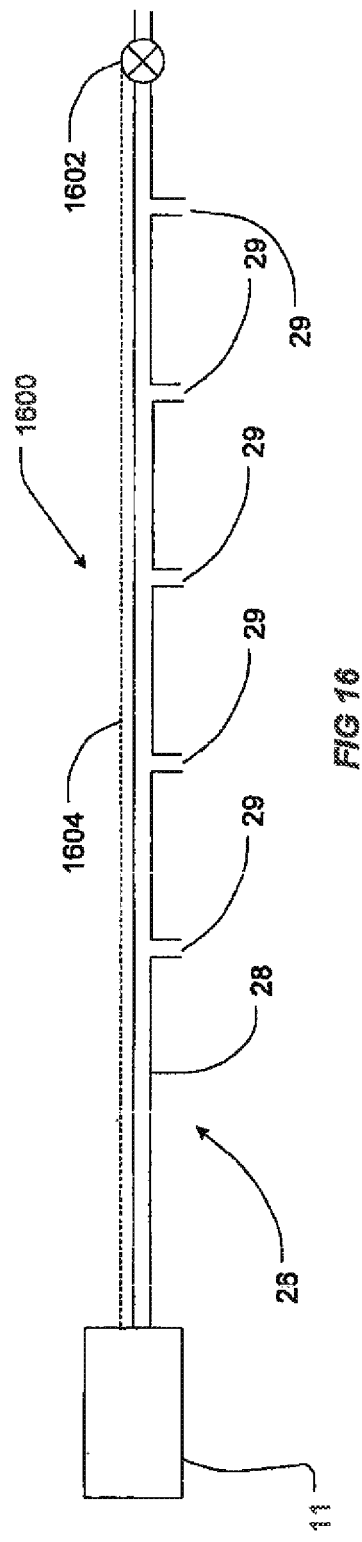
FIG 15B
FIG 16

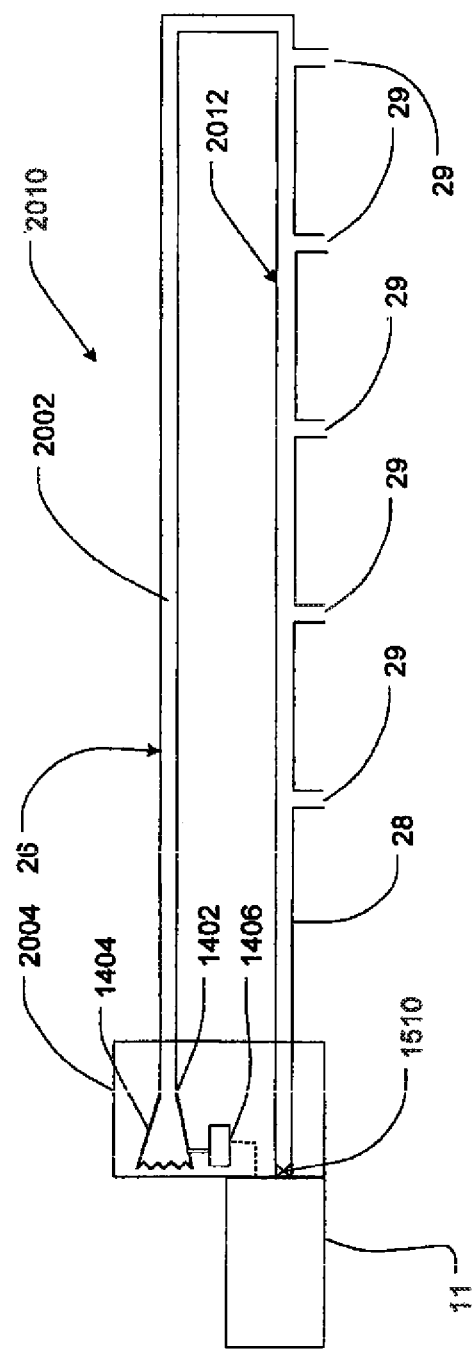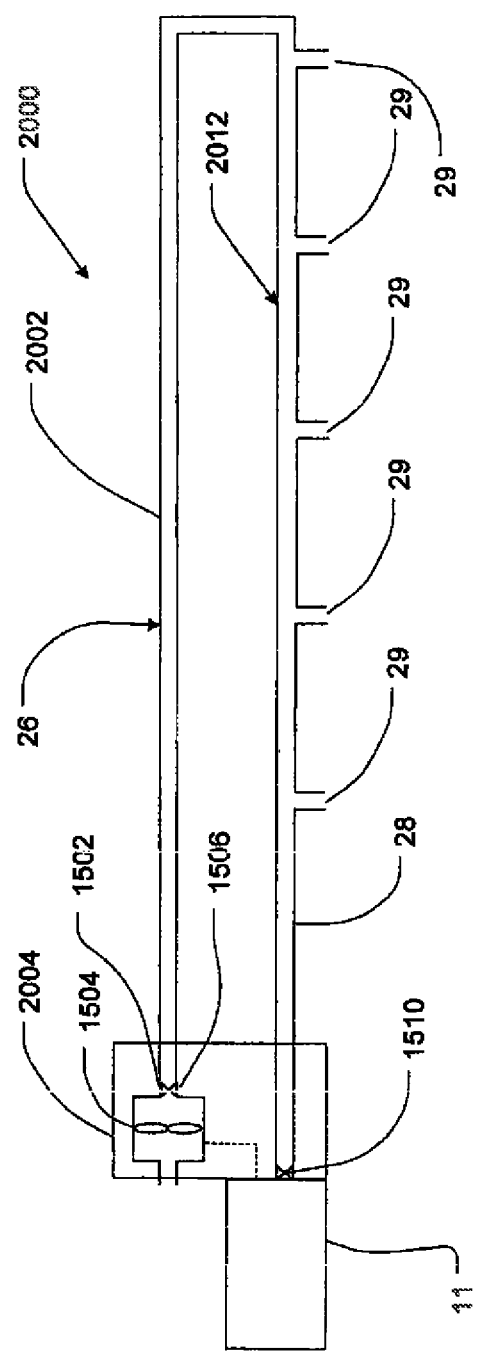

ADDRESSABILITY IN PARTICLE DETECTION

RELATED APPLICATIONS

This application claims the benefit of Australian provisional patent applications: 2012904516, filed 16 Oct. 2012; 2012904854, filed 2 Nov. 2012; 2013902076, filed 7 Jun. 2013; and 2013902570 filed 11 Jul. 2013; and Australian complete patent application 2013200353, filed 21 Jan. 2013, each of which are incorporated herein by reference for all purposes.

BACKGROUND OF THE INVENTION

1. Field of the Invention

The present invention relates to particle detection. For illustrative purposes only, the preferred embodiment of the present invention will be described in relation to a smoke detection system, but the invention should not be considered to be limited to that exemplary use.

2. Discussion of the Related Art

Air sampling or aspirated smoke detection systems operate by drawing air samples through a sampling network, to a central high sensitivity particle detector. The sampling network typically includes one or more sample pipes with a number of air sample inlets in the form of sampling holes or sampling points located along the length of the pipe(s). In such an arrangement, a single detector may be fed with air originating from many distinct geographical locations at which the air sample inlets are located. Thus a single such detector can monitor for the presence of smoke at many distinct locations simultaneously.

One recognised difficulty with air sampling systems as described above is that they do not identify through which air inlet smoke enters the system. If the air inlet is known, the geographical location of the source of the smoke may be inferred. This allows investigation of the likely site of the fire including allowing a person to be directed to the location of the smoke, so that they may investigate and possibly intervene and prevent further growth of the fire, or shut down equipment in the area. Alternatively, an appropriate fire suppression system may be deployed in a localised way, limiting damage caused by the system, as well as expense.

There have been attempts to provide air sampling particle detection systems capable of determining the geographical location at which smoke is detected, for example Jax, 'Method and Device for locating accumulations of pollutants', U.S. Pat. No. 5,708,218 and Hekatron Vertriebs GmbH, 'Verfahren and Vorrichtung zur Erkennung eines Brandes', EP 1811478.

Each of these systems measures the elapsed time between two instants at which measurements are made to infer where along sampling pipe (i.e. through which sample inlet) the detected smoke entered the system. However, this inferential process is often unreliable.

The Jax system measures the elapsed time between detection of a first smoke level, and a second smoke level. The time between detection of a first, lower level of smoke, and a second, higher level of smoke indicates the distance along the collection line at which smoke entered the system. However, this process may be inaccurate. For example, systems employing this approach rely upon the actual level of smoke detected at the first point of entry remaining approximately constant for the period of time beginning from the point at which smoke is first detected until the contribution from the second point of entry can be reliably detected. More specifically, an increase in smoke level, such as that caused by a fire of growing size, may result in an inaccurate estimate of the geographical location from which air has been drawn.

In Hekatron, a first air-sampling detection unit detects the presence of smoke. Responsive to detection of smoke, a second air-sampling detection unit is engaged, the air sampling unit drawing air along the pipe network. The time elapsed between initial detection by the first air-sampling unit and detection by the second air-sampling unit is measured. Ideally, the time elapsed indicates the location from which smoke filled air has been drawn. To ensure accuracy, such a system requires the aspiration system to operate in a highly consistent manner, each time it is operated. However, this is difficult to achieve as various features influence the operation of the fall, e.g. degradation of the aspiration system over time and variations in operational and environmental conditions e.g. air density, or the constriction of sampling points by dirt over time, will change the airflow characteristics within the system, and make the inference of the smoke address based on elapsed time potentially unreliable.

In some schemes, airflow may be temporarily reversed, introducing clean air to the sampling network, before redrawing air for detection. The idea in such schemes is to flush substantially all smoke particles from the system, before redrawing air through the sampling network and measuring the delay before detecting smoke. In theory, a longer delay indicates that the particles entered the sampling network at a point farther from the detector. However, these schemes suffer a drawback in that during the phase that clean air is introduced to the sampling network, smoke particles within the monitored environment may be displaced in the area surrounding the air inlets, since clean air is being expelled from the inlets. When air is subsequently drawn through the system, there may be an additional delay before smoke particles are once again drawn into the inlet.

It is therefore an object of the present invention to provide a particle detection system that addresses at least some of the aforementioned disadvantages. An alternative object of the invention is to provide the public with a useful choice over known products.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In a first aspect of the present invention there is provided a method of determining at least one point of entry of smoke into a smoke detection system, the system having a sampling pipe network including at least one sampling pipe and a plurality of sampling inlets through which an air sample can enter the at least one sampling pipe of the smoke detection system for analysis by a particle detector. The method includes: determining a volume of sample air that has passed through at least part of the smoke detection system since a predetermined event or a value corresponding to said volume; and determining through which sampling inlet of the plurality of sampling inlets the smoke entered the smoke detection system based, at least in part, on the determined volume or value.

The predetermined event could be, for example, a smoke detection event; or a change in an air sample flow characteristic in the smoke detection system.

In some embodiments the method includes continuously determining a flow rate of the air sample passing through at least part of smoke detection system. Alternatively the method includes commencing determination of the volume of sample air or a related value upon the occurrence of the predetermined event.

The volume of the air sample that has passed through at least part of smoke detection network or a related value can be determined by accumulating a flow rate measurement over time. The rate of flow measurement is preferably a volumetric flow rate measurement. Most preferably the he flow rate measurement is determined using an ultrasonic flow sensor.

The step of determining a volume of sample air that has passed through at least part of the smoke detection system since a predetermined event or a value corresponding to said volume, can include determining any one of more of: a mass; a length; a pressure; a temperature, a second volume; or an accumulated count of volume-related events, or other parameter that that relates to a volume of sample air that has passed through at least part of the smoke detection system since the predetermined event.

The method can include collecting all or a proportion of the sample air that has passed through at least part of the smoke detection system since the predetermined event.

The method can further include changing an air sample flow characteristic in response to a first smoke detection event. For example, changing an air sample flow characteristic in the smoke detection system can include one or more of the following:
 opening a valve;
 closing a valve;
 changing a direction of an air sample flow in at least part of the smoke detection system;
 changing a rate of air sample flow in at least part of the smoke detection system;
 starting an aspiration system; and
 stopping an aspiration system.

In a second aspect of the present invention, there is provided an apparatus for determining at least one point of entry of smoke into a smoke detection system of the type having a particle detector in fluid communication with an air sampling network, the air sampling network having at least one sampling pipe and a plurality of sampling inlets through which an air sample can enter the at least one sampling pipe of the smoke detection system for analysis by the particle detector, and an aspirator for drawing the air sample through the air sampling network to the detector. The apparatus includes: means for determining a volume of sample air that has passed through at least part of the smoke detection system since a predetermined event or a value corresponding to said volume; and means for identifying at least one point of entry of particles into the sampling network based on the detected volume or value.

The apparatus preferably identifies one or more of said points of entry by reference to one or more corresponding sampling inlets through which smoke determined to have entered the system.

The means for determining a volume of sample that has passed through at least part of the particle detection system, or value related to said volume, preferably includes a flow sensor. Most preferably the flow sensor comprises an ultrasonic flow sensor.

The apparatus is preferably configured to perform a method in accordance with the first aspect of the present invention.

In a third aspect of the present invention, there is provided a smoke detector including a particle detection chamber to detect particles in an air sample, an inlet to receive an air sample from an air sampling network, said the sampling network having at least one sampling pipe and a plurality of sampling inlets through which a sample can enter the at least one sampling pipe for analysis by the particle detection chamber, and an aspirator for drawing the sample through the air sampling network to the detector, the detector further including a processor configured to: identify at least one point of entry of smoke into the sampling network based, at least in part, on a volume of sample air that has passed through at least part of the smoke detector or sampling network since a predetermined event, or a value corresponding to said volume.

The smoke detector can include a flow sensor, e.g. an ultrasonic flow sensor, configured to detect rate of flow of sample air passing through at least a part of the smoke detector.

The processor is preferably configured to cause the smoke detector to perform a method in accordance with the first aspect of the present invention.

Also disclosed herein is a method of determining the point of entry of particles into a particle detection system, said particle detection system including a particle detector and a sampling network in fluid communication with the particle detector, the sampling network including a plurality of inlets through which a fluid is drawn, the particle detection system further including means for drawing fluid through the sampling network to the detector. The method includes: comparing a first particle detection profile to a second particle detection profile; determining an offset between the particle detection profiles at which the profiles match to a predetermined degree; and, determining a location of entry of particles into the detection system on the basis of that offset.

In some embodiments, the offset is a time offset. In other embodiments, the offset is a volume offset.

In some embodiments, the comparison involves calculation of a cross-correlation between particle detection profiles.

In some embodiments, a maximum value of the calculated cross correlation is determined, and an offset between particle detection profiles corresponding to the maximum value is determined.

In some embodiments, the calculated cross correlation function is determined and compared to a predetermined value.

Preferably, the fluid is air, and the means for drawing fluid through the sampling network to the detector is an aspirator.

One embodiment includes determining that at least a first predetermined particle detection criteria has been met on the basis of a first particle detection profile being a comparison of the first and second particle detection particles.

The method can include continuously storing a first and/or second particle detection profile. Alternatively one of the profiles may be stored only after at least one predetermined criteria has been fulfilled.

The method can include changing an air flow characteristic in at least part of the particle detection system prior to beginning a comparison of the first and second particle detection profiles.

In one form the step of changing an air flow characteristic in the particle detection system includes one or more of the following:

opening a valve;
closing a valve;
changing a direction of an air flow in at least part of the particle detection system;
changing a rate of air flow in at least part of the particle detection system;
starting an aspiration system; and
stopping an aspiration system.

Further disclosed herein is an apparatus for determining the point of entry of particles into a particle detection system of the type having a particle detector in fluid communication with an air sampling network, the air sampling network having a plurality of inlets through which air may enter the air sampling network, and an aspirator for drawing air through the air sampling network to the detector, the apparatus including means for determining a volume of air passing through at least a part of the particle detection system, said apparatus including: means for receiving a signal representative of the volume of air passing through at least a part of the particle detection system; means for determining a location in the air sampling network at which air carrying particles entered the network on the basis of the determined volume.

Also disclosed herein is a device for determining the point of entry of particles into a particle detection system through one or more of a plurality of air inlets. The device includes means for determining a volume of air flowing through at least part of the particle detection system and means for determining a point of entry of the particles based upon the measured volume.

Preferably, the apparatus for determining the point of entry of particles into the particle detection system identifies the source of particles by reference to at least one inlet through which particles are likely to have entered.

Further preferably, the apparatus for determining the point of entry of particles into the detection system identifies the source of particles by providing an indication of the distance of along the sampling network at which particles entered the air sampling network.

Further disclosed herein is a method of determining the point of entry of particles into a particle detection system having a sampling pipe network with a plurality of sampling points through which particles can enter the particle detection system. The method includes, determining the volume of air passing through at least part of particle detection system and determining through which sampling hole of the plurality of sampling points the particles entered the particle detection system.

The method can include, detecting a first particle detection event and a second particle detection event, and measuring the volume of air passing through at least part of particle detection network between the particle detection events.

The method can include continuously measuring the volume of air passing through at least part of particle detection network. Alternatively the method can include activating the volume measurement upon the occurrence of a predetermined condition.

The volume of air passing through at least part of particle detection network is preferably measured by summing a rate of flow measurement over time. Preferably the rate of flow measurement is a volumetric flow rate measurement. Most preferably it is determined using an ultrasonic flow sensor.

Further disclosed herein is a particle detection system including a particle detector, a sampling network in fluid communication with the particle detector, and means for drawing fluid through the sampling network to the detector.

The sampling network includes a plurality of inlets, the inlets being arranged into a plurality of location groups. Each location group has an address defined by the presence or absence of an inlet connected to each of a plurality of sampling pipes. The particle detector is configured to draw air along each sampling pipe and in the event that smoke is detected, determine the address of the location group through which particles entered the detector based upon both the presence and absence of particles in each of the sampling pipes.

Also disclosed herein is a method of determining a single point of entry of particles into a particle detection system. The particle detection system includes at least one particle detector, a sampling network in fluid communication with a or the particle detector, and means for drawing fluid through the sampling network to a or the detector. The sampling network includes a plurality of sample communication paths along which a sample can be drawn and in which the presence of particles can be independently detected by at least one of the detectors, wherein each sample communication path includes at least one sample inlet. Each of said inlets further belongs to one of a plurality of location groups defined by the physical location of the inlet. The particle detection system being configured to determine whether particles are been detected on an air sample from each sample communication path. The method includes:
    determining a location group of inlets at which particles entered into the particle detection system uniquely on the basis of whether particles have or have not been detected on each sample communication path.

In one embodiment, the sampling network comprises a plurality of pipes that respectively correspond to a sample communication path, and the step of determining that particles have been detected at a location group comprises determining that particles have or have not been detected in fluid drawn through each of the plurality of pipes.

Further disclosed herein is an apparatus for determining the point of entry of particles into a particle detection system of the type having at least one particle detector in fluid communication with a sampling network, and aspiration means for drawing fluid through the sampling network to the or a particle detector, the sampling network including a plurality of sample communication paths in which particles can be separately detected. The sampling network includes a plurality of sample inlets, each inlet being a member of a location group at one of a plurality of physical locations; the apparatus further including means for determining a location at which particles are present on the basis of whether particles have or have not been detected on each sample communication path.

Also disclosed herein is a method in a particle detection system having:
    at least one particle detector, and
    a sampling system including a sampling pipe with a plurality of sampling inlets, said sampling system being arranged to convey a sample to be analysed from an environment surrounding the sampling inlet via the sampling pipe to the at least one particle detector;
    a flow inducer arranged to cause an air sample to flow in the sampling system to the at least one particle detector;
the method including:
    measuring a first particle concentration in a sample arriving form the sampling system;
    varying a sampling parameter at a subset of the sampling inlets;
    measuring a second particle concentration in a sample arriving form the sampling system;

measuring a particle concentration in a sample arriving form the sampling system; on the basis of the first and second particle concentrations and the varied sampling parameter.

The sampling parameter that is varied can be flow rate through the first subset of sampling inlets. The variation can be triggered by opening or closing valves or using a fan or other flow inducer to increase (or decrease) flow through the subset of sampling inlets. In this case the varied sampling parameter used to determine the measuring a particle concentration in a sample arriving form the sampling system can be a flow rate through the subset of sampling inlets.

In some embodiments the sampling parameter that is varied is the particle concentration drawn through the first subset of sampling inlets. The variation can be triggered by adjusting a filtering parameter applied to the first subset of sampling inlets, e.g. by interposing or removing a filter in the flow path of air entering through the sampling inlets. In this case the varied sampling parameter used to determine the measuring a particle concentration in a sample arriving form the sampling system can be a sample concentration the subset of sampling inlets.

In some embodiments the first subset of sampling inlets is the same as the second subset of sampling inlets. The first or second subsets if sampling inlets may include a plurality of inlets, or may be a single inlet.

Also disclosed herein is a method for detecting contaminant(s) in air samples from a plurality of air intake paths, the method including:
varying the flow balance between the multiple paths by increasing or partially reducing the flow in one or more of the plurality of air intake paths to create a plurality of different flow patterns;
measuring the contaminant level of the combined air intake paths for each of the plurality of different flow patterns; and
determining the contaminant level of each air intake path by using known, predetermined or measured values of flow rate in each air intake path for each of the plurality of different flow patterns,
wherein the number of different flow patterns created and the number of contaminant level measurements taken are sufficient to determine the contaminant level in each air intake path.

Varying the flow balance is preferably achieved over the plurality of different flow patterns by partial flow reduction in each of the air intake paths, in turn. In other words, if there are four air intake paths, a first subset of the air intake paths (e.g. three paths) are partially closed while the remaining intake path(s) remain open while the contaminant level is measured. Next, that first subset air intake path is reopened and a second different subset of air intake paths is partially closed while the remaining air intake path(s) remain open and a second measure of the contaminant level is made. This is continued until four different flow patterns are created while four measurements of the contaminant level are taken.

The partial reduction in flow is preferably achieved by partially closing valves in the air intake paths. So, each valve is partially closed in turn while the other valves remain open. In this arrangement, the flow rate through each air intake path may not be known. Therefore, it may be necessary to measure the flow rate in each air intake path, for each of the plurality of different flow patterns.

In an alternative form, the step of varying the flow balance may be achieved by having moveable baffles within the air intake paths. For example, the moveable baffles may be in the form of rotatable discs movable to a number of selectable positions. The discs have openings which, depending upon the selected position, create a predetermined flow rate. Thus, in this arrangement, flow rate measurements may not be required.

In a third alternative method of varying the flow balance, each air intake path may be vented in turn while the other pipes remain unvented. Compared to the other two methods described above, this will result in an increase in air flow through each vented air intake path in turn and may also affect the flow rate in the other air intake paths.

In a preferred form, there are as many flow patterns created as there are air intake paths. Given that there are as many measurements of contaminant level as there are flow patterns, this means the number of measurements of contaminant level equal the number of flow paths too. This will provide enough information to determine the contaminant level in each air intake path, provided the flow rate in each air intake path is also known/predetermined or measured for each flow pattern.

In some arrangements, the flow rate is measured in each air intake path. This is preferably achieved by a flow rate sensor having a reasonably high degree of accuracy. In a most preferred form, flow rate is measured by ultrasonic flow rate sensors, one in each air intake path.

Preferably, with the measured contaminant levels for each flow pattern and the known/predetermined or measured flow rates in each path for each flow pattern, a series of equations may be solved as follows:

$$C_1 = X_1 F_{11} / (F_{11} + F_{12} + \ldots F_{1n}) +$$
$$X_2 F_{12} / (F_{11} + F_{12} + \ldots F_{1n}) \ldots + X_n F_{1n} / (F_{11} + F_{12} + \ldots F_{1n})$$
$$C_2 = X_1 F_{21} / (F_{21} + F_{22} + \ldots F_{2n}) +$$
$$X_2 F_{22} / (F_{21} + F_{22} + \ldots F_{2n}) + \ldots X_n F_{2n} / (F_{21} + F_{22} + \ldots F_{2n})$$
$$\vdots$$
$$C_n = X_1 F_{n1} / (F_{n1} + F_{n2} + \ldots F_{nn}) +$$
$$X_2 F_{n2} / (F_{n1} + F_{n2} + \ldots F_{nn}) + \ldots X_n F_{nn} / (F_{n1} + F_{n2} + \ldots F_{nn})$$

where
$X_1 \ldots X_n$=concentration in air intake paths 1 to n
$C_1 \ldots C_n$=measured contaminant level of the combined air intake paths
$F_{11} \ldots F_{n1}$=flow rate in pipe 1 for flow patterns 1 to n
$F_{12} \ldots F_{n2}$=flow rate in pipe 2 for flow patterns 1 to n
$F_{1n} \ldots F_{nn}$=flow rate in pipe n for flow patterns 1 to n In a preferred form, the air intake paths may be in the form of air sampling pipes. Each air sampling pipe may feed into a respective intake port on a detector unit. The flows may be merged in a manifold, in the detector unit prior to being fed to the detector.

The step of measuring, whether for the contaminant level or the flow rate may involve multiple readings from which an average is taken. Alternatively, any other statistical calculation may be made to determine the central tendency of the multiple readings.

Also disclosed herein is a sensing system for detecting contaminants in air samples from a plurality of air intake paths, the system including:
a control system for controlling flow control means in each of the air intake paths to increase or partially reduce the flow in one or more of the air intake paths to create a plurality of different flow patterns;

a detector to measure the contaminant level of the combined air intake paths, the control system controlling the detector to measure the contaminant level for each of the plurality of different flow patterns;

the control system being further operable to determine the contaminant level of each air intake path using known, predetermined or measured values of flow rate in each air intake path for each of the plurality of different flow patterns; and the control system being operable to create a sufficient number of different flow patterns and to control the detector to take a sufficient number of measurements to determine the contaminant level of each air intake path.

The sensing system may be in the form of a sensing unit which includes air intake ports corresponding to the number of air intake paths. Each air intake port may be coupled to a respective sampling pipe. Each of the flow control means may be disposed within the sensing unit or alternatively may be disposed in a respective sampling pipe.

Preferably, the control system is able to control the measurement of flow rate.

Also disclosed herein is a sampling point for an environmental sampling system of the type having a at least one elongate sampling duct defined by a peripheral wall and having plurality of sampling inlets located along the duct's length and extending through the wall to allow the ingress of a sample, said environmental sampling system being configured to draw a sample from the environment through the sampling inlets into the duct and to convey the samples through the duct to an analysis device, the sampling point including a sample injection inlet extending into an interior of the duct inward of the peripheral wall thereof.

The sample injection inlet can include a pipe extending through the peripheral wall of the duct. Most preferably the pipe has an outlet at or near the centre of the duct, away from the peripheral wall of the duct.

The sample injection inlet can have its outlet facing in a downstream direction of flow in the duct. In a preferred form the sample injection inlet is an L-shaped pipe, with a first inlet end for drawing a sample from the environment and a second, outlet end located within the duct and having an outlet facing in a downstream direction of flow in the duct.

Also disclosed is a method in an environmental sampling system of the type having a at least one elongate sampling duct defined by a peripheral wall and having plurality of sampling inlets located along the duct's length and extending through the wall to allow the ingress of a sample, said environmental sampling system being configured to draw a sample from the environment through the sampling inlets into the duct and to convey the samples through the duct to an analysis device, the method including:

providing a structure to ameliorate diffusion of at least a front of a discrete sample portion, along the duct, as the sample portion travels down the duct.

The structure can be a sampling point including a sample injection inlet extending into an interior of the duct as described above. The structure could also be a structure that creates turbulence within the duct configured to prevent laminar flow within the duct in use. For example, the structure could be a contoured or textured wall of the duct; a turbulator; a passive or active rotating element or the like.

Also disclosed herein is a sampling system for an environmental analysis system, said sample system including at least one elongate sampling duct defined by a peripheral wall and having plurality of sampling inlets located along the duct's length and extending through the wall to allow the ingress of a sample into the duct, said environmental sampling system being configured to draw a sample from the environment through the sampling inlets into the duct and to convey the samples through the duct to environmental analysis system, the sampling system further including means to ameliorate diffusion of at least a front of a discrete sample portion, along the duct, as the sample portion travels down the duct. The structure can be a sampling point including a sample injection inlet extending into an interior of the duct as described above. The structure could also be a structure that creates turbulence within the duct configured to prevent laminar flow within the duct in use. For example, the structure could be a contoured or textured wall of the duct; a turbulator; a passive or active rotating element or the like.

The structure could extend substantially the whole length of the duct, or be localised, e.g. at or near, one or all, of the sampling inlets.

Further disclosed herein is a method in an environmental sampling system of the type having at least one elongate sampling duct having plurality of sampling inlets located in series along the duct's length to allow the ingress of a sample from the environment, said environmental sampling system being configured to draw a sample from the environment through the sampling inlets into the duct and to convey the samples through the duct to an analysis device, the method including: changing the airflow characteristic in the duct to after a local sample concentration at or near at least one particular sampling inlet to increase the local sample concentration towards the sample concentration in the atmosphere surrounding the particular sampling inlet.

Changing the airflow characteristic can include stopping or reversing a direction of flow in the duct to so that a portion of a sample adjacent the particular sampling inlet is expelled from the sample inlet. The method then includes drawing an additional sample from the environment via the particular sample inlet. The steps of stopping or reversing a direction of flow in the duct to so that a portion of a sample adjacent the particular sampling inlet is expelled from the sample inlet, and drawing an additional sample from the environment via the particular sample inlet can be repeated one or more times.

The method can include oscillating the direction of flow in the duct such that a repeated process of expulsion and re-sampling the environment occurs.

The method can then include transporting the contents of the duct to the analysis device. This transportation is preferably performed with minimal dilution of the sample within the duct, or mixing between longitudinally positioned portions of the sample of the duct. For example the method can include; one or more of the following:

closing one or more of the sampling inlets prior to transportation, opening duct at an upstream position to provide a low flow impedance;

blowing the sample along the duct from an upstream position.

An environmental sampling system of the type having at least one elongate sampling duct having at least one sampling inlet located along the duct's length to allow the ingress of a sample from the environment, said environmental sampling system being configured to draw a sample from the environment through the or each sampling inlet into the duct and to convey the samples through the duct to an analysis device, The system further including sample amplification arrangement to ameliorate dilution of the sample by air flow in the duct.

The sample amplification arrangement could include a device to reverse flow direction in at least a portion of the duct. The device to reverse flow direction is preferably arranged to cause multiple reversals of flow direction to promote mixing of an air sample at or adjacent a sampling inlet. The device to reverse flow could be, for example, a reversible fan, bellows, reciprocating piston, vibrating membrane, or the like.

Also disclosed herein is an environmental sampling system of the type having at least one elongate sampling duct having plurality of sampling inlets located in series along the duct's length to allow the ingress of a sample from the environment that is configured to perform the above method. The environmental sampling system can include one or more of the following:

One or more valves to control flow along the duct and/or through one or more of the sampling inlets;

fans, blowers or other flow inducing means to control flow along the duct and/or through one or more of the sampling inlets.

A particle detection system, and preferably a smoke detection system, is also provided that includes an environmental sampling system of the above type to deliver air samples for analysis from a plurality of locations.

In a preferred form the particle detection system comprises a detection system according to the following aspects of the present invention. In this case, the accessory can comprise any one or more of: a sampling inlet or a sampling point; a valve; a filter; a duct or portion of a duct; a flow-inducing device such as a fan, piston, bellows, pump, vibrating membrane or the like; and a localisation module.

In accordance with an further aspect of the present invention there is provided a detection system, such as a particle detection system of any of the types described herein, for detecting an abnormal condition in an air volume, the detection system including a detector for detecting an abnormal condition of the air volume and an accessory, wherein the detector and the accessory are in fluid communication with each other and the air volume by an air flow path.

wherein the detector is operable to communicate, at least unidirectionally, with the accessory through the air flow path.

The detector may be in the form of a particle detector which is used to detect an abnormal level of particles within the sampled air volume. Preferably, the type of particle detector is an aspirating smoke detector i.e. includes a fan or other type of fluid drive. Accordingly, in this preferred embodiment, the detector is able to send signals to the accessory through the air flow path by changing the air flow characteristics in the air flow path. In this preferred embodiment, that can be achieved by adjusting flow speed or direction. Suitably, the changes in the air flow characteristics may be detected by the accessory, with the accessory being responsive to the detected change. Thus the change in air flow characteristics functions as a signal from the detector to the accessory.

Preferably the air flow path comprises an air sampling system or environmental sampling system as described in any one of the aspects of the present invention or embodiments described herein.

The accessory could comprise a detector for detecting an abnormal condition of the air volume. The accessory detector may be any one of the following types: particle detector, gas detector, temperature/heat detector, humidity detector. Alternatively, the accessory may comprise a filter, For example, the filter may be a pre-filter which is used before particle detection. The accessory can be in the form of a valve or fan incorporated into the air flow path.

The air flow path suitably includes a sampling pipe network including pipe and inlet ports. In the embodiment which utilises a particle detector, the air flow path may also include the flow path through the detector including the aspirator i.e. the fan and the detection chamber. The exhaust from the detector also forms part of the air flow path. The flow path through the accessory is also understood to be part of the air flow path.

The detector and the accessory may subsist as separate units along the air flow path. The accessory may be retrofittable into an existing detection system such as a smoke detection system already having a smoke detector unit with a sampling pipe network.

Preferably the detector sends operational information to the accessory. For example, the detector may send information about the operation of the detector such its current mode of operation. The accessory's response to the sensed information may be to adjust its settings or perform a calibration or recalibration or change its operating state.

As discussed above, one mode of communicating through the air flow path is for the detector to cause a change in air flow characteristics which may be detected by the accessory. The change in air flow characteristics may include any aberration in the air flow which is detectable by the accessory. This may include a change in the air flow rate or direction; or a pressure surge or wave in the air flow path. This may be created by an air flow apparatus within or within the control of the detector such as the aspirator fan within the detector. The aspirator is preferably controlled by a programmable controller within the detector. Thus, suitable programming will cause the detector to send the required signal(s).

The change in flow characteristics of the air flow path may vary so that different signals mean different things to the accessory. For example, rather than a single change in flow rate, there may be a plurality of changes such as pulses of increased flow, the number of pulses corresponding to particular information. Alternatively, the degree of change in the flow rate or the actual measured flow could also be used to denote different information.

Preferably, the accessory has a sensing system comprising one or more sensors to detect the changes in flow characteristics.

Communication through the air flow path could be by way of sound transmission detectable by the accessory. For example a change in fan noise might be used for signalling purposes. Otherwise, sound signals e.g. acoustic, ultrasound or infrasound could be created by the detector or other component of the system and sensed by the accessory. Suitably, the accessory has a microphone or other transducer to detect such noises as part of its sensing system.

In an alternative form of the invention, vibrations may be created by the detector e.g. tapping of the pipe with a suitable vibration sensor provided in the accessory.

The detector could alternatively transmit light signals with a light sensor on the accessory, although such a system may require a line of sight through the air flow path.

While the above discussion has focused on unidirectional communication between the detector and the accessory, bidirectional communication is also possible. Communication from the accessory to the detector may be created by the presence of a valve in the accessory with the consequential effect on the air flow characteristics being detected by a flow sensor in the detector. Some accessories also incorporate a fan. This fan may also be used to have an influence in the air flow characteristics which may be sensed by the detector.

In accordance with another aspect of the present invention there is provided an accessory for a detection system, the detection system for detecting an abnormal condition in an air volume, the accessory being fluidly connectable to the detection system and the air volume by an air flow path, wherein the accessory is operable to receive communication transmitted by the detection system through the air flow path. The accessory may include any of the features discussed above in accordance with the first aspect of the invention.

In accordance with another aspect of the present invention there is provided a detection system for detecting an abnormal condition in an air volume, the detection system including a detector for detecting an abnormal condition of the air volume and an accessory, wherein the detector and the accessory are in fluid communication with each other and the air volume, wherein the detector is operable to communicate, at least unidirectionally with the accessory by effecting changes in air flow characteristics of the fluid communication, said changes being detectable by the accessory.

In accordance with another aspect of the present invention there is provided an accessory for a detection system, the detection system for sensing an abnormal condition in an air volume, the accessory being fluidly connectable to the detection system and the air volume, wherein the accessory is operable to detect changes in air flow characteristics generated by the detection system. Preferably, the accessory is operationally responsive to said changes. However, the accessory may also be operationally responsive to a lack of any changes.

The detection system and the accessory in the preceding two aspects above may incorporate any of the preferred features discussed above.

In accordance with another aspect of the present invention there is provided a method of operating a detection system which detects an abnormal condition in an air volume, the detection system including a detector for detecting an abnormal condition of the air volume and an accessory, the detector and the accessory being in fluid communication with each other and the air volume by an air flow path, the method including: sending a signal from the detector to the accessory through the air flow path, wherein the accessory is responsive to the signal or a lack of signal.

The detector may send a signal to the accessory through the air flow path by effecting a change in the air flow characteristics. Alternatively, the signal may be sent according to any of the alternative methods discussed above in connection with the above aspects of the invention.

The accessory response to the signal or to the lack of signal may be to shut down, go into a fault mode or adjust its operating characteristics.

In accordance with another aspect of the present invention there is provided a method of operating a detection system which detects an abnormal condition in an air volume, the detection system including a detector for detecting an abnormal condition of the air volume and an accessory, the detector and the accessory being in fluid communication with each other and the air volume by an air flow path, the method including: receiving, at an accessory, a signal via the air flow path; controlling the accessory on the basis of the received signal.

The step of receiving a signal can include detecting a change in a flow parameter, such as flow rate, direction or pressure or the like, in part of the airflow path at the accessory.

Controlling the accessory can include changing at least one operational parameter or state of the accessory in response to the received signal. Preferably the change of the operational parameter changes a flow condition in the airflow path.

In accordance with another aspect of the present invention there is provided a method of operating a detection system which detects an abnormal condition in an air volume, the detection system including a detector for detecting an abnormal condition of the air volume and an accessory, the detector and the accessory being in fluid communication with each other and the air volume by an air flow path, the method including: sensing at an accessory, a change in air flow in the air flow path; controlling the accessory on the basis of the sensed change.

The step of receiving a signal can include detecting a change in a flow parameter, such as flow rate, direction or pressure or the like, in part of the airflow path at the accessory.

Controlling the accessory can include changing at least one operational parameter or state of the accessory in response to the received signal. Preferably the change of the operational parameter changes a flow condition in the airflow path.

In the above embodiments the accessory can include any one or more of: a valve, fan, flow control device, detector, filter.

As will be appreciated a system, detector and or accessory can advantageously be used in any one of the embodiments described herein. In particular using such an accessory and method minimises the complexity of installation of the accessory since additional communication lines need to be connected between the accessory and other system components.

Also disclosed herein is a method in an environmental sampling system of the type having at least one elongate sampling duct having plurality of sampling inlets located along the or each duct's length to allow the ingress of a sample from the environment, said environmental sampling system being configured to draw a sample from the environment through the sampling inlets into the duct and to convey the samples through the duct to an analysis device to detect the presence of a threat substance in the sample, the method including:

operating in a detection mode in which the presence and or concentration of the threat substance is being monitored, and in the event at least one criterion is met, the system performs the step of:

operating in a localisation mode to determine which of the sampling inlets the threat substance entered the system.

The method can include operating in a training mode to characterise a sample flow through the at least one sampling duct to the analysis device so as to enable determination of which of the sampling inlets the threat substance entered the system in the localisation mode.

The localisation mode can include a sample amplification phase and transportation phase.

The localisation mode can include a purge phase.

In a further aspect there is provided a particle detection system configured to monitor a series of physical locations for the presence of particles, the particle detection system including a particle detector and a sampling pipe network for delivering air samples from the series of physical locations to the particle detector for analysis, said sampling pipe network being arranged such that: each of said physical locations has a sample inlet arrangement through which an air sample is drawn into the sampling pipe network, each of said sample inlet arrangements being connected to a sampling pipe at a respective sampling connection location, wherein the average distance between the sample inlet arrangements of neighbouring physical locations is less than the average distance between the sampling connection locations of neighbouring physical locations when measured along a flow path within the sampling pipe network.

In the event that a sample inlet arrangement includes multiple sample inlets the centroid of the sample inlets can be used to determine the distance to its neighbouring arrangement(s). Similarly if the sampling connection location of a physical location includes multiple points of connection to the sampling pipe the centre of the multiple points of connection can be used to determine the distance to its neighbour(s) along the flow path.

In some embodiments the sampling pipe passes through the regions being monitored to service the regions, in other embodiments the sampling pipe runs near, but not through the regions (such as might be the case where the sampling pipe runs above a ceiling of a room, or outside an equipment cabinet which is being monitored, in order to service the region.

In preferred embodiments the sampling pipe includes a first portion extending past or through regions being serviced by the sampling pipe and a second portion connected to the sampling pipe network upstream of the first portion which extends past or through at least one region being serviced by the first portion. Preferably the second portion extends past or though a plurality of regions that the first portion extends past or through. Most preferably the second portions extend past or through a majority of the regions that the first portion extends past or through.

In some forms the first and second portions extend substantially side by side, most preferably they run parallel to each other.

In a preferred form the second portion services a location positioned between locations serviced by the first portion. Most preferably locations positioned adjacent one another are alternately serviced by the first and second portions of the pipe network. Such an arrangement acts to spread out the points of connection along flow path of the sampling pipe network, which aids in reducing ambiguity in particle localisation A region should be considered to be serviced by either a given (e.g. the first or second) portion of the common portion of the sampling pipe network if a point of connection of the region's sample inlet arrangement is made to the given portion of the common portion of the sampling pipe network. In another aspect there is provided a particle detection system arranged to monitor particles in a plurality of regions, said particle detection system including a particle detector and a sampling pipe network including a plurality of sample inlets into which particles are drawn for transport to the detector for analysis. Said sampling inlets being arranged to draw samples from a specific region, wherein the sampling pipe network includes a plurality of side by side pipes interconnected in series, wherein the sampling inlets corresponding to at least two regions that are located sequentially adjacent each other along the length of the plurality of side-by-side pipes are connected to different members of the plurality of pipes. Most preferably when the plurality of pipes has two pipes the sampling inlets of sequentially adjacent regions are alternately connected to the first or second pipe.

In another aspect of the present invention there is provided an apparatus comprising: a delivery system for delivering a test substance to a particle detector arranged to protect a location; an activation means to activate the delivery system to deliver the test substance;

an indicator signalling the activation of the delivery system, such that the activation can be automatically detected by an image capture system arranged to capture images of the location.

The apparatus can further include an interface enabling data regarding the activation to be entered into the apparatus for storage or transmission thereby. The delivery system can comprise at least one of: a test substance generator; a duct for delivering a test substance to a the particle detector from a test substance generator; a fan, pump or the like to move the test substance through the apparatus to the particle detector. The indicator preferably comprises one or more radiation emitters configured to emit radiation for capture in an image. The apparatus can include a synchronisation port, to enable data transfer to and/or from the apparatus to an external device, such as the particle detection system or video capture system.

In another aspect the present invention provides a method for correlating an address in a particle detection system, said address corresponding to a physical location, with a location being monitored in a video capture system that monitors a plurality of locations; the method comprising; causing the detection of particles in the particle detection system at the address;

indicating visually a physical location corresponding to the address; identifying the visual indication of the physical location in at least one image captured by the video capture system;

correlating address with a location of the plurality of locations monitored by the video capture system.

The method preferably includes correlating the address with one or more of: a camera that captured the at least one image in which the visual indication was identified; One or more of a pan, tilt or zoom parameter of a camera that captured the at least one image in which the visual indication was identified.

The method can include providing the correlation data to the video capture system to enable selective capture, storage or display of images relating to corresponding to an address in the particle detection system in the event that particles are detected by the particle detection system at the address. Described herein this allows video verification of the particle detection event.

The step of indicating visually a physical location corresponding to the address can include, emitting radiation that can be captured and identified in an image captured by the video capture system. This can includes selectively activating a radiation source in a detectable pattern. For example on-off modulating a light source.

The step of causing the detection of particles in the particle detection system preferably includes emitting particles at, or near, the physical location so as to be detected by the particle detection system at the address.

The step of causing the detection of particles in the particle detection system at the address; and indicating visually a physical location corresponding to the address are preferably performed simultaneously to enable temporal correlation between images captured by the video capture system with a particle detection event in the particle detection system.

Most preferably the method is performed using an apparatus of the previous aspect of the present invention.

BRIEF DESCRIPTION OF THE DRAWINGS

Illustrative embodiments of the invention will now be described by way of a non-limiting example with reference to the accompanying figures. In the figures:

Figure 5:
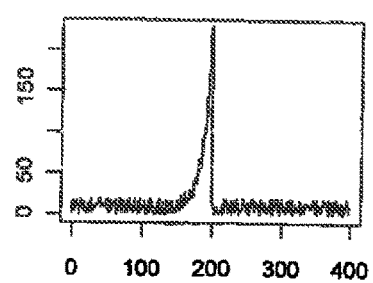
Figure 6:
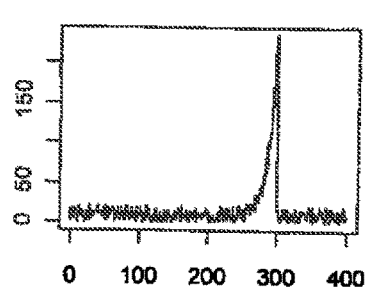
Figure 7:
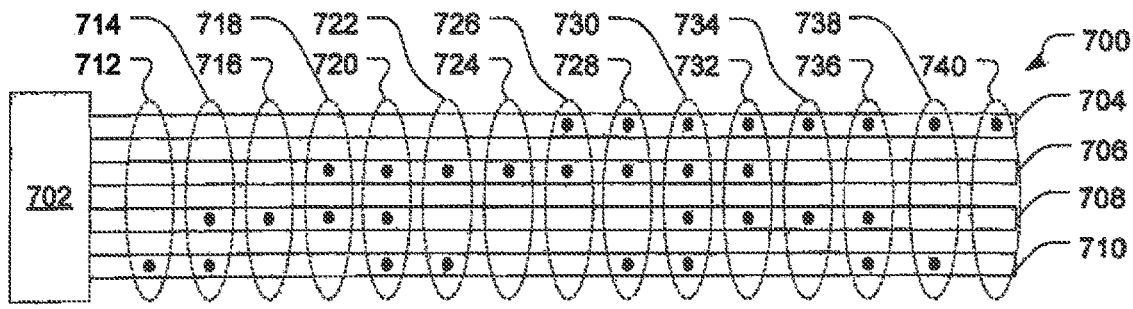
Figure 8:
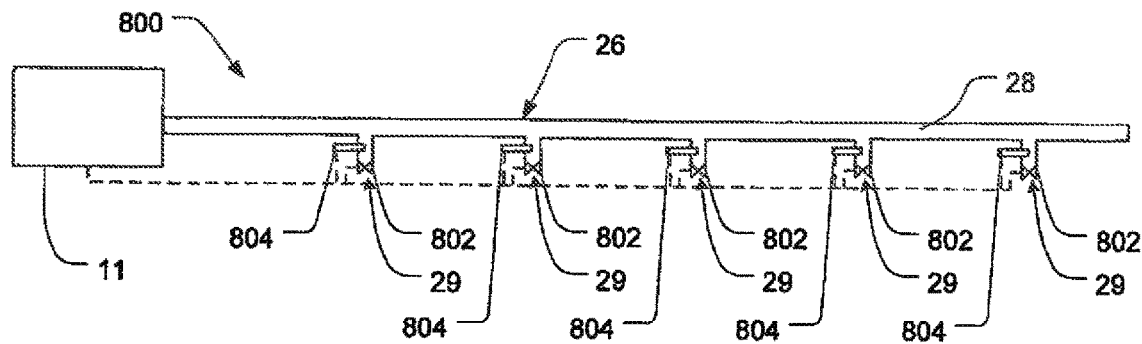
Figure 9A:
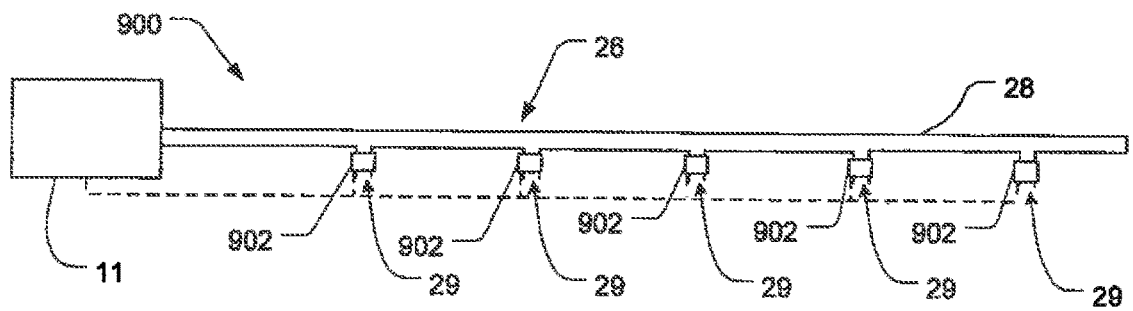
Figure 9B:
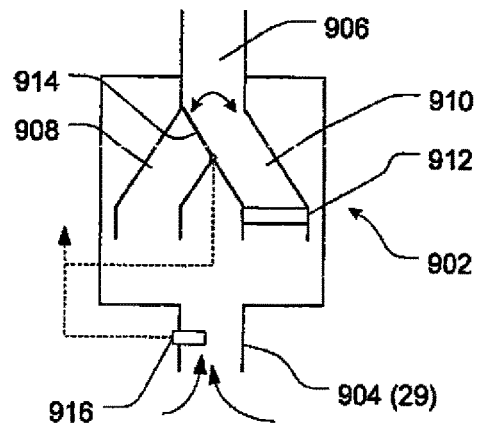
Figure 11A:
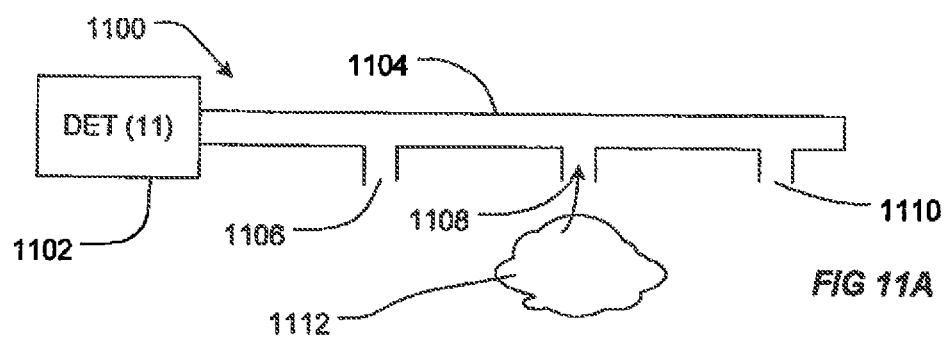
Figure 11B:
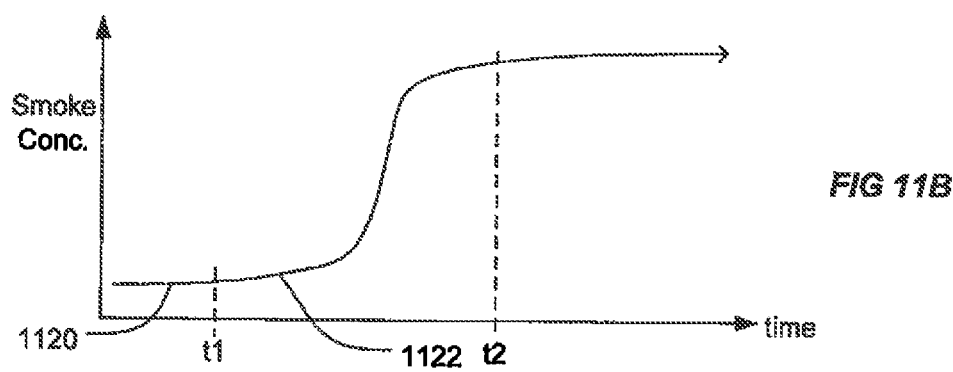
Figure 11C:
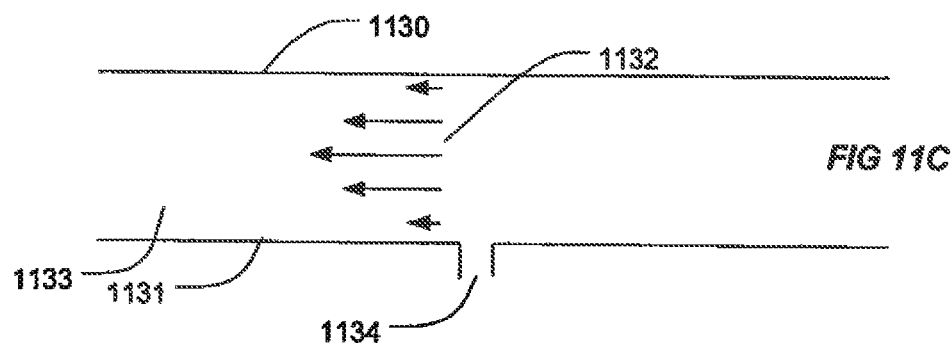
Figure 12:
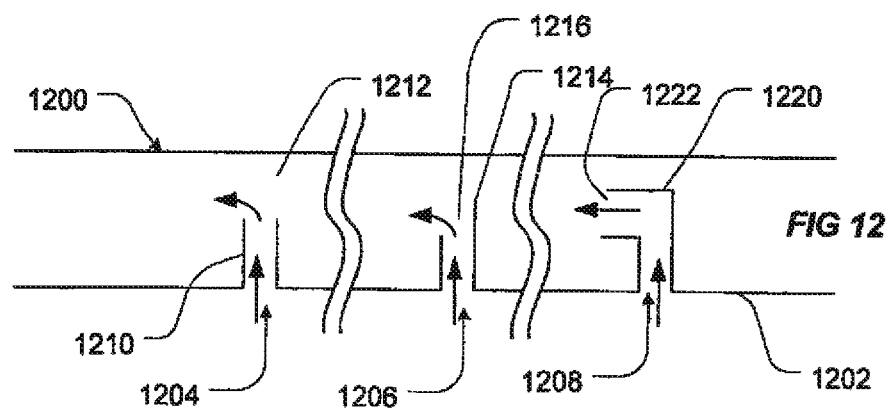

FIGS. 5 and 6 graphically illustrate a timing of events as measured at respective detectors (or branches) of a particle detection system;

FIG. 7 illustrates another embodiment of a particle detection system that is used to determine a location particles entering the system;

FIG. 8 illustrates a particle detection system including a sampling system including a plurality of valves, for altering a sampling parameter of the sampling system [to implement an embodiment of one aspect of the invention];

FIG. 9A illustrates a particle detection system including a sampling system including a plurality of filters which are configured to alter a sampling parameter the sampling system [to implement an embodiment of one aspect of the invention];

FIG. 9B illustrates a filter and valve arrangement used in the system of FIG. 9A;

FIG. 10A is a schematic diagram of a particle detection system according to a preferred embodiment of the present invention;

FIG. 10B is a schematic diagram of a portion of the particle detection system of FIG. 10A;

FIG. 10C is a schematic view of the portion of the particle detection system as per FIG. 10B, except with one of the valves in a partially closed position; and FIG. 10D is a schematic view of the portion as per FIG. 10C, except that one of the other valves is partially closed;

FIG. 11A illustrates a particle detection system;

FIG. 11B is a graph illustrating diffusion of a front of a sample portion as the sample portion travels down a duct;

FIG. 11C illustrates a flow speed profile within the sample duct of FIG. 11A;

FIG. 12 illustrates 3 sampling points according to different embodiments of the present invention, that may ameliorate the effect of the diffusion illustrated in FIG. 11B;

FIGS. 13A to 13D are examples of turbulators that may ameliorate the effect of the diffusion illustrated in FIG. 11B;

FIG. 14 illustrates a particle detection system including an air sampling network that is connected to bellows that can be used to oscillate the direction of sample flow within the air sampling duct to counteract sample dilution by other sampling inlets within the particle detection system;

FIGS. 14A to 14E illustrate an exemplary system that uses a vibrating membrane to perform sample amplification in a manner analogous to that of FIG. 14;

FIG. 15 illustrates a particle detection system including an air sampling system that has an upstream fan that can be used to counteract sample dilution by other sampling inlets within the particle detection system.

FIG. 15B illustrates a particle detection system similar to that of FIG. 15, which has been augmented with a sample flushing system.

Figure 17:
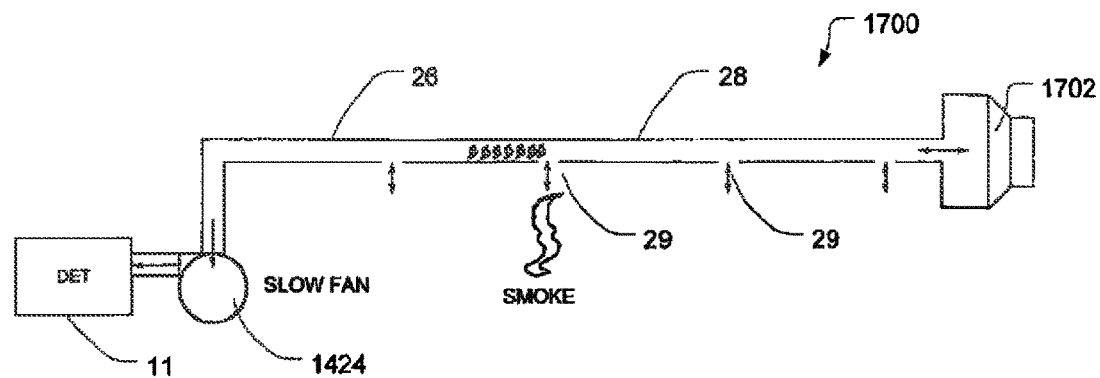
Figure 18:
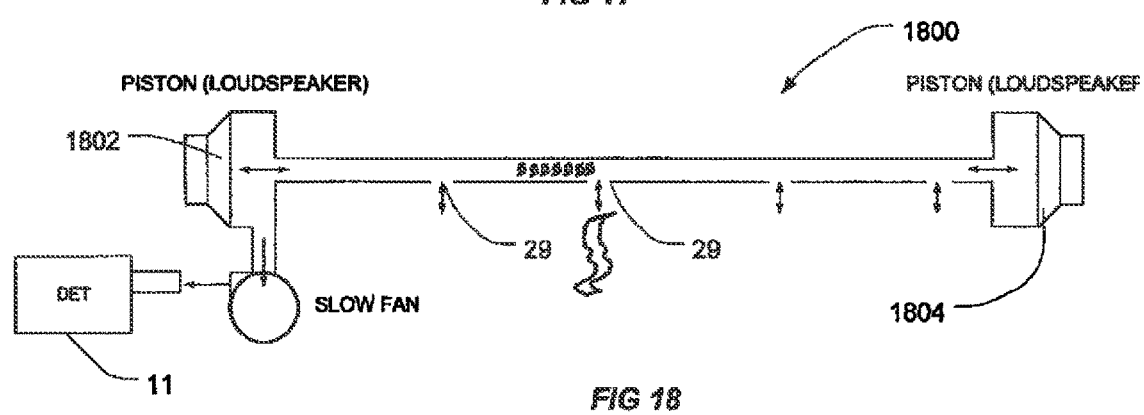
Figure 19:
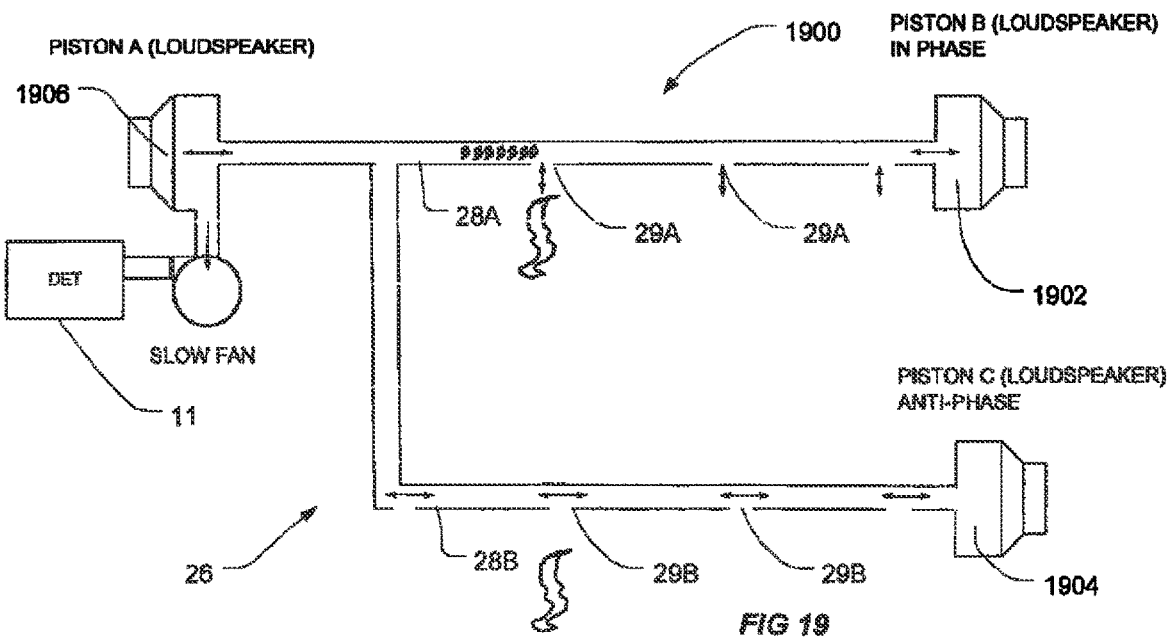

FIG. 16 illustrates a particle detection system having an air sampling system including a valve upstream of the sampling inlets that can be used to open the end of the sampling duct to enhance transport of sample in the duct to the particle detector for analysis;

FIG. 17 illustrates a variant of the system of FIGS. 14A to 14E;

FIG. 18 illustrates a particle detection system including an air sampling network that has a sample amplification arrangement comprising a plurality vibrating membranes; and FIG. 19 illustrates another particle detection system including an air sampling network with branched sampling pipes and which has a sample amplification arrangement comprising a plurality vibrating membranes.

FIGS. 20A and 20B illustrate a variation on the systems of FIGS. 14 and 15 respectively, which include a dedicated localisation module.

Figure 21:
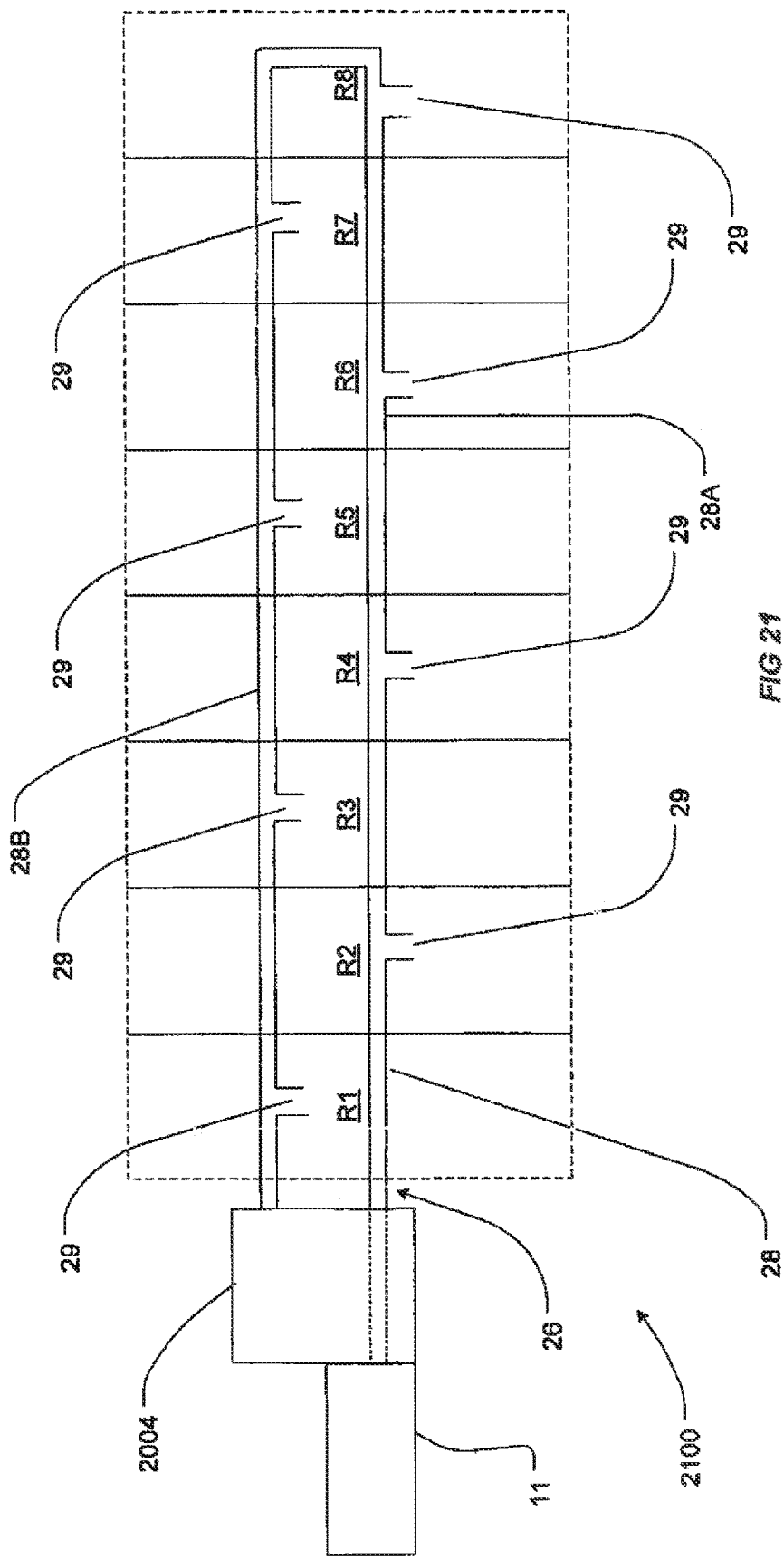

FIG. 21 illustrates a particle detection system according to an embodiment of the present invention, which is arranged to detect particles in a series of regions.

Figure 22:
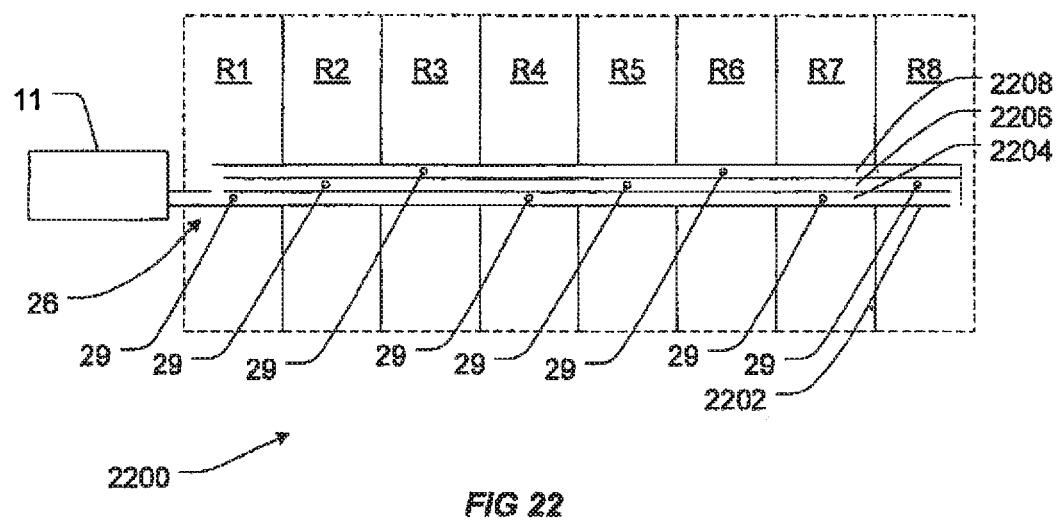
Figure 23:
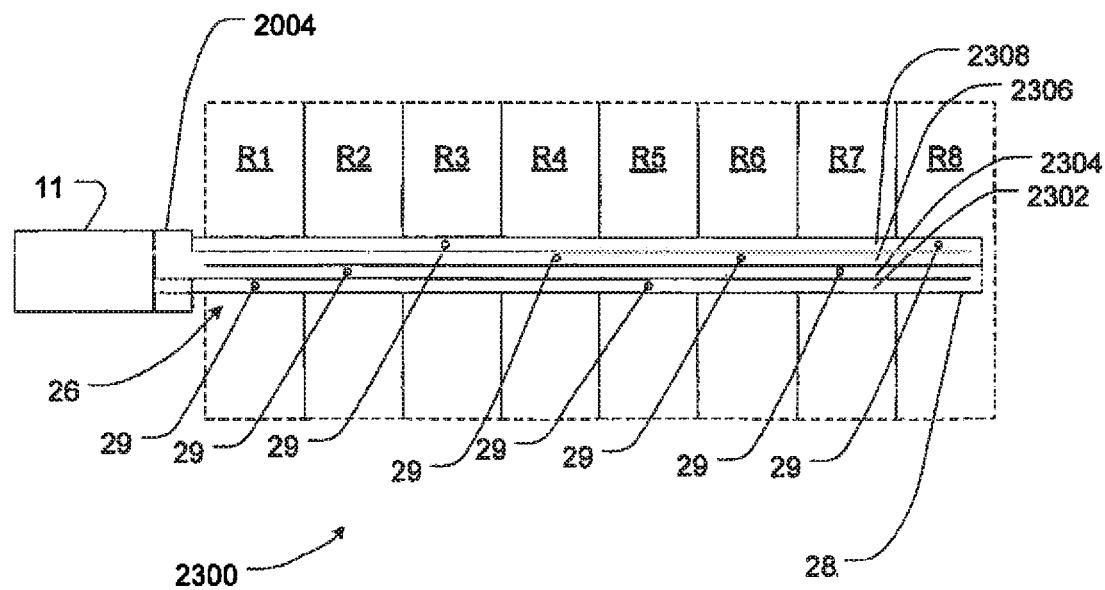

FIGS. 22 and 23 illustrate further two embodiments of a system according to the invention that are arranged to detect particles in a series of regions.

Figure 24:
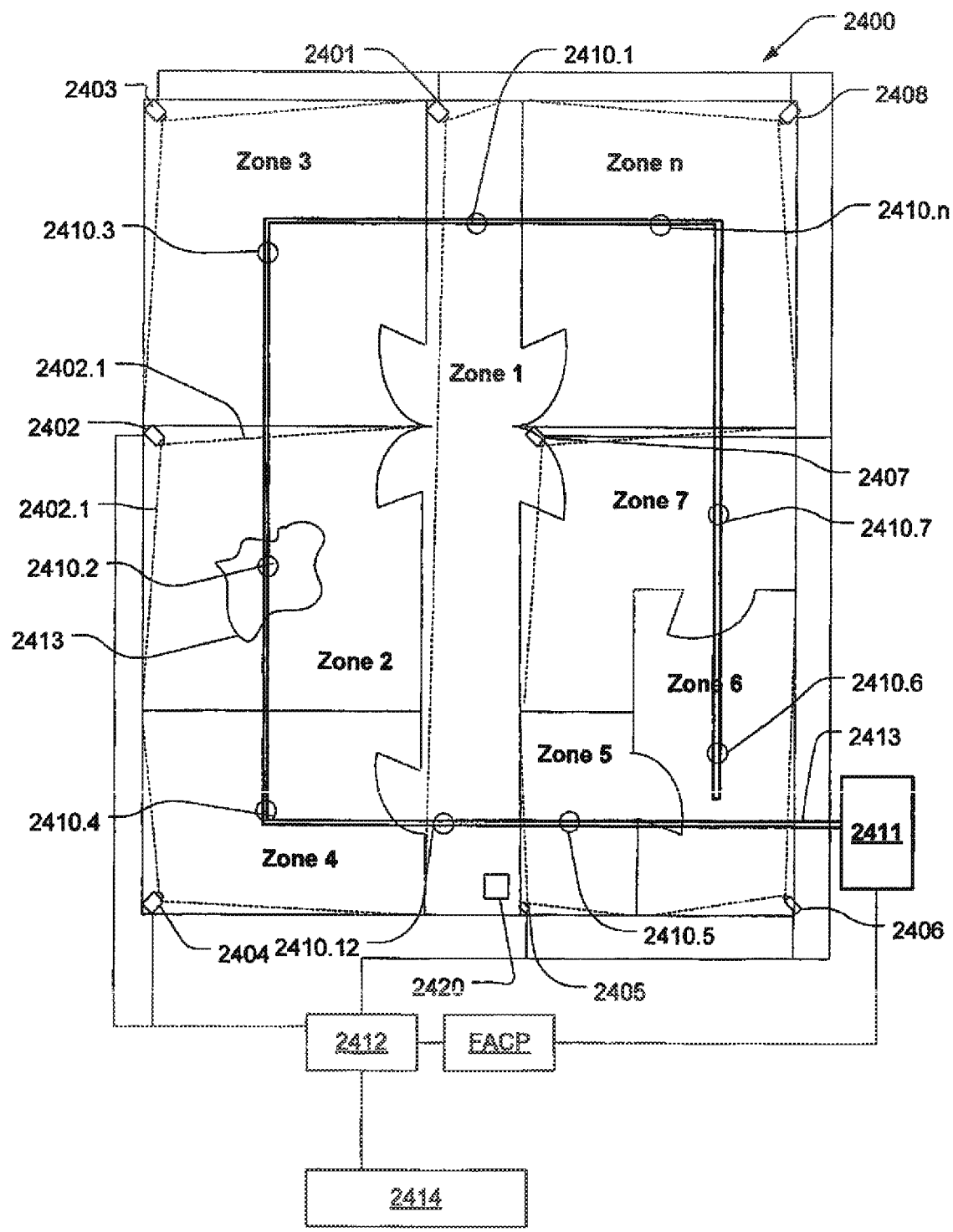

FIG. 24 illustrates a particle detection system incorporating video verification using a video security system.

Figure 25:
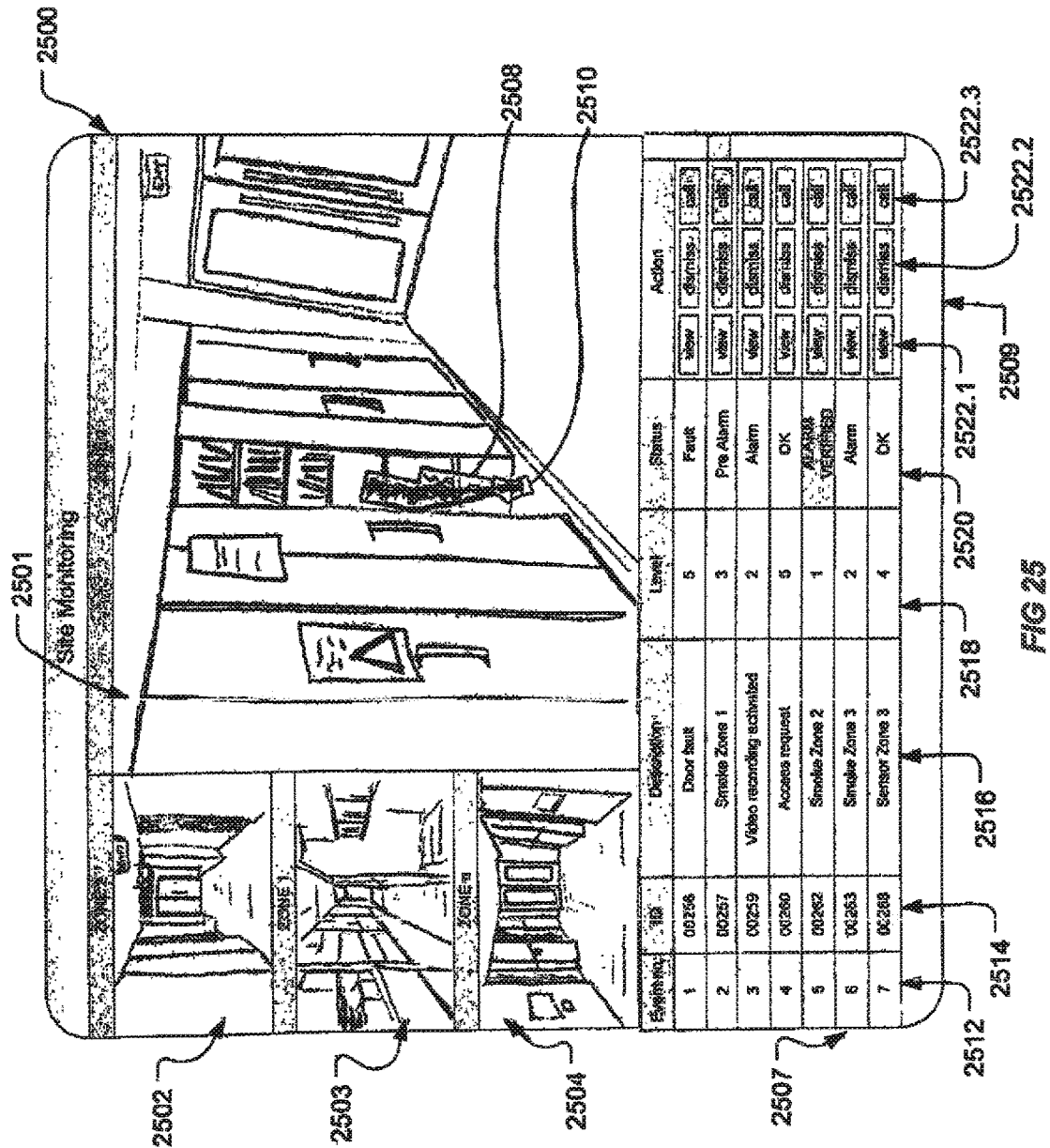
Figure 26:
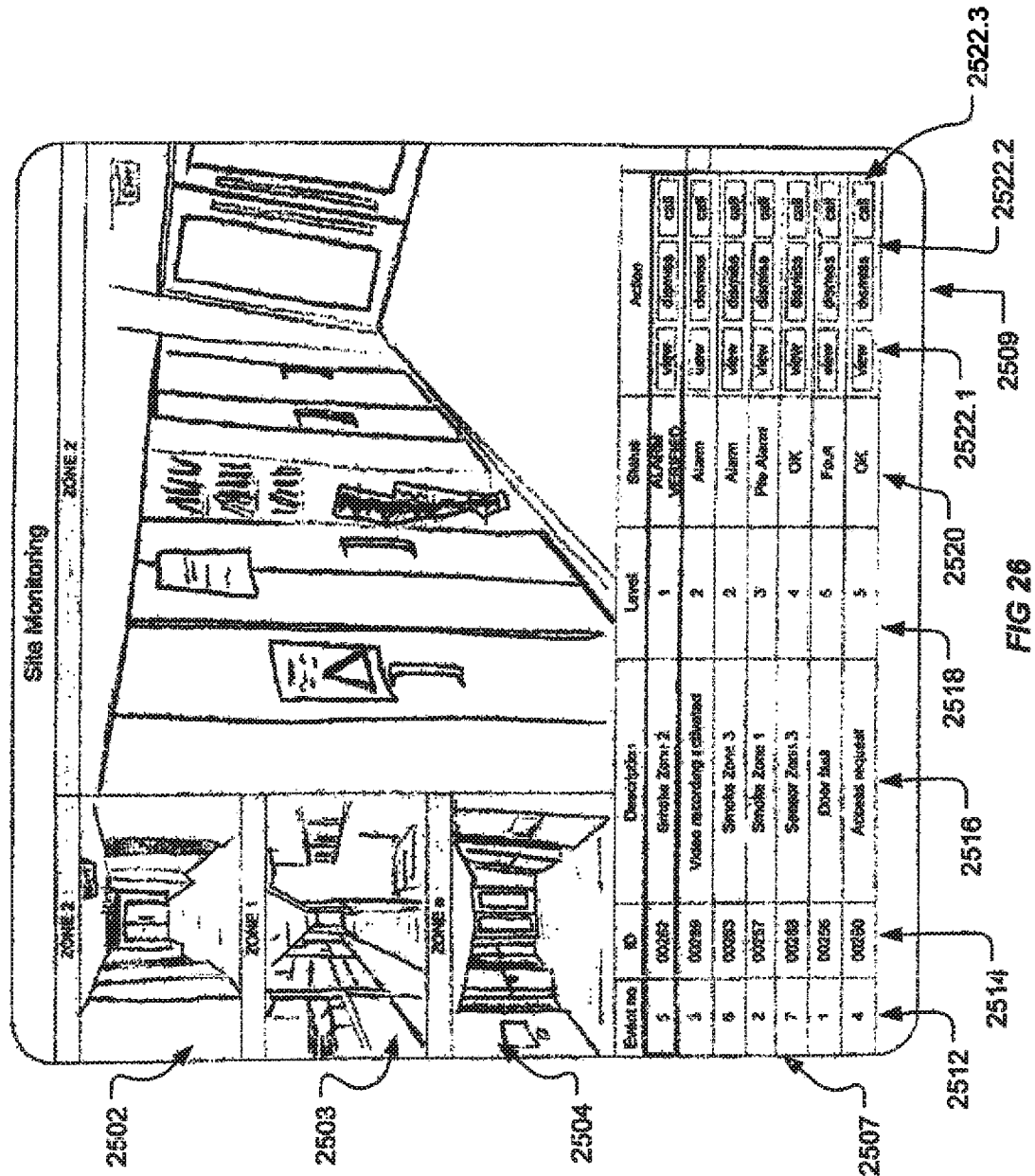

FIGS. 25 and 26 illustrate exemplary user interfaces used for video verification in the system of FIG. 24.

Figure 27:
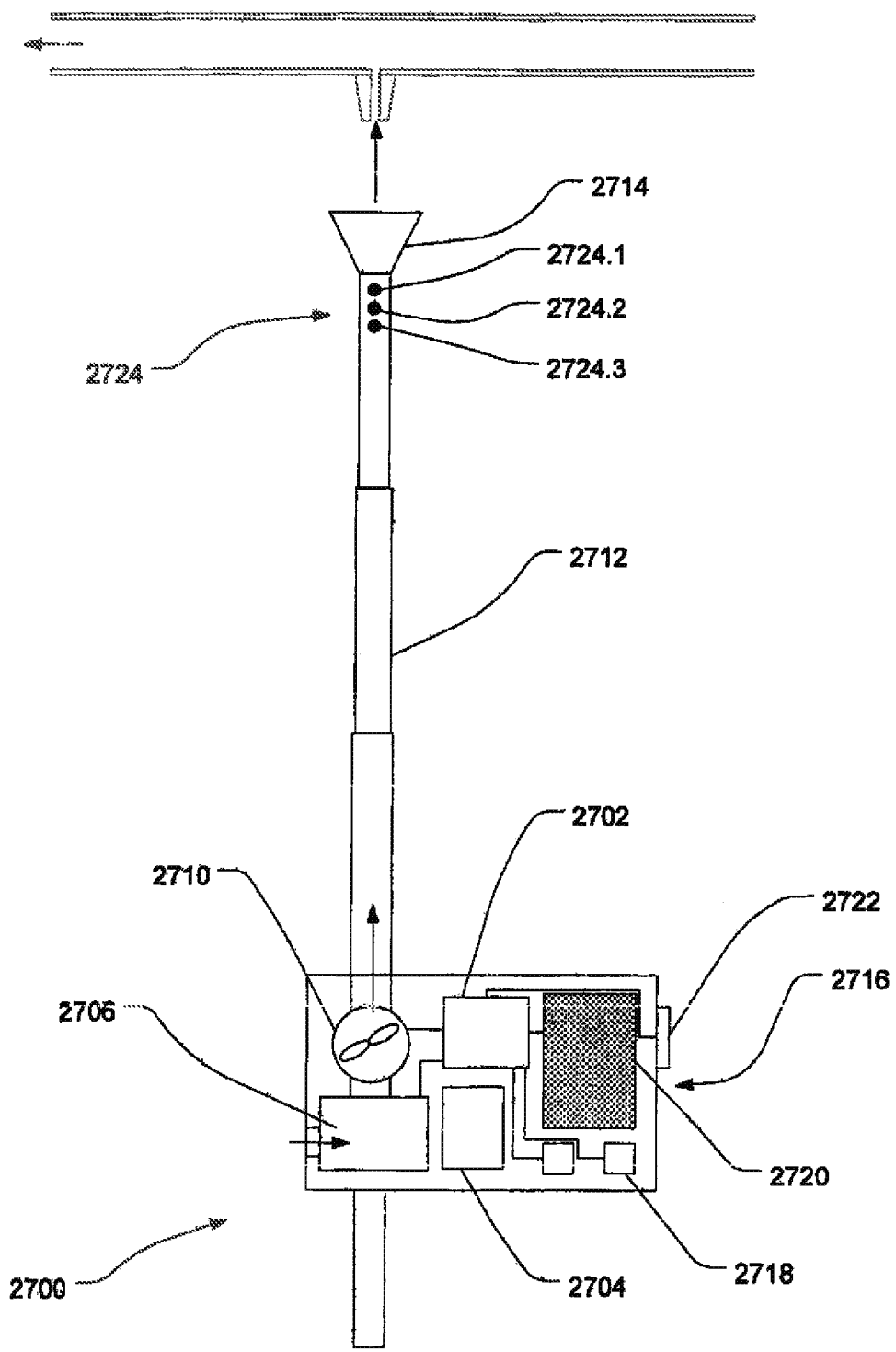

FIG. 27 is a schematic diagram of an apparatus used for commissioning and/or testing of a system of the type illustrated in FIG. 24.

Figure 28:
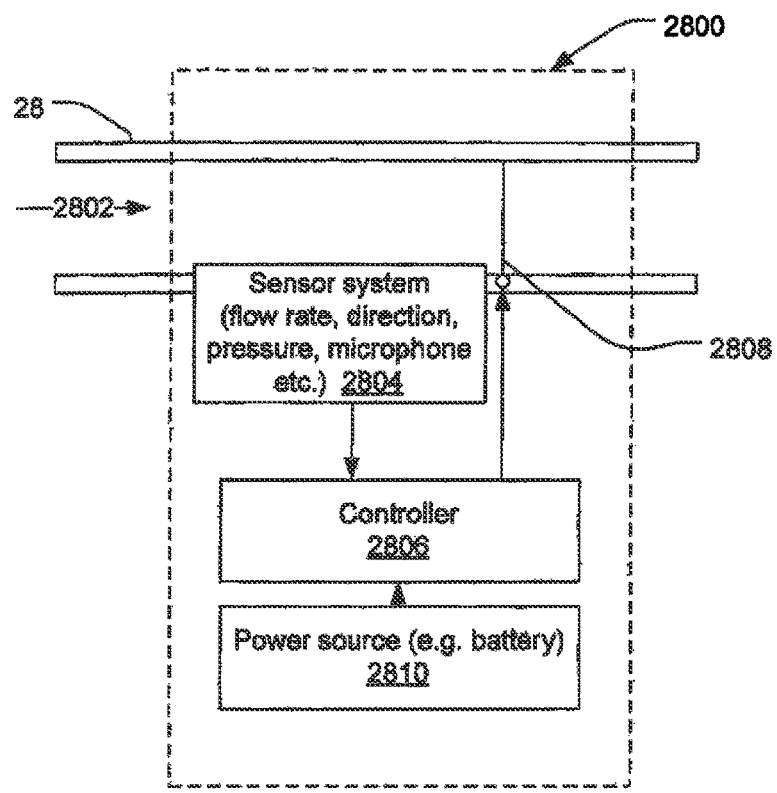

FIG. 28 is an exemplary accessory, in this case a valve, which is arranged to sense a change or condition in flow in the air flow path from another system component and control its operation in response to the sensed change or condition.

Figure 29:
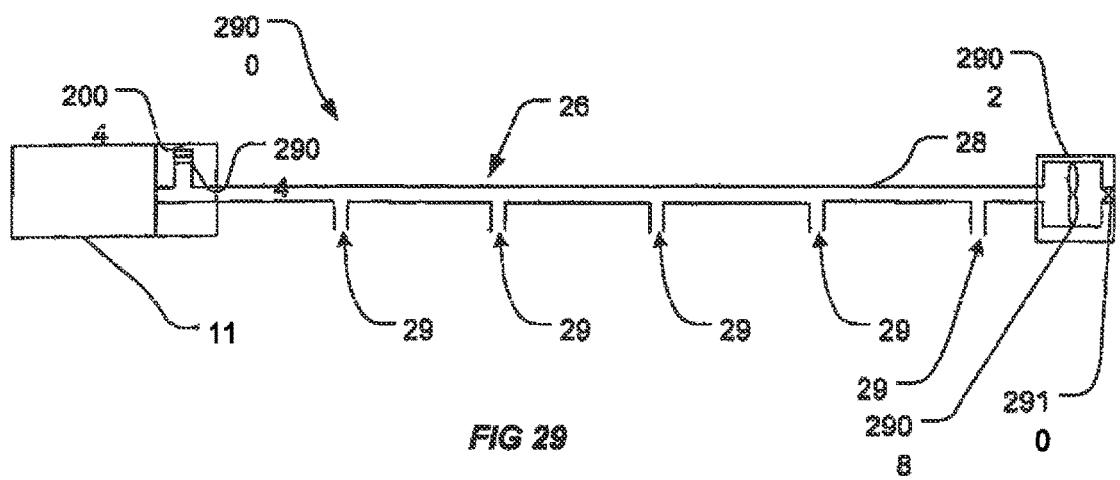

FIG. 29 illustrates a particle detection system incorporating an accessory as described in connection with FIG. 28.

Figure 30:
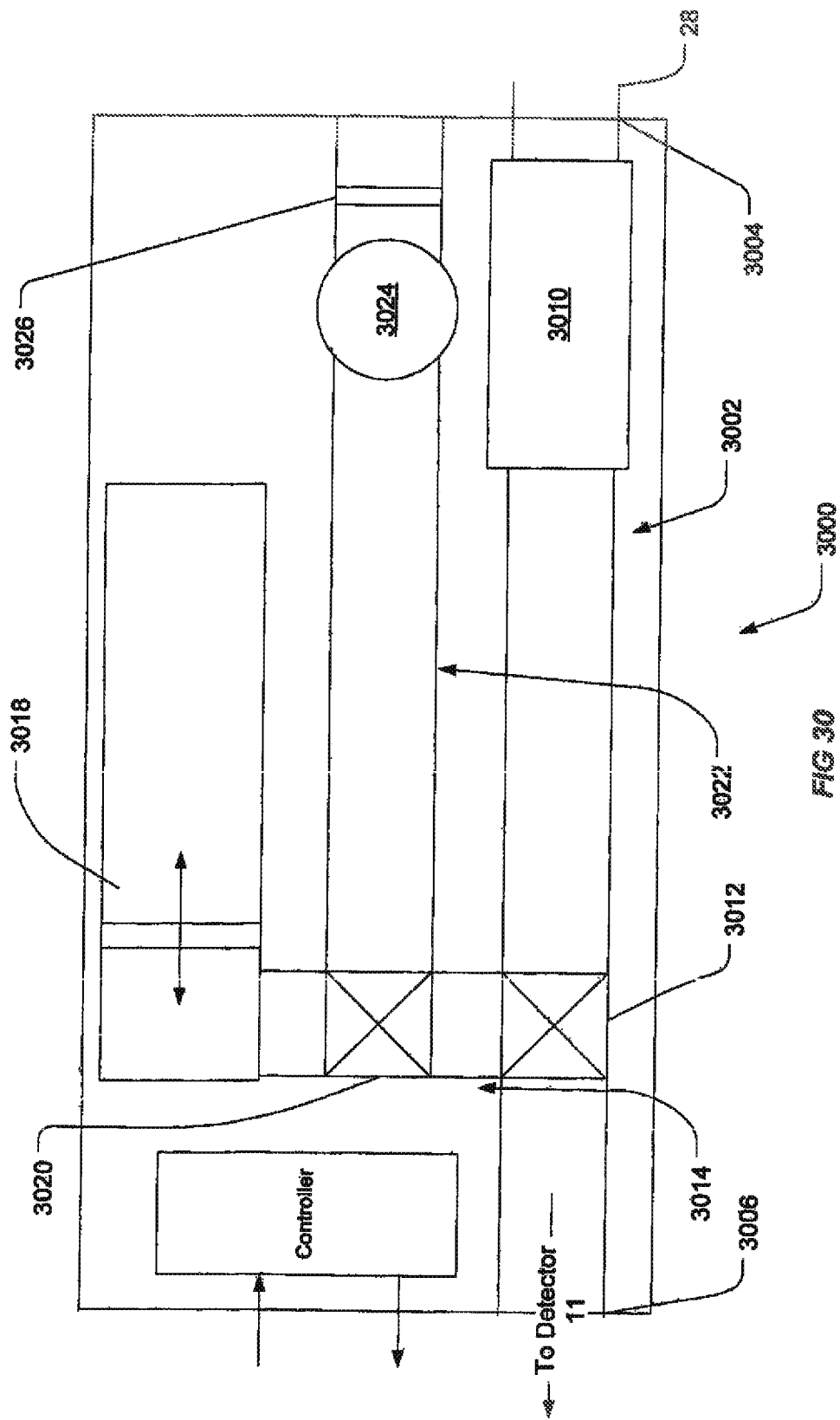

FIG. 30 illustrates an embodiment of a localisation module.

Figure 31:
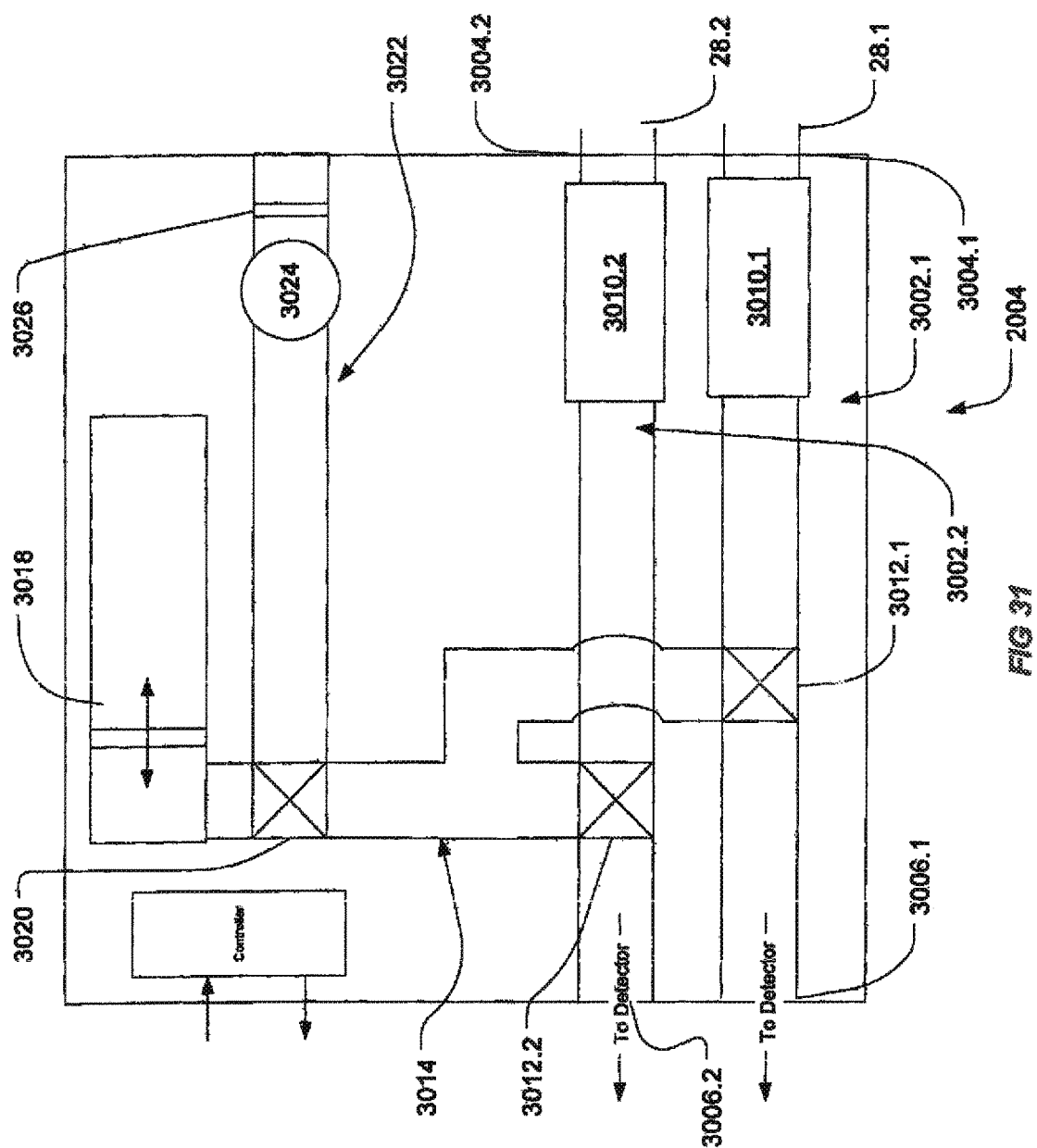

FIG. 31 illustrates another embodiment of a localisation module to which multiple sampling pipes can be connected.

Figure 32:
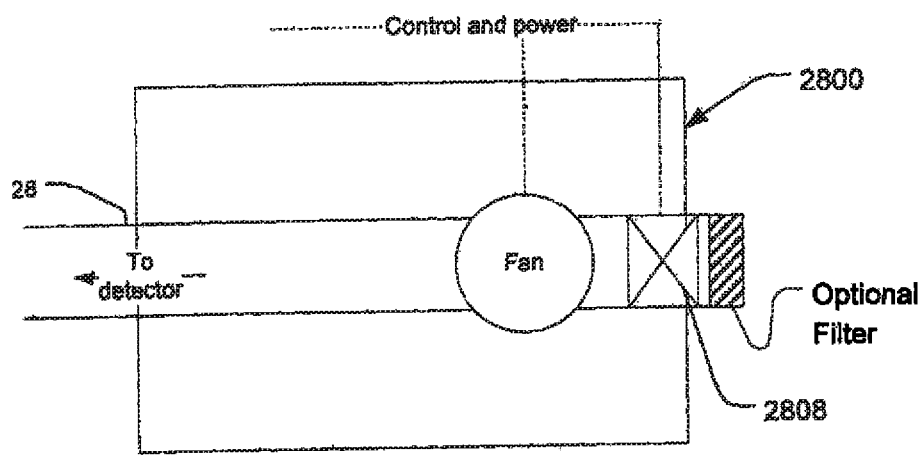
Figure 33:
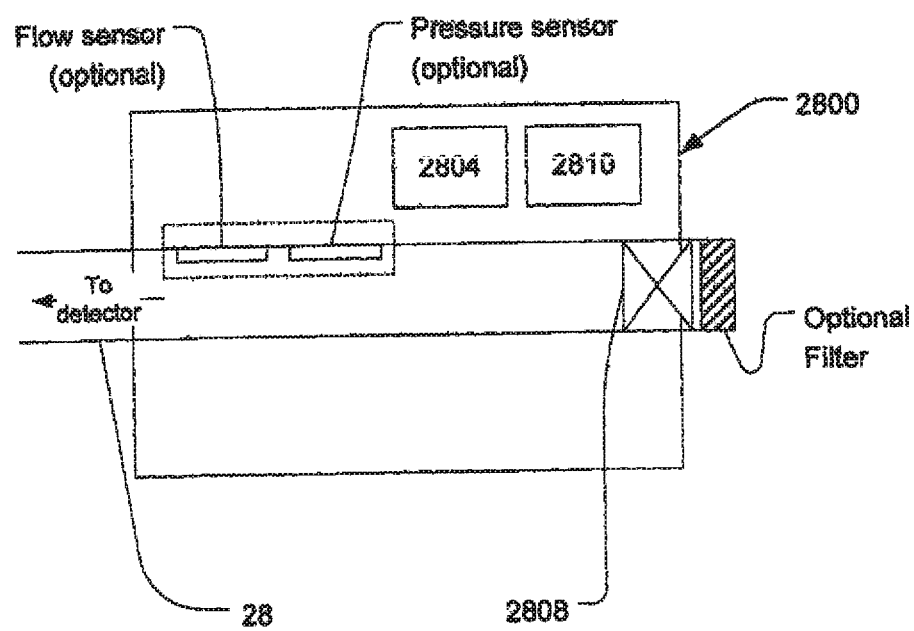

FIGS. 32 and 33 illustrate additional embodiments of accessories similar to that of FIG. 28.

DETAILED DESCRIPTION OF THE EMBODIMENTS

Figure 1:
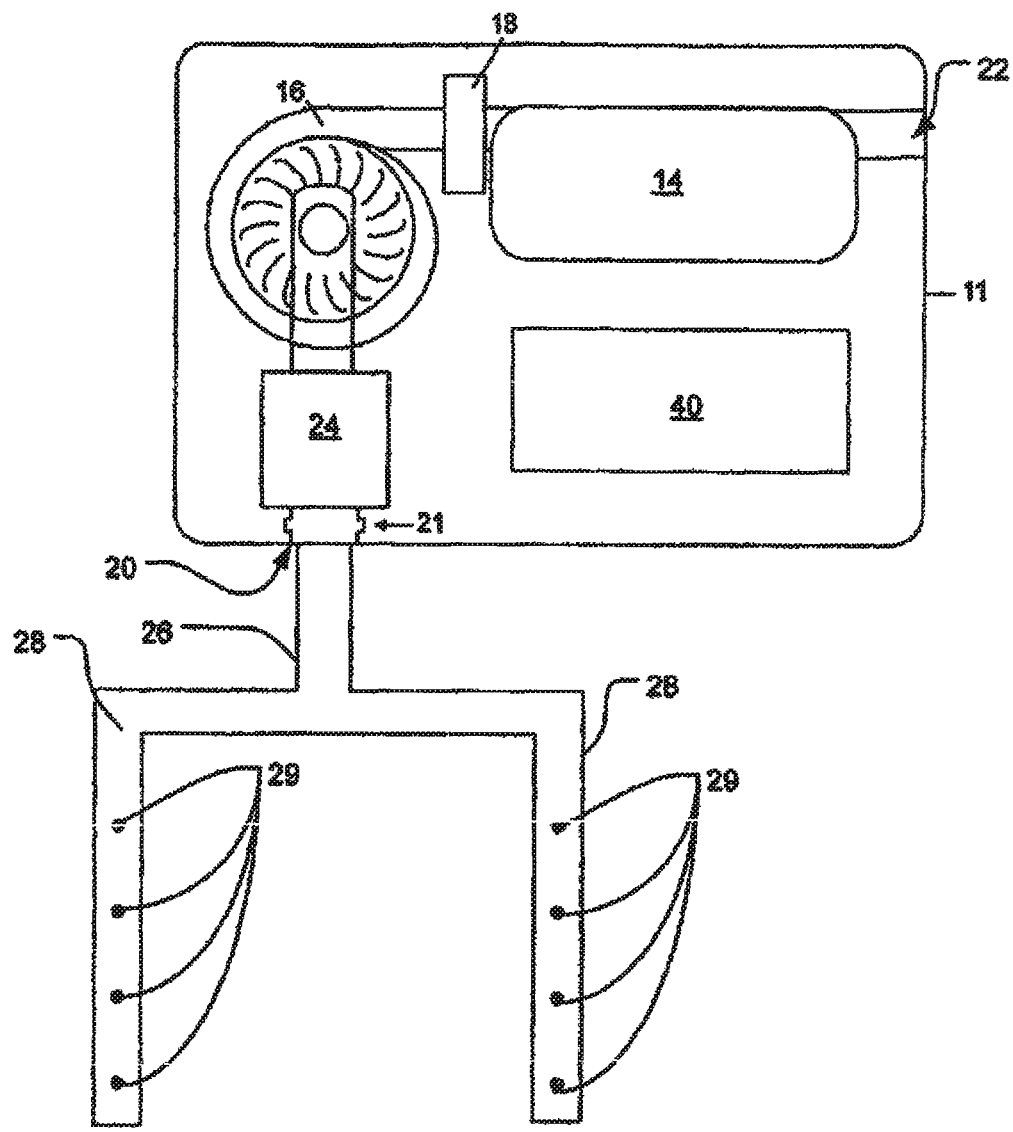
FIG. 1 shows a particle detection system including an air sampling network.

FIG. 1 shows a particle detection system including a particle detector 11 in fluid communication with a sampling network 28. The sampling network includes a plurality of inlets 29 through which air is drawn. An aspirator 16 draws air into the sampling network 28 through inlet 21 and along into a particle detection chamber 14. Air sample exits the detection system through outlet 22.

The detector includes a flow sensor 24. In a preferred embodiment of the present invention, an ultrasonic flow sensor as described in WO 2004/102499 is employed. This sensor enables volumetric flow measurements to be made. The flow sensor 24 provides an indication of the volume of air flowing into the particle detector 10 from the sampling network 28 per unit time. The output of the flow sensor 24 may be used to infer, for example, when flow faults e.g. a blockage of the sampling network 28 or reduced aspirator performance, has occurred.

The system 10 also includes a controller 40 for determining the level of particles in the air sample based on the detector's 14 output and apply alarm and fault logic to the detector output alert a user to the presence of particles and the operating state of the system. A typical installation of a Vesda or ICAM smoke detector, from Xtralis Pty Ltd. would be an example of a system of this type.

Such a detection system can be applied in an embodiment of the present invention to additionally determine the point of entry of particles into the air sampling network 28.

Figure 2:
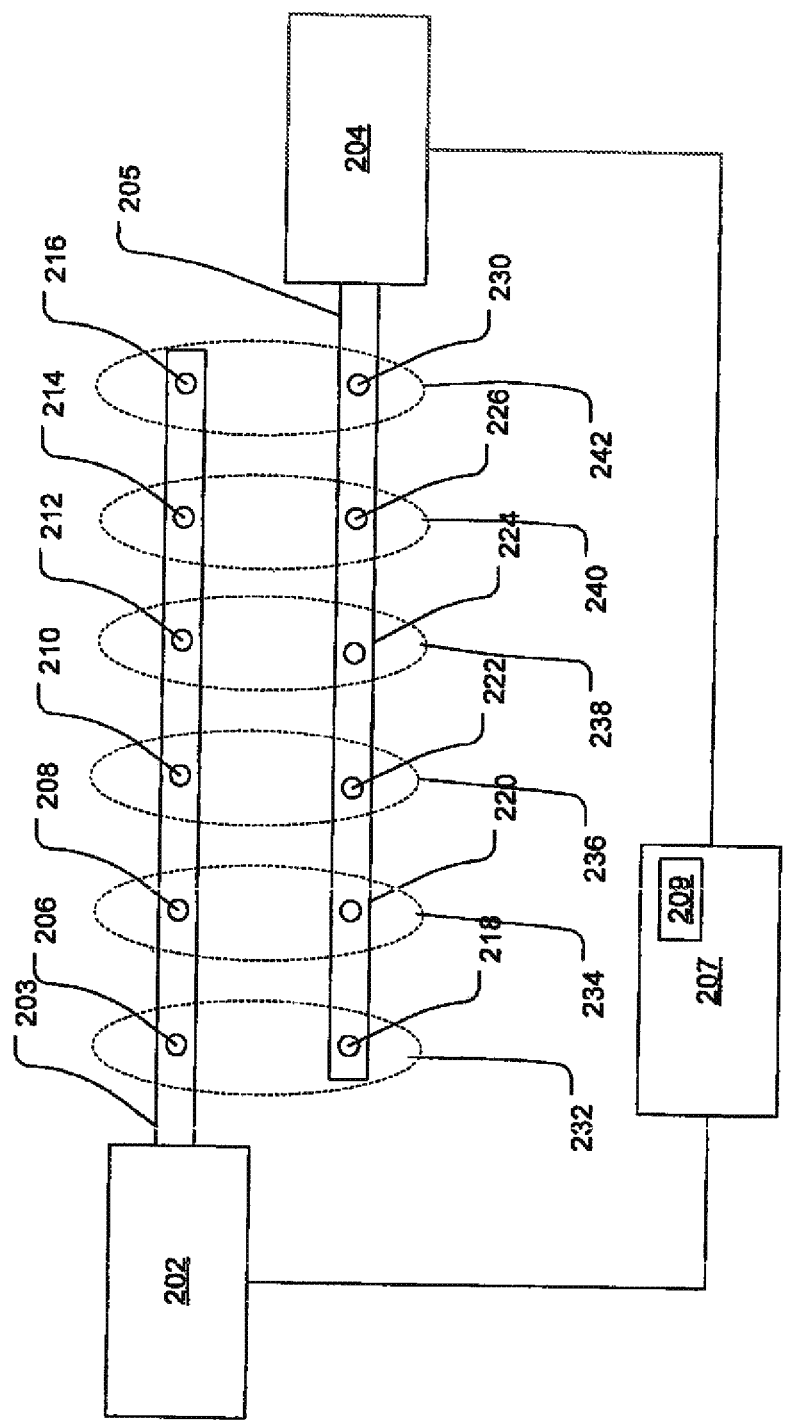
FIG. 2 shows a particle detection system employing two particle detectors to enable determination of the location at which smoke enters an air sampling network.

FIG. 2 shows two particle detectors 202 and 204, each particle detector being of the type illustrated in FIG. 1. Each detector is connected to a respective pipe of sampling network 203 and 205 respectively. The sampling networks 203 and 205 are effectively parallel and configured to monitor the same area. Each detector is also connected to a control unit 207, containing a microcontroller 209. Pipe 203 has a plurality of air inlets 206-216. Similarly, pipe 205 has a plurality of air inlets 218-230. Each air inlet from pipe 203 can be paired with an inlet from its parallel air pipe 205. At the time of installation, each inlet from pipe 203 is positioned to be close to a corresponding inlet from pipe 205. The inlets are therefore arranged in pairs. For example, air inlet 206 of pipe 203 and air inlet 218 of pipe 205 are together labelled air sampling inlet pair 232, because air inlet 206 and air inlet 218 are placed in close physical proximity. For example each pair of inlets may be located in the same room of a row of offices, or even be attached to a common sampling point.

In normal operation, the aspirator of particle detector 202 draws air pipe 203. The aspirator of particle detector 204 draws air through pipe 205. As each particle detector draws air, the scattered light or "smoke level" is measured, and reported to the control unit 207. The microcontroller 209 of the control unit 207 stores the reported smoke levels in its internal memory.

In the event that smoke enters the air sampling network at air sampling inlet pair 232, the distance that smoke must travel to reach particle detector 202 from air inlet 206 is much smaller than the distance that smoke must travel to reach particle detector 204 from air inlet 218. Accordingly, particle detector 202 will register an increased smoke level due to smoke entering air sampling inlet pair 232 before particle detector 204.

When the detected smoke level of one of the detectors 202,204, say particle detector 202, surpasses a predetermined threshold (which may also be an alarm threshold or not), the microcontroller begins to monitor the volume of air that has been drawn through one or both of the detectors. Because the smoke introduced at air inlet 218 must travel along the length of sampling pipe 205 before it can be detected at detector 204. After the particle detector 204 has drawn some volume of air, particle detector 204 will record an increased smoke level similar to that seen by particle detector 202. When this increased smoke level is recorded, the microcontroller 209 finishes monitoring the volume of air that has been drawn through detector 204. This final volume can be used to determine the sampling hole through which the smoke entered the air sampling pipe.

Because the flow sensor e.g. 24, outputs volumetric rate of flow, the volume of air passing through the detector is determined by integrating the output of the flow sensor over time. For example, the flow rate may be output one or more times per second by the sensor. These volumes can be accumulated either in the detector itself or at the microcontroller 209 to determine the total volume of sample air that has flowed.

The microcontroller 209 then uses the determined volume of air drawn by detector 204 to infer the sampling inlet pair through which the smoke particles were introduced. In one embodiment, the microcontroller achieves this by consulting a lookup table such as the one below:

| Volume | Air Inlet Pair |
|---|---|
| −5 L | Pair 1 |
| −3 L | Pair 2 |
| −1 L | Pair 3 |
| 1 L | Pair 4 |
| 3 L | Pair 5 |
| 5 L | Pair 6 |

The lookup table contains measured volumes mapped back to a corresponding sampling hole pair. Each volume corresponds to the volume of air that is drawn through the second detector before particles are detected by it. The negative and positive values indicate which detector of the pair 202 or 204 measure the volume. In this case a negative value indicates that the detector 202 measures volume.

For example, the microcontroller 209 may measure a volume of 112 mL of air drawn through detector 204 in the time between a smoke detection event by detector 202 and a subsequent detection event by detector 204. The row of the table that has a volume most closely corresponding to the volume is the fourth row, and corresponds to Pair 4. Pair 4, in turn, corresponds to air inlet pair 238. Had the measured volume instead been −112 mL, the closest table row would have been the entry for −100 mL, and Pair 3 (air inlet pair 236) would have been determined as the point at which smoke entered the system.

As will be appreciated, instead of measuring volume directly a value that corresponds to volume could be used in other embodiments of the present invention. For example the amount of air sample that has passed through the system can be determined by measuring a parameter other than volumetric flow rate, for example, if a mass flow sensor is present in the detector the output of such a sensor is able to be used in an embodiment of the present invention as it is related to volume by a correction factor that corrects for the temperature or density of the fluid.

Other physical parameters may also be used, including but not limited to as length, pressure or temperature or a count of volume-related events. For example, the time variable speed of the sample flow can be measured (e.g. in $ms^{-1}$) at location and accumulated (e.g. summing or integration etc.) to determine an amount of air that has passed through the system in the form of a "length". Volume could also be represent as a "length" by using the air sample (or known proportion of it) to displace a piston. The total displacement of the piston by the collected sample (or fixed proportion thereof) will represent a measure of the amount of air that has passed through the system, alternatively for a small cylinder size the a number of cycles of the piston could be counted to yield an numerical value corresponding to the volume of air sample that has passed through the system.

To give an example in which the physical parameter being used to determine an amount of air passing through the system is pressure or temperature, consider a system in which the air sample (or a known proportion of the air sample volume) is captured in a first chamber of a closed system, the actual volume $V_1$ (or pressure if volume if fixed) of this amount of air may never be known. However if the temperature $T_1$ and pressure $P_1$ (or volume if pressure is fixed) of the captured sample is measured. The captured sample is then moved to a second camber of known, volume $V_2$ and the new temperature $T_2$ and pressure $P_2$ are related to the initial volume by Boyle's law. By controlling one the either pressure or temperature to be held constant during the transfer of the sample (or sample portion) to the second chamber a temperature or pressure can be used as an amount that relates to volume of sample air that has passed through the system.

If a measurement of a value, such as mass, pressure, temperature and length, or other physical parameter that might be measured and which is tolerant to variable flow rate, is used in place of volume, the look-up table may alternatively map those other physical parameters directly to the air inlet pair number, without having to undertake the intermediate step of calculating the volume.

Once the air inlet pair number has been determined, the air inlet pair number can then be communicated to a secondary device, such as a Fire Alarm Control Panel (FRCP) or displayed to the user, to enable the localisation of the fire.

The lookup table can be created during the commissioning of the system, for example, by introducing smoke to each sample inlet pair and measuring the volume of air drawn before detection. As will be appreciated, if smoke has entered at sampling pair 232, there will be a very large volume of air drawn by detector 204 in the period after detection by detector 202 while detector 204 waits to detect the increased smoke level. Conversely, if smoke entered the system through sampling pair 242, detector 204 would detect an increased smoke level before detector 202, detector 202 drawing a very large volume of air while waiting to detect the increased smoke level. If smoke were to enter the sampling network toward the middle, for example at sample pair 236, although detector 202 would detect an increased smoke level first, the volume of air drawn before detection by detector 204 would be relatively smaller than in either of the first cases, since by the time of detection by detector 202, smoke will have already been drawn a substantial distance toward detector 204.

A person skilled in the art will appreciate that in the present configuration, where the sampling pipe network length is large, and transport time of particles through the sampling network is large, it will be possible to detect the presence of smoke before determining the location of smoke. For example, in the event that smoke is introduced at sampling inlet pair 232 of FIG. 2, smoke entering sampling hole 206 will quickly proceed to detector 202, and be detected. Detector 202 can immediately raise an alarm, despite the fact that smoke has not yet been detected by detector 204. Accordingly, where regulations prescribe the time by which smoke introduced to a sampling hole must be detected, this particular configuration is capable of detecting and reporting upon the presence of fire upon detection of smoke particles. Determination of the geographic location of the fire can then proceed in the manner previously described using a threshold level that is not an alarm level.

Accordingly, in a preferred form, the threshold used for determining an addressing event for each detector is higher than the lowest alarm (e.g.: a pre-alarm) threshold. A preferred embodiment waits until a higher level of particles is detected before attempting addressing.

In one embodiment, instead of employing a lookup table, the volume offset is multiplied by a constant to determine the distance along the sampling network at which smoke particles entered the system. In another embodiment, the volume offset is used as a variable in a function, which when evaluated, yields an estimate of the distance along the sampling network at which particles entered. In yet another embodiment, the volume offset is used as an index into a lookup table, the resulting lookup value being an estimate of the distance along the pipe. In preferred embodiments, the multiplicative constant, function, or lookup table described immediately above is determined at the time of commissioning by introducing smoke to each sampling hole pair and measuring the resulting volume offset to generate calibration data. As a person skilled in the art will appreciate, it may be possible to infer results for a subset of sampling holes by introducing smoke to another subset of holes, and relying upon the known distribution of sampling pairs in the sampling network.

As a person skilled in the art will appreciate, modifications of the invention can be adapted to determine, for example, the spread of a fire. The information reported by the system may be a distance along the sampling network at which particles appear to have entered, although this distance may not correspond to a sampling inlet pair.

The calculated distance or air inlet may be presented directly to an end user. The calculated distance or air inlet may also be communicated to another system, such as a fire alarm control panel (FACP). Where a fire alarm control panel has been designed to receive data from a system of addressable point detectors rather than a single aspirated smoke detector having multiple sampling points, the present system may communicate the calculated distance or inlet to the fire alarm control panel in a way which mimics a system of addressable point detectors, thereby utilising the FACPs understanding of geographic location of fires without actually utilising individual addressable point detectors.

Figure 3:
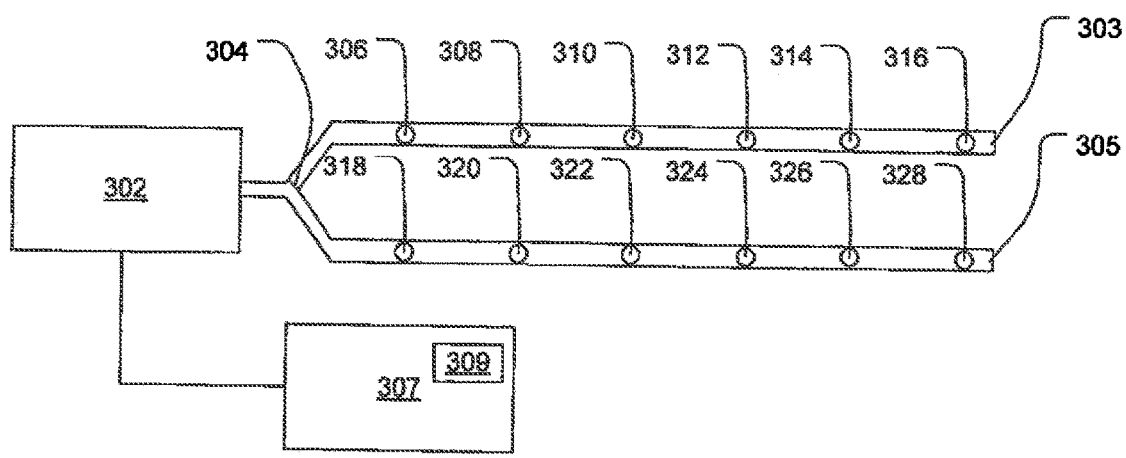
FIG. 3 shows a particle detection system employing a single particle detector coupled to an air sampling network having two branches separated by a valve.

FIG. 3 illustrates an alternative embodiment of the invention that employs a single particle detector attached to an air sampling network comprising two pipes 303 and 305 and a valve 304. In normal operation, air is drawn through pipe 303. When smoke detector 202 detects smoke above a predetermined threshold, valve 304 is moved to obstruct pipe 303, and to allow air to flow through pipe 305, and the microcontroller 309 begins to record the volume of air drawn through detector 302. When smoke particles are detected by detector 302, microcontroller 309 finishes recording the volume of air drawn though detector 302. The volume of air passing through air sampling network 305 and into particle detector 302 prior to again detecting particles is then used to infer the point at which smoke particles enter pipe 305, using any of the methods herein described.

Figure 4:
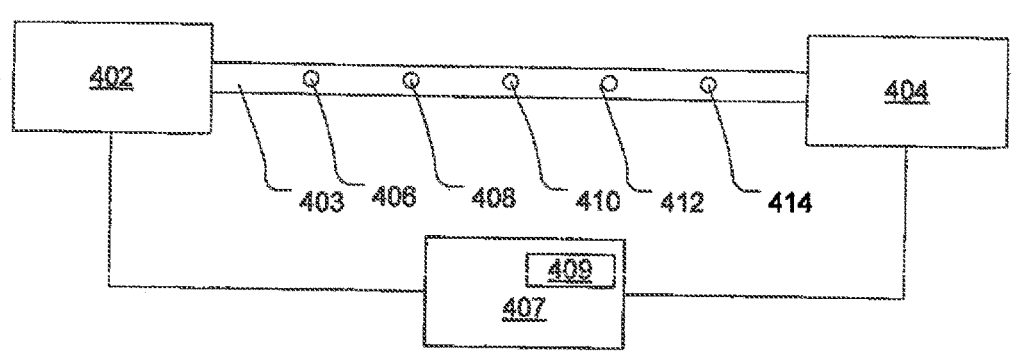
FIG. 4 shows a particle detection system employing two particle detectors coupled to a single air sampling pipeline.

FIG. 4 shows yet another approach which employs two particle detectors attached to a single air sampling network. Initially, smoke detector 402 operates and smoke detector 404 is inoperative. Smoke enters the system through air inlet 408. The smoke is drawn through the air sampling network, and detected by smoke detector 402. The determination of a smoke detection event triggers smoke detector 402 to become inoperative, smoke detector 404 to become operative, and microcontroller 409 to begin recording the volume of air drawn through detector 404. The aspirator of smoke detector 404 draws air along air sampling network 403 in a direction opposite to the initial flow direction caused by the aspirator of smoke detector 402. If smoke enters only through a single air inlet 408, smoke detector 404 cannot detect smoke until smoke from air inlet 408 reaches it. According to the present invention, the volume of air drawn by detector 404 after the initial detection by smoke detector 402 and up until subsequent detection of smoke by detector 404 is used to determine the air inlet through which smoke particles enter air sampling network 403, using any of the methods herein described.

The inventors have realised that it can be advantageous to use the volume of air drawn through the system or corresponding values to determine the point of entry of particles into the air sampling system. Moreover, by measuring volume rather than time, certain disadvantages or problems associated with reliance on measurement of time may be ameliorated. For example, it is known that with usage the sampling inlets gather dirt and get constricted, resulting in greater pressure drop and less flow of air. This means changing transport time for air samples over the life of the system. However the volume of air displaced to get a sample to the detector is relatively constant over time which makes the correlation between displacement volume and address more stable than transport time. Moreover if there are delays in opening a valve or beginning an aspirator, or the fan starts more slowly than expected the volume of air drawn through the system before particles are detected a second time is likely to be relatively unchanged, as compared to time based systems. Advantageously volume-based addressing systems may be able to be operated independent of the flow rate or over a range of variable flow speeds, enabling techniques such as those described below, in which the system opens up an end cap to speed up the flow of a sample to the detector.

Other types of flow sensor can be used in embodiments of the invention, for example a mass flow sensor, which provides an indication of the mass of air moving past the sensor over time. However, because mass flow sensors are insensitive to the density of the air they measure, other information such as the temperature of the air is required in order to determine the volume of the air moving past them.

A further difficulty that can arise in implementing embodiments of the above invention and that of the prior art is the potential difficulty in reliably determining that two equivalent smoke detection events has occurred, for example noise introduced prior to conversion of a signal from analogue to digital form may frustrate the process of determining when smoke is detected by detector 202, or detector 204. The inventors have devised an improved process that avoids or ameliorates this drawback.

A smoke detection system such as that of FIG. 2 produces two distinct data sets or "particle detection profiles". One data set is drawn from particle detector 202. The second data set is drawn from particle detector 204. Each data set contains a series of measured smoke levels. The data set may also contain information regarding the volume of air flowing through the detector, or a time at which a particle smoke level was measured.

In the following example, we will describe a system that monitors smoke levels over time. A person skilled in the art would appreciate that the method can be adapted to measuring smoke levels compared to the volume of air drawn by the system (as described above), however for illustrative purposes, we presently describe the system in relation to a series of measured smoke levels taken at various times.

FIG. 5 illustrates a particle detection profile. Detected smoke level is represented along its vertical axis. Time is measured along the horizontal axis. The smoke levels are those measured by detector 202 of FIG. 2. FIG. 6 shows a second particle detection profile. It is similar to that of FIG. 5, except that it relates to smoke levels measured by detector 204.

Comparing the figures, detector 202 detected a smoke level that reached a maximum at time 200, at which time it was deactivated and the particle detection output returned substantially to zero. Detector 204 detects a maximum smoke level at time 300. The different times are at least partially attributable to the additional distance along the sampling network 205 that smoke reaching detector 204 must travel. It would be possible to use the difference between the time of each maximum or the difference in time at which each profile crosses some predetermined threshold e.g. a smoke level of 150 on the vertical axis (which may be different to the alarm thresholds in use), to estimate the air inlet through which smoke entered the particle detection system. However, more preferably a cross correlation can be calculated using the data illustrated in FIG. 5 and FIG. 6.

For real and continuous functions $f$ and $g$, the cross-correlation is calculated according to the formula:

$$(f*g)(t) = \int_{-\infty}^{\infty} f(\tau) g(t+\tau) \cdot d\tau$$

A person skilled in the art will appreciate that this equation can be adapted for use with discrete measurements, such as the smoke levels detected in the present systems. For example, such a system can be implemented in hardware by temporarily storing a particle detection profile of each detector data in a respective buffer, e.g. a ring buffer. The buffers may be chosen so as to store data such that the longest possible offset measurable by the system can be accurately calculated. The cross correlation at a point can then be calculated by multiplying each pair of data elements in turn, and adding them, as described by the equation above. This process can then repeated for each possible offset t, to determine the overall cross-correlation function. The cross correlation function can then be used to estimate of the time offset between two particle detection events. This can in turn be used to infer through which inlet pair the particles entered the sampling pipe network. In some embodiments, information from the cross-correlation function is used to locate further geographic locations at which smoke may have entered the system.

In one embodiment, multiple peaks of the cross-correlation function are identified. A list of time offsets is calculated based upon the location of each peak and its corresponding cross-correlation value. The time offsets are used to infer the geographic location of the source of smoke. This can be used to potentially infer multiple locations at which fire occurs.

FIG. 7 illustrates a detector particle detection system 700 that includes a particle detector 702 in fluid communication with an air sampling network in the form of pipes 704, 706, 708 and 710. Each pipe includes a plurality of inlets, arranged into sampling inlet groups 712 to 740. Each sampling inlet group corresponds to a physical address, e.g.: a room or location that is serviced by the detector. Each sample inlet group includes between one and four air inlets.

The particle detector is connected to each pipe, and configured to provide an indication to a controller whether particles have been detected in fluid drawn through each pipe. The detector 702 could for example be four VESDA smoke detectors (from Xtralis Pty Ltd) detectors coupled to a central controller or a detector capable of independently detecting smoke on up to 4 pipes.

Each of sampling inlet groups 712 to 740 comprises one, two, three or four individual sampling inlets. The inlets are arranged into groups such that the same pattern does not occur twice. For example, sampling inlet group 730 includes an inlet on each pipe but no other group includes an inlet on each pipe. Sampling inlet group 712 includes an inlet only on pipe 710, but no other sampling inlet group includes only a hole on pipe 710. In the example of FIG. 7 the inlets are arranged in groups corresponding to a 4-bit Gray code.

Consistent with the discussion previously in relation to FIG. 2, at the time of installation, the inlets from each group are positioned close to one another. In the event that smoke enters the sampling network at a particular inlet, smoke should enter each of the pipes for which there is an inlet present in that group. For example, if smoke enters the sampling network near the location of sampling inlet group 730, one would expect smoke to enter each of the four pipes 704, 706, 708 and 710 at that location. Conversely, if smoke enters the sampling network at sampling inlet group 712, one would expect smoke to only enter pipe 710, since at that location, no other pipe includes an inlet. Upon detection of particles in the samples drawn into the individual pipes 704, 706, 708, 710, the particle detection system is able to determine the point of entry of smoke into the sampling network based upon the pattern of detection across the pipes 704, 706, 708, 710.

The table of FIG. 7 more completely illustrates the possible combinations of particle detection states across the four pipes and their corresponding particle detection locations. It is useful to begin by defining a nomenclature for expressing the indicated smoke levels. For present purposes, we will use a four binary bits to correspond to the detected smoke levels for each of pipes 704, 706, 708, and 710 respectively. For example, the indication '1111' corresponds to detection of smoke at some threshold level, in air drawn from each of pipes 704, 706, 708, and 710. The indication '1100' would refer to detection of smoke in air drawn from each of pipes 704 and 706. The indication '1010' would refer to detection of smoke in air drawn from each of pipes 704 and 708. Accordingly, each of these four bit indications can be treated as an address that corresponds to a location. There are fifteen non-zero four bit numbers. Accordingly, these fifteen numbers can be used to distinguish fifteen separate locations. The table of FIG. 7 lists each of the possible fifteen non-zero binary numbers in the column 'Gray Code' address. Alongside each binary number is one of 15 locations in the 'Location' column. The 'Smoke Detected' column shows whether smoke had been detected at the assigned threshold level at pipe.

There is a large number of possible ways of allocating addresses to each location. For example, in some embodiments, each successive location from 1 to 15 may take a subsequent binary number, in a manner similar to ordinary counting. Accordingly to this scheme, location 1 would have the address '0001' (which is a binary representation for the decimal number '1') and location 2 would have the address '0010' (which is a binary representation for the decimal number '2'). In this scheme, location 15 is given the binary address '1111', which is a binary representation for the decimal number 15.

However, the illustrated embodiment uses a different method of allocating addresses, called a 'Gray code'. In the illustrated gray code of FIG. 7, the location 1 is given the address '0001'. Location 2 is given the address '0011' (which corresponds to the binary for the decimal number '3'). Location 3 is given the address '0010' (which corresponds to the binary for the decimal number '2'). This sequence of numbering has a special property when each of the binary representations is considered. In particular, each pair of adjacent locations has a binary representation that differs by precisely one bit. For example, location 4 has the address '0110', whereas location 5 has the address '0111', and so only the fourth bit of each number differs. Similarly, location 11 has the address '1110' whereas location 12 has the address '1011', and so these also differ by their second bit only.

The way in which addresses are chosen may influence performance in the presence of detection errors. In particular use of a Gray code scheme may be, more robust to addressing errors than a straight "counting" address scheme in which successive locations are addressed by successive binary numbers. To illustrate this point, in a system that adopts the gray code numbering as described in FIG. 7, there is roughly a fifty percent chance that for a single bit error the determined location of the fire will be a location adjacent to the actual location of smoke, since the address of each adjacent location differs by a single bit only.

A person skilled in the art would appreciate that judicious selection of the sample inlet groups and increasing of the number of pipes feeding the detector can result in increased redundancy for the purpose of the localizing decision. In practical terms, the introduction of this redundancy may be such that, for example, simultaneous entry of smoke at multiple sample inlets can be distinguished, or alternatively, such a system may simply provide greater resilience to error.

FIGS. 8 and 9 show two embodiments of a further mechanism for providing addressability within an aspirated particle detection system of the type described in FIG. 1.

Turning firstly to FIG. 8, which shows a particle detection system 800, including a particle detector 11, coupled to an air sampling system 26. The air sampling system 26 includes a sampling pipe 28, including five sample points 29. As described in relation to FIG. 1, the aspirator of the particle detector 11 draws air samples in through the sample inlets 29, which then travel along the pipe 28 and into the detector 11 for analysis. In this embodiment, each sampling hole 29 additionally includes a valve 802. Each valve 802 is independently able to adjust flow through its respective sampling hole 29. The valves are controlled by the central controller of the detector 11, and are configured to be opened and closed under the control of detector 11. In some embodiments the valves 802 can receive sense the need to change state by interpreting glow changes as signals from the detector 11 in a manner described in more detail in connection with FIG. 28.

The purpose of the valves 802 on each sampling inlet 29 is to enable the smoke detector 11 to vary one of its systems' sampling parameters in order to assist in determining which of the sampling inlets 29 particles of interest have entered the system 800 through. Upon an initial detection of particles of interest by the detector 11, at a predetermined threshold level, the detection system 800 goes into the localisation routine. In this routine, the detector 11 causes the valves 29 to vary a sampling parameter, in this case flow rate, of air entering the sampling inlets. This variation may be performed on an inlet by inlet basis, or in groups of multiple inlets. After each variation in flow rate, a new particle concentration measurement is made. The initial particle concentration measurement and the second particle concentration measurement along with a variation parameter can then be used to determine which of the sample inlets particles of interest entered through.

This works because the particle level detected at the detector 11 is a weighted sum of particle concentrations and flow rates of the sample flow at each individual inlet 29. By varying the smoke level or flow rate through the sampling inlets, it is therefore possible to solve the set of simultaneous equations to determine the particle level entering any one sample inlet or group of inlets.

To illustrate a simple example, consider a smoke detection system including a smoke detector and a sampling network having a pipe with two sample inlets.

In this example, the level of smoke detected when all valves are open is given by the following equation:

$$DetectorSmokeAllValvesOpen = \frac{Smoke1 * flow1 + Smoke2 * flow2}{flow1 + flow2}$$

Where, DetectorSmokeAllValvesOpen is the total smoke detected by the smoke detector;
Smoke1 is the smoke level in the sample entering sample inlet 1;
flow1 is the flow rate of the sample entering through sample inlet 1;
Smoke2 is the smoke level entering the sample inlet 2; and
flow2 is the flow rate through sample inlet 2.

Now, when the first sample inlet is closed by its valve, the weighted sum of smoke arriving at the detector becomes:

$$DetectorSmokeValves1Closed = \frac{Smoke1 * 0 + Smoke2 * flow2}{0 + flow2}$$

It will be noted that this weighted sum is identical to equation 1, except that flow1=0, because the valve on sample inlet 1 has been closed fully.

We are now in a situation where we can solve these equations for Smoke1, to determine the amount of smoke that has entered through sample inlet 1, as follows:

$$Smoke1 = \frac{DetectorSmokeAllValvesOpen(flow1 + flow2) - DetectorSmokeValves1Closed(0 + flow2)}{flow1}$$

Thus, if we know flow1, flow2 and the change in flow, we can solve the equation and determine what smoke level entered at sample inlet 1. This principle also works in the event that the valves 802 only partially restrict flow through their respective sampling hole when they are closed, so long as it is possible to determine the flow rate at each sampling inlet 29. In order to allow flow rate to be detected, the system 800 includes a flow sensor 804 at each sample inlet 29. The flow sensor 804 could be a high sensitivity flow sensor, such as an ultrasonic flow sensor or a lower cost thermal flow sensor of the type which will be known to those skilled in the art.

In some embodiments, the valves 802 will not reduce the flow rate through their respective sample inlet to 0, but will only reduce it by some fraction. The following equation demonstrates how in a two hole system, as described in relation to the last example, smoke level through sample inlet 1 (Smoke1) may be calculated if valves are used to reduce the flow rate through their respective sampling holes to half their previous flow rate.

$$Smoke1 = \frac{DetectorSmokeAllValvesOpen(flow1 + flow2) - DetectorSmokeValves1Closed(0.5\ flow1 + flow2)}{0.5\ flow1}$$

In a further embodiment of the present invention, instead of varying flow rate through the sample inlet to solve the simultaneous equations, it is possible to vary the level of smoke entering each of the inlets. This can be achieved by selectively interposing a filter into the flow path through each of the sample inlets 29. An example of such a system is shown in FIGS. 9A & 9B. The system of FIG. 9A 900, includes a detector 11 connected to a sampling network 26, which includes sampling pipe 28, into which air samples are drawn through plurality of sample inlets 29. Each sample inlet additionally includes a selectable filter arrangement 902, which is shown in more detail in FIG. 9B. The selectable filter arrangement 902 presents an air sample inlet 904 (equivalent to inlet 29) at one end, and a sample outlet 906 at the other. The air sample inlet 904 is open to the environment, and allows an air sample from the environment to be drawn into the selectable filter arrangement 902. The sample outlet 906 is connected to the sampling pipe 28. Inside the selectable filter arrangement 902 are two flow paths, one path, 908, which is unfiltered, and another 910 which includes a filter 912. The selectable filter arrangement 902 additionally includes a valve 914. The valve 914 is moveable between the first position in which it blocks the filtered flow path 910, and a second position in which it blocks the unfiltered flow path 908. After smoke has initially been detected by the detector 11, at a threshold level, and the detector goes into its localisation mode, in which it attempts to determine which sample inlet 29 particles have entered the system from, the valve 914 is triggered to switch between the first position in which particles drawn in through the inlet 904 are allowed to pass through to the outlet 906, into a second position, in which any particles entering the inlet 904 are removed from the airflow passing out of the outlet 906 by the filter 912. In a preferred form, the filter 912 is a HEPA filter or other high efficiency filter which will remove substantially all particles from the airflow.

The sampling point 29, and in this case the selectable filter arrangement 902 includes a flow sensor 916 to measure flow rate entering the sampling point 29.

The selectable filter arrangement 902 can be configured to communicate with the detector 11 via the airflow path of the system 900. In an example such as this the communication protocol used by the detector 11 will need to signal such that each selectable filter arrangement 902 can be individually addressed or each selectable filter arrangement programmed to operate with a co-ordinated timing. More details of an example communication method are described in connection with FIG. 28.

As will be appreciated, a similar set of equations to that described in connection with the first example, can be applied to the system of the type illustrated in FIGS. 9A and 9B.

For a two hole system, as discussed above, the level of smoke arriving at the detector when all sample inlets have their input unfiltered can be expressed with the following equation:

$$DetectorSmokeAllUnfiltered = \frac{Smoke1 * flow1 + Smoke2 * flow2}{flow1 + flow2}$$

Where, DetectorSmokeAllUnfiltered is the level of smoke received at the detector when all flows are unfiltered, and all other terms are as described above in connection with equations 1 through 4.

After the selectable filter arrangement of the first sampling hole is moved into its filtered mode, the weighted sum expressing the level of smoke received at the detector is expressed as follows:

$$DetectorSmokeFiltered1 = \frac{0 * flow1 + Smoke2 * flow2}{flow1 + flow2}$$

Where, DetectorSmokeFiltered1 is the level of smoke received at the detector when the flow-through sample inlet 1 is fully filtered.

Solving these equations simultaneously yields the following equation, from which the level of smoke arriving at sample inlet 1 can be determined.

$$Smoke1 = \frac{DetectorSmokeAllUnfiltered(flow1 + flow2) - DetectorSmokeFiltered1(flow1 + flow2)}{flow1}$$

In order to handle increasing or decreasing smoke levels which may change reliability of this type of localisation process, the sequence of taking measurements in a first state and a second state can be repeated, and equivalent states averaged over a number of cycles. For example, the first measurement with all valves open can be taken followed by a smoke level measurement with the varied parameter, followed again by an equivalent initial reading with all valves open again. The two valve open measurements can then be averaged and used in subsequent calculations.

Further variation on the present systems can be implemented where instead of constricting or reducing the flow through each of the sampling points, the flow rate at the sampling points is increased, either by opening a valve, to increase the size of the sampling hole to decrease its flow impedance, and thereby increase the proportion of the total airflow from the system which is drawn through that sampling point, or by putting a fan at each sampling point and actuating or varying the speed of the fan to either increase or decrease the flow through the sampling point by a known amount.

The above embodiment has been described with a simple two inlet system. However, as will be appreciated, an as described in FIGS. 8 and 9A, systems are likely to have more than two sampling inlets. In such systems it is possible to scan through each of the inlets individually and vary the sampling parameter at only one inlet at a time. However, it may be beneficial to perform the variation in a grouped manner in which a subset of the total number of inlets have their sampling parameters adjusted in each measurement cycle. In some cases it may be possible to vary the sampling parameters of all sampling inlets by a differential amount in order to determine the contribution of each. As will be appreciated, the more inlets in the system that there are, the more times the process of varying sampling parameters and remeasuring particle concentration needs to be performed in order to collect sufficient data to solve the necessary set of equations.

The concept described in connection with FIGS. 8, 9A and 9B can be extended more generally to a method for detecting contaminant(s) in air samples drawn from a plurality of air intake paths and determining the contaminant level in each. For example the methods could be applied to an aspirating particle detector that is coupled with a sampling network having a plurality of air sampling pipes feeding to the single detector, where the contribution from each pipe or branch of the sampling system is to be determined. FIG. 7 describes a system in which this type of 'per pipe' localisation or addressing is used.

In the example of FIG. 7 the multi-pipe air sampling system may feed into a single contaminant detector such that it requires sampling of one pipe at a time, in order to determine which of the pipes has the contaminant in the air stream. This can be achieved by sealing all but one of the pipes and allowing a sample to enter the detector from one pipe at a time while the detector measures the contaminant level. This is repeated for each of the pipes in the multi-pipe air sampling network. The sealed pipe must be fully sealed against air flow in order to obtain accurate measures of the contaminant level in the open pipe. However, complete sealing is very difficult to achieve in low or reasonable cost valves. However by using a method similar to that described in connection FIGS. 8, 9A and 9B the requirement of complete sealing can be avoided.

FIG. 10A schematically illustrates a sensing system 1010 having and a sampling pipe network 1011 comprised of a total of two sampling pipes 1012, 1014. Each sampling pipe 1012, 1014 defines an air intake path therethrough. The air intake paths are combined at manifold 1016. The manifold 1016 may include suitable baffles to assist with combining the air flows. Air is drawn through the sensing system 1010 through the use of the fan 1018. A subsample from the combined air flows is drawn through detector loop 1020 in which a filter 1022 and a particle detector 1024 are provided. Once the air flow has passed through detector loop 1020, it rejoins the main air flow path 1019. A flow sensor 1026 may optionally be provided prior to the outlet 1028 of the system 1010. As will be appreciated the sensing system 1010 is equivalent to the detector 11 of FIG. 1.

Each of the sampling pipes 1012, 1014 has a valve such as a butterfly valve or another type of flow modifier 1030, 1032. Additionally, each sampling pipe 1012, 1014 includes an ultrasonic flow sensor 1013 and 1015.

It should be noted that, although the valves 1030, 1032, flow sensors 1013, 1015 and manifold 1016 are illustrated as forming part of the sampling network 1011, they may equally be physically located within the housing of the sensing system 1010 and thus form part of the sensing system 1010 without changing operation of the present invention.

A method according to the present invention will now be described in connection with FIGS. 10B to 10D. In normal operation, each valve 1030, 1032 is fully open as shown in FIG. 10B. However, when the particle detector 1024 detects the presence of a contaminant in the sampled air flows at a predetermined level, the scanning method according to the present invention is undertaken. Firstly, the first sampling pipe 1012 is partially closed as shown in FIG. 10C. In this condition, the particle detector 1024 takes a measure of the contaminant ($C_1$). Additionally, the flow rate is measured in the sampling pipes 1012, 1014 ($F_{mp}$, where F is the flow, m is the measurement number and p is the pipe number. Thus, the flow rate measurements will be $F_{11}$ and $F_{12}$) with flow sensors 1013 and 1015 respectively.

In the next step, the other sampling pipe 14 is partially blocked by moving the butterfly valve to the position illustrated in FIG. 10D. In this condition, the particle detector measures the contaminant level ($C_2$). Additionally, flow rate measurements are taken ($F_{21}$, $F_{22}$).

Assuming that the amount of contaminant (or relative amount of contaminant between pipes) is not changing significantly during the scanning period, the individual contaminant measurement for a pipe can be calculated from the following set of simultaneous equations:

$$C_1 = X_1 F_{11}/(F_{11}+F_{12}) + X_2 F_{12}/(F_{11}+F_{12})$$

$$C_2 = X_1 F_{21}/(F_{21}+F_{22}) + X_2 F_{22}/(F_{21}+F_{22})$$

where $X_1$ is the actual contamination in pipe 1 and $X_2$ is the actual contamination in pipe 2.

Advantageously, embodiments of the present invention enable cross-talk between the sample pipes, caused by imperfect sealing of the sample pipes, for a given species of contaminant to be eliminated without costly, precision valving. Instead, low-cost butterfly valves or other types of flow modifiers are sufficient to accurately eliminate the cross-talk, and allow pipe addressability to be achieved.

As noted above, the instead of using valves to partially close the pipes, a filter could be selectively interposed into the pipes to reduce the contaminant level in each pipe temporarily by a known amount (preferably to 0) and the method adjusted to solve for Contaminant level as described above for hole addressing.

In the various embodiments described herein, a common step which is performed, is an initial detection of particles at a detector and more particularly an attempt to accurately identify the receipt of the smoke from a particular sampling inlet of the sampling system. In particular, the event which is most commonly sought to be detected is an arrival of a smoke front that is propagating down sampling pipe, and which represents smoke which entered a particular sample inlet after a change in the operation in the sample network, e.g. opening or closing of valves or flushing the pipe network with clean fluid, or reversing flow direction or the like. FIGS. 11A and 11B illustrate this concept.

FIG. 11A illustrates a particle detection system 1100, which includes the detector 1102, and a sampling pipe network 1104. Sampling network 1104 has three sample inlets, 1106, 1108 and 1110. A smoke plume 1112 is located adjacent to sampling inlet 1108. Take for example a situation in which the direction of flow in the sampling network 1104 is reversed and the detector 1102 is attempting to determine the time of arrival of smoke entering the system from sampling hole 1108. A graph of determined smoke concentration against time is illustrated in FIG. 11B. Initially, for some period, 1020 low smoke level is detected as the sample fluid arriving at the detector only contains sample fluid from sample inlet 1106. At time T1, an increase in smoke is detected. Over the next time period 1022, when the sample from inlet 1108 begins arriving the detected smoke level ramps up until time T2, when approximate steady state level is detected. In the graph of FIG. 11B, the ramp-up 1022 is not due to an increase in smoke level, but due to a smearing or diffusion of the smoke front of sample entering sampling hole 1108. If the entry of particles from the environment into the sampling network was even and instantaneous, there would be a step change in the smoke level detected by the detector 1102, at T1 when the sample from hole 1108 arrives at the detector 11.

The present inventors believe that there are a range of factors contributing to the diffusion of the smoke front, representing the arrival of the sample portion that includes an air sample drawn through a particular one of the sample inlets of the sampling system. Chief amongst these is suspected to be the existence of a flow speed gradient across the cross-section of the air sampling duct. FIG. 11C illustrates a cross section through an air sampling duct 1130 such as pipe 1104. Arrows 1132 indicate that flow rate in the central portion of the duct 1130 is greater than the flow rate near the walls of the duct.

The belief is that it takes some amount of time for a sample being drawn in through a sample inlet, e.g. 1134 to break into the fast flowing central region of the flow in the duct 1130, and therefore the smoke front is smeared out when it arrives at the detector. This mechanism however has competing factors, namely initially a sample will be introduced into the slow flowing peripheral air within the duct which will delay its arrival at the detector. However over time part of the sample will find its way into the fast flowing central region which will minimise its transport time to the detector.

The inventors have proposed that a physical structure can be placed in the duct of the sampling network (i.e. in the pipe of the sampling network) to ameliorate this problem. In a first family of solutions, the inventors propose a sample injection inlet which extends inward from the wall 1131 of the pipe 1130, towards the centre 1133 of the pipe 1130, so as to deliver the sample in the faster flowing region of the sample flow. Three examples of such a sample injection inlet are shown in FIG. 12.

In FIG. 12, a duct forming part of an air sampling system in the form of pipe 1200 is illustrated. The pipe 1200 is defined by a wall 1202. Three sample injection inlets 1204, 1206 and 1208 are also illustrated. The first sample injection inlet 1204 is a short tube 1210, which extends from the side wall into the pipe 1200, towards its centre 12-12. Sample injection inlet 1206, is similar to inlet 1210 but terminates on its inside end 1214 with a Chamfered tip. The tip has the effect of functionally making the outlet 1216 point in a downstream direction with respect to the flow within the pipe.

Finally, sample injection inlet 1208 takes the form of an inverted L shaped tube 1220. Its inlet is external to the duct 1200, and its outlet 1222 faces in a downstream direction and is aligned with the centre of the duct 1200, thus injecting samples, drawn into the sample inlet 1208, at the centre of the pipe in the fastest flowing fluid flow. These three examples take advantage of the faster flowing central region of flow within the pipe to minimise smearing of samples drawn in through the sample inlet.

An alternative to this injection method is illustrated in 13A to 13D. This series of examples uses a structure which creates turbulence within the duct of the sampling system to prevent or disrupt laminar airflow within the sampling duct, to thereby minimise flow gradient of the type illustrated in FIG. 11C. FIGS. 13A to 13D each illustrate a segment of duct 1300, 1310, 13,20 and 1330 respectively.

Figure 13A:
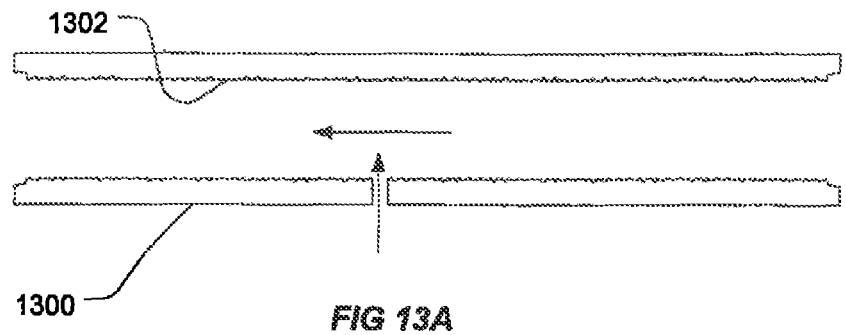

In FIG. 13A, the inside wall 1302 of the duct 1300 is used as a turbulator. The wall 1302 has been roughened or given surface contour or texture such as ribs, lines, bosses, or other, to create a rough surface that disrupts flow across it.

Figure 13B:
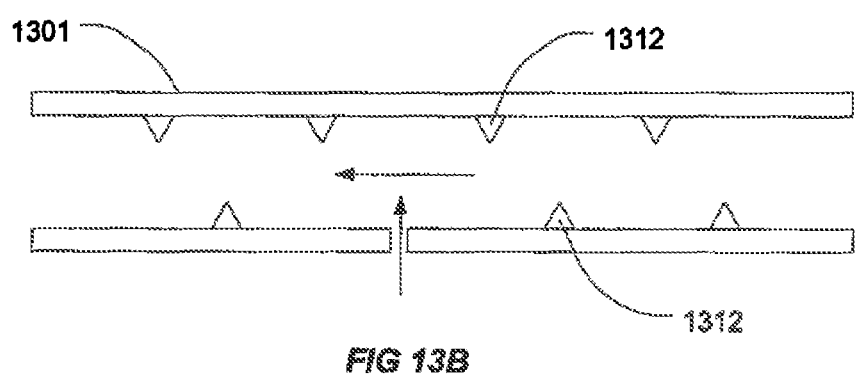

In FIG. 13B the turbulator is a series of turbulence causing protrusions 1312 extending inward from the wall 1310 of the pipe, and are used to caused disruption of laminar flow within the pipe 1310.

Figure 13C:
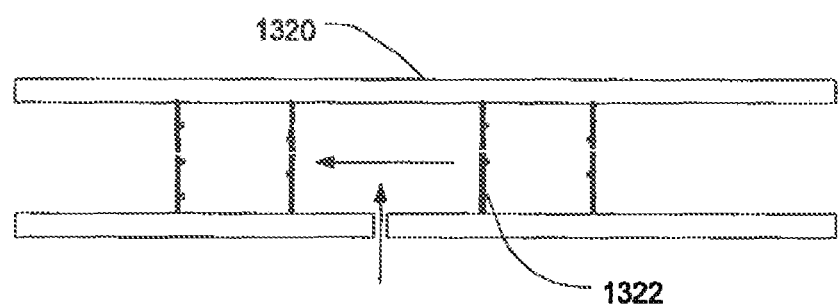

FIG. 13C illustrates an example in which a plurality of turbulence causing members extend the full breadth of the pipe 1320. In this example the turbulators are in the form of open mesh elements 1322. The open mesh elements 1322 have a hole size sufficiently large that they will tend not to clog over time but will cause turbulence to be created in the pipe 1320. As will be appreciated by those skilled in the art, a range of different shaped turbulators which span across the interior of a sampling duct can be devised.

Figure 13D:
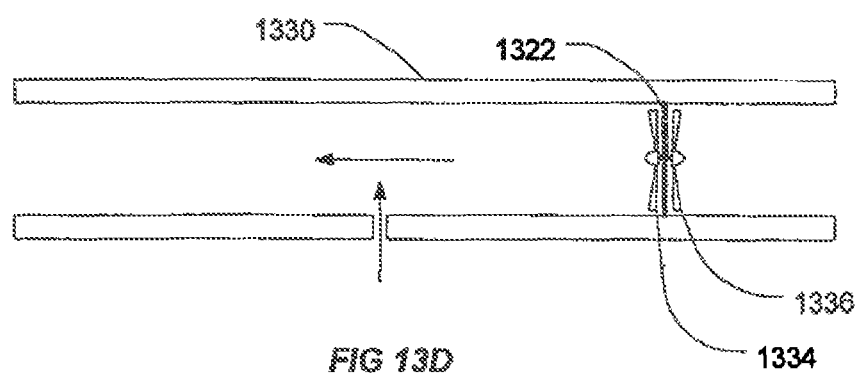

FIG. 13D illustrates a further example in which a moving turbulence causing element 1332 is placed inside the pipe 1330. In this case, a series of fans 1334 and 1336 are supported in the pipe 1330. The fans may be actively driven or passively rotating, but serve to stir the air or cause turbulence therein, as the air flows past them.

In this example, it has been convenient to describe the turbulence causing structure in a region of the duct which is an adjacent sampling inlet, however it should be noted that there is no particular reason why this should be done and the turbulence causing structure could be placed away from sampling inlets.

As will be appreciated with the four examples described above, the purpose of the turbulence causing structure is to break down the flow profile across the air sampling duct such that the air entering from a sampling inlet will travel along the sampling duct to the detector like a 'packet', rather than having part of it travel relatively faster or slower than another part and thereby smear out the arrival of the sample front at the detector.

Alternatively, or in addition to the techniques described above, the present inventors have identified that additional improvements in detecting which sample inlet of a plurality of sample inlets, smoke is received from by at least partially ameliorating the effect of dilution on air samples drawn into the sampling network. Consider a particle detection system such as that illustrated in FIG. 11A. In such a system, the air sample drawn into sampling pipe 1108 will be drawn into the sampling pipe 1104, where it mixes with, and is diluted by a sample drawn from sampling point 1110. Similarly, the air sample drawn from sample inlet 1106 is diluted by samples drawn from all up-stream sample inlets. Thus, by the time air samples arrive at the detector 1102, the actual concentration of particles which is detected will be greatly diluted compared to the sample concentration in the atmosphere surrounding the particular sampling inlet through which the particles entered the sampling network. The present inventors have determined that certain modifications to the systems described herein can be performed to ameliorate this problem, either by increasing the concentration of samples drawn into the sampling pipe, such that they more closely reflect the actual concentration of particles in the atmosphere surrounding this sampling point and/or by providing mechanisms for delivering samples to the detector with minimal additional dilution.

FIG. 14 illustrates a first exemplary system 1400 which implements such a technique. The system 1400 includes a detector 11, and an air sampling network 26 including a sampling pipe 28 having five sample inlets 29 at the far end 1402 of the air sampling pipe 28, the detector system 1400 includes a sample amplification arrangement in the form of bellows 1404, which are driven by an actuation means 1406. The bellows 1404 perform the function of blowing or sucking air along or from the sampling pipe network in a manner to be described below. As will be appreciated by those skilled in the art, a wide variety of systems could be used to replace the bellows structure, for example, a reciprocating pneumatic piston, or reversible fan or pump or other like air movement device could be used in place of the bellows 1404.

Operation of system 1400 will now be described. Initially, once particles at a threshold level have been detected by the detector 11, the system 1400 enters a localisation mode in which the location of particles in the system will be determined. In this mode, the primary air movement system, e.g. the aspirator 16 of the detector 11 is stopped and the system enters a sample amplification phase in which the controller communicates via communications channel 1408 with the actuation device 1406 of the bellows 1404. With the fan stopped, or alternatively with a valve at the detector end of the sampling network 26 closed, the sampling pipe 28 contains a fixed volume of air, in use the bellows 1404 is used to increase and decrease the volume of air contained within the sampling pipe network 26. When the bellows is expanded the volume increases and additional sample fluid is drawn into each of the sampling inlets 29. When the bellows is contracted some portion of the air within the sampling network 26 is expelled from the sampling inlets 29. By expanding and contracting the volume of air within the sampling pipe network, air is repeatedly pumped into and out of each of the sampling inlets creating a localised sample portion within the sampling pipe 28, surrounding each of the sampling inlets 29, which more closely reflect the level of particles of interest in the environment directly adjacent each of the sampling inlets 29, than would be the case with the continually drawn and continually diluted sample stream.

Consider the situation at a single one of the sampling inlets 29, the air sample drawn into the sampling inlet enters the sample pipe network and mixes with the existing flow within the pipe 28. The existing air flowing past the sampling inlet dilutes the sample with samples drawn from all upstream sampling inlets. When the flow in the pipe 28 is stopped by closing a valve 1410 at the detector end of the pipe 28 or possibly by stopping the aspirator of the detector 11, then the bellows 1404 are contracted and then, some portion of air within the sampling pipe 28 surrounding the sampling point 29 is expelled from the sampling point 29, as air is pushed along the sampling pipe 29 by the bellows. However, the air which is expelled from each sampling point includes the diluting samples from the upstream sampling points. Suction is again applied to the pipe network 28 by expanding the bellows 1404 and an additional air sample is drawn into each sampling point. Whilst this sample is also diluted by the fluid which already exists within the sampling pipe adjacent the sampling point, part of this diluting air is the air sample which was previously drawn into the sampling point of interest. Therefore, the total concentration after the second sampling is increased compared to the first. With repeated cycles of expelling and sampling via a sampling inlet, the proportion of air within the pipe 28 in a portion of the sample surrounding the sampling inlet begins to approach increases and the particle level begins to approach that in the atmosphere surrounding sampling inlet. Using this method, discrete sample portions within the sampling pipe 29 are formed which represent, more closely, the environment surrounding the sampling inlets. Because dilution is reduced, the methods described above which rely on detection of the onset of a smoke level increase i.e. a smoke front to determine the location of entry of particles along the sampling network can be improved. Once the sample amplification phase is completed the system enters a transportation phase and moves the sampled air, now including sample packets which are relatively localised, back to the detector for analysis.

FIGS. 14A to 14E illustrate an exemplary system that uses a vibrating membrane, e.g. a speaker to perform sample amplification. The system 1420 includes a particle detector 11 coupled to an air sampling network 26. The air sampling network 26 includes a sampling pipe 28 having a plurality of air sample inlets 29. The air sampling network is coupled to the detector via a sample amplification arrangement 1422 and aspirator 1424. The aspirator 1424 operates to draw samples into the sampling network and push them to the detector 11 for analysis in a manner that will be described in more detail bellow. The sample amplification arrangement 1422 performs a similar job to the bellows of FIG. 14 in that it causes oscillation of the flow direction in the air sample system to promote mixing of air in the region of surrounding each sample inlet 29 and air in the sampling pipe 28. In this example the sample amplification arrangement 1422 includes a membrane 1426 that is mounted within a housing 1428 and driven back and forth in reciprocating motion by an actuator. The actuator and membrane can be provided by a loudspeaker. Preferably the membrane is made to oscillate at a subsonic frequency, and most preferably at between 2 and 10 Hz.

Figure 14A:
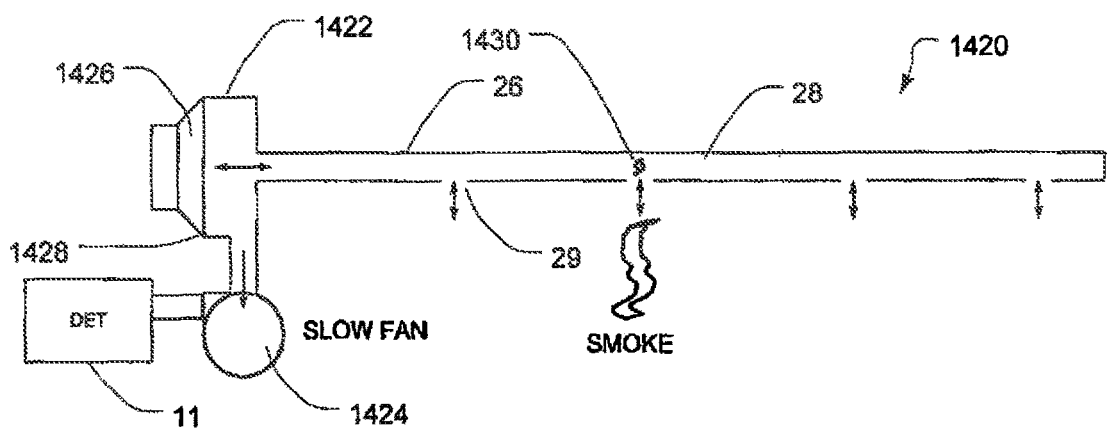
Figure 14B:
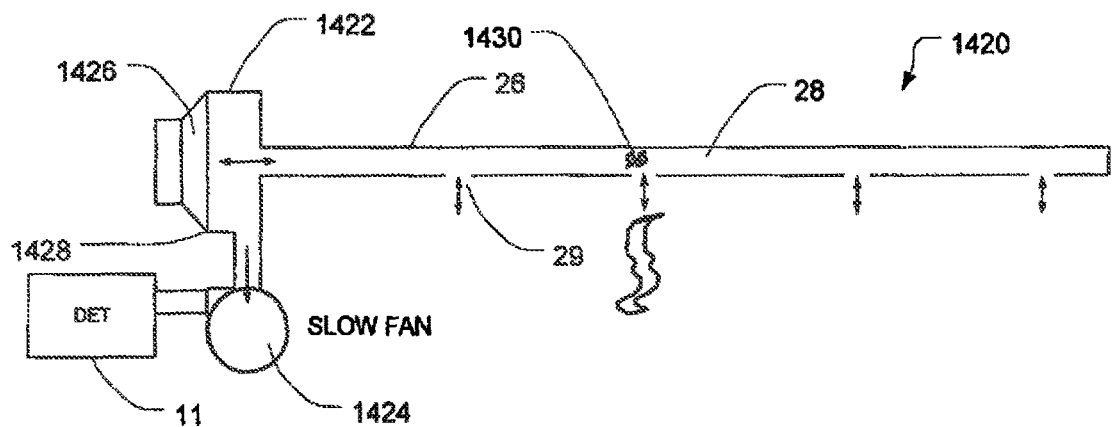
Figure 14C:
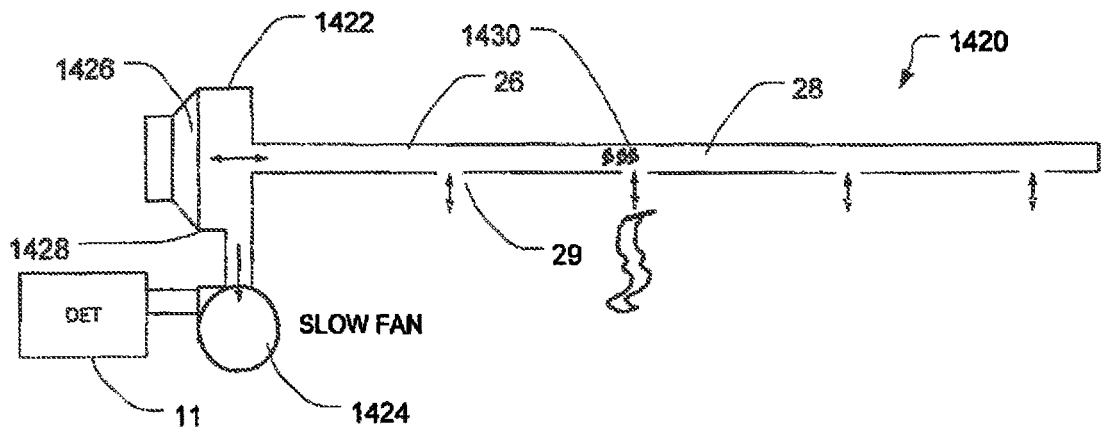
Figure 14D:
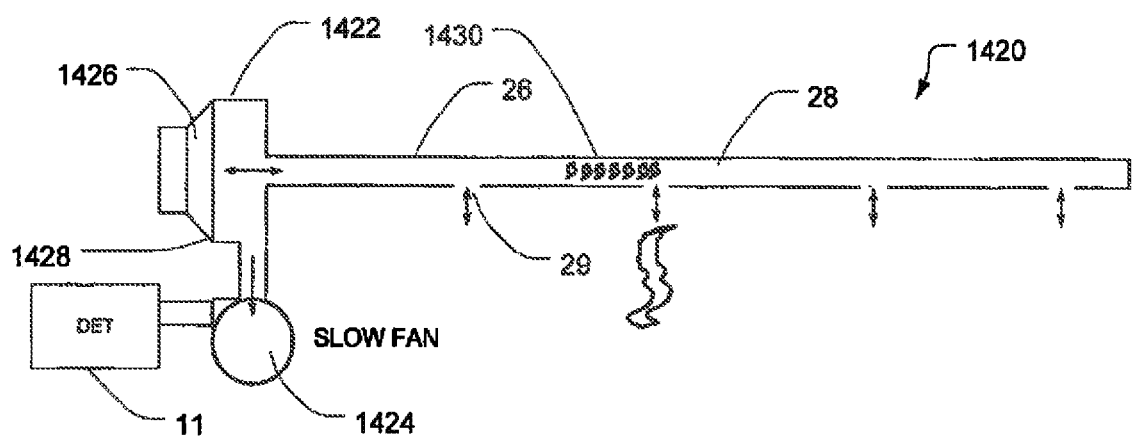

In ordinary operation the aspirator 1424 runs at a first speed setting that is sufficient meet sample transport time requirements and draws air samples to the detector 11. Once particles are detected in the sample flow, the system 1420 enters a localisation mode beginning with a sample amplification phase. In this phase, illustrated in FIG. 14A, the fan enters a low speed operation and the sample amplification arrangement 1422 is activated. The membrane 1426 oscillates and agitates the air in the pipe 28 to cause mixing with air nearby the entrance to each sample inlet 29. Because the fan is running at low speed, a mixed air sample that more closely approaches the true particle concentration in the air surrounding the sampling network 26 enters each sampling inlet 29 and slowly builds a packet of air downstream of each inlet. In FIGS. 14B to 14D the agitation is continued as the fan 1424 runs slowly and builds the sample packet 1430.

Figure 14E:
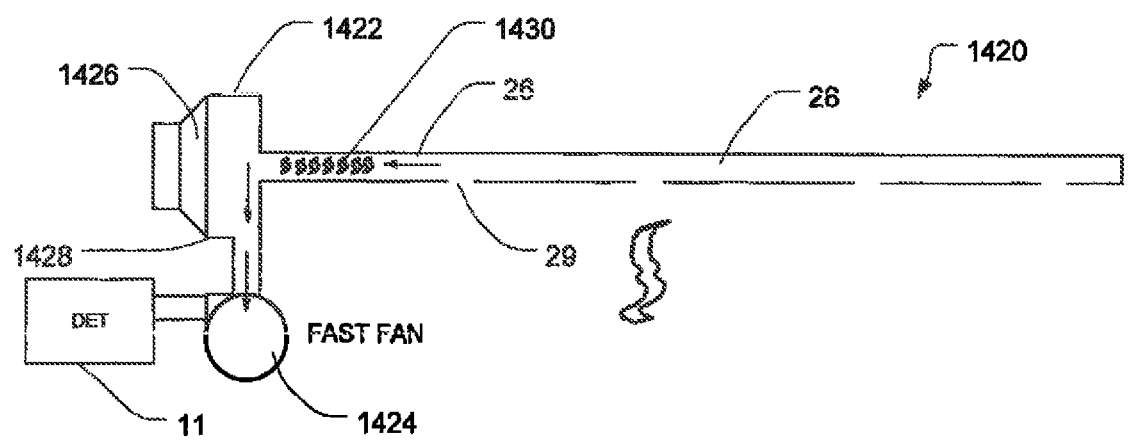

Next in FIG. 14E, the system 10 enters transportation phase. In this mode the fan 1424 increases speed, and the membrane 1426 is stopped. The sample packets, e.g. 1430 are then drawn back to the detector 12 with the fan running in fast mode. As described below, various techniques (e.g. by blocking sampling inlets, opening the end of the pipe etc.) can be employed to minimise mixing or smearing of the sample packets to thereby increase the reliability of the localisation techniques applied. FIG. 15 illustrates a second embodiment of a system 1500 which performs a similar method to that described in connection to FIG. 14.

In FIG. 15 like features have been like numbered with respect to FIG. 14 and the earlier embodiments and for brevity will not be re-explained. In this example, the sampling network 26, at its distal end 1502 includes a fan 1504, and a valve 1506. Optionally at the end 1508 of the sampling pipe 28 which is closest to the detector 11, there may additionally be a second valve 1510. In this example, the valve 1506 is normally closed while valve 1510 is open during ordinary operation of the detector 11. Once the detector goes into its localisation mode however, the position of the valves 1510 and 1506 is changed and valve 1510 is closed and valve 1506 is opened. The fan 1504 is then used to perform the same function as the bellows 1404 of FIG. 14. In this regard the fan 1504 is used to either blow some of the contents of the sampling pipe 26 from the sampling points 29, or suck samples in through the sampling points 29 as described above. As will be appreciated, this oscillation of between sucking and blowing samples can be performed by the primary aspirator of the particle detector 11. However, by putting the fan 1504 at the far end of the sampling pipe network 28, an additional advantage can be gained, namely that the fan 1504 can be used at the end of this process to push the contents of the sampling pipe 126 to the detector 11, rather than using the aspirator of the detector 11 to suck air samples down the sampling pipe 28. The advantage of using a blower fan 1504 at the end of the pipe 28 is that the sampling pipe 28 becomes positively pressurised and thus during the transportation phase does not draw any additional air samples from the environment surrounding the sampling points 29. In this way, a relatively undiluted column of sampling air containing packets/portions of sample air corresponding to each sampling inlet 29 is delivered to the detector 11 such that the 'packets' of sample which were formed by the oscillation process can be distinctly detected by the detector 11. As will be further appreciated the oscillation of between sucking and blowing samples during sample amplification can be performed by using the primary aspirator of the particle detector 11 and the fan 1504 operating in concert. For example, both fans may be set to operate synchronously, i.e. moving air in one direction and then the other to enhance localised mixing of samples around their respective sampling holes, or alternatively the fans can be set to alternately apply suction to their respective ends of pipe 26 to draw the sample fluid along the pipe in one direction. Thus rather than using the bellow-like push/pull on the sample flow from one end of the pipe 26 an alternating pull/pull mechanism from two ends of the pipe is used. At the non-pulling end a valve can be closed (or partially closed) to control the amount of sample flow entering the pipe's 26 end. Advantageously this mechanism allows the system to increase the concentrating effect of bellows action. It also allows the sample packet to be formed on both upstream and downstream of the sample inlet position. The increased concentrating effect also enables the system to cut down on the number of flow oscillation cycles for any given concentration increase or mixing increase, relative to a system that acts at one end. This scheme may also average out (and possibly neutralise) the effect that fires closer to the detector end up with a higher slug concentration. As will be described below in connection with FIGS. 18 and 19 a double ended flow modulation can be advantageously used to selectively perform sample amplification.

The system of FIG. 15 can be further modified as illustrated in FIG. 15B. In this example the particle detection system 1350 includes an air sampling system similar to that of FIG. 15 and similar features have been like numbered. However this system 1520 additionally includes two branch pipes 1522 and 1524 which enable additional modes of operation. The first branch 1522 is located at the downstream end of the pipe network, ideally between the entry to the detector 11 and the nearest sampling point 29. The branch pipe 1522 includes:

A fan 1526, which can be used to purge the sampling system in a manner to be described.

A filter 1528, which may inter alia be a HEPA filter or the like, which is used to clean the purging air delivered by the fan 1526.

A valve 1530 for selectively opening and closing the branch 1522 as needed.

The second branch pipe 1524 includes a valve 1532, and is used as an exhaust from the sampling pipe 28 during purging, as will be described below.

The system 1520 operates the in the same way as the system 1500 of FIG. 15 in detection mode, namely with the main aspirator of the detector 11 acting to draw air samples through the sampling inlets 29, along the sampling pipe 28 to the detector 11 for analysis. In detection mode the valves 1530, 1532 and 1502 are closed to prevent the air which is not associated with a sampling inlet 29 from being drawn into the system and diluting the air samples. Valves 1510 is open.

Once particles are detected to a sufficient extent, the system 1520 goes into localisation mode and the following steps occur:

Valve 1510 is closed and the fan of the main detector 11 stops drawing air down the sampling pipe 28.

Valves 1530 and 1532 (and possibly also 1502) are opened to enable purging of the sample air from the sampling pipe 28.

The fan 1526 is activated, and air is drawn into the branch 1522, through the filter 1528, where it is cleaned and into the sampling pipe 28. This clean air purges the pipe 28 of particle laden air and displaces it with clean air.

Valves 1530, 1532 and 1502 are closed and valve 1510 is opened and the main detector 11 fan is used to draw new air samples into the sampling inlets 29. This process only operates for a short period of time, say between 5 and 20 seconds, or as long as possible so as to avoid mixing of air samples that are drawn into adjacent sampling inlets 29. In this way packets of particle laden air are built up in the pipe 28. As will be appreciated this step could be augmented by performing one of the various concentrating techniques described herein, but in this embodiment sufficient sensitivity might be achieved without this added complication. As noted above, the use of the pusher fan 1504 also aids in delivering a relatively undiluted column of sampling air to the detector 11, which may obviate the need for an amplification stage in some embodiments.

The detector then moves into a transportation phase in which the main detector's 11 aspirator is then deactivated and valve 1502 opened. Valve 1510 remains open.

The pusher fan 1504 is activated and the packets of sample air are pushed down the pipe 28 for analysis.

The air samples are then analysed and the presence of particles versus volume (or other techniques) is used to determine through which inlet 29, the particles entered the system. In this example, analysis of the sample air in the localisation phase is performed by second particle detector 1534. This detector has a relatively fast response compared to that of detector 11.

This detector 1534 may not be as sensitive or stable in its output as detector 11, but as the particle level is likely to have increased (e.g. because of an increase in fire activity) as the localisation process is taking place, speed of detection may be a priority over sensitivity or accuracy. Furthermore actual particle concentration data can still be obtained by the main particle detector 11 as the air samples can pass through both detectors in series.

The main detector 11 and high speed detector 1534 may be part of the same particle detector (e.g. two particle detection chambers in a single device) or may be different devices, e.g. located in series. Furthermore the main detector 11 may be used alone. In this case the main detector could optionally be configured to operate in a high speed mode in which it has an improved response rate compared to its ordinary detection mode. This could be achieved by temporarily changing software parameters of the detector 11 e.g. reducing periods over which particle concentration levels are averaged etc. or by activating a second data processing path which receives detection chamber output data (or similar) and which is optimised for response rate.

As will be apparent from the foregoing the branches 1522 and 1524 and their respective components, and the fast response detector 1534, are optional additions to the system 1500 of FIG. 15. In order to implement the foregoing method all that is really needed over and above the system 1500 of FIG. 15 is a mechanism for delivering purging air to the pipe network 26 and a mechanism for controlling the system's valves to enter and exit the purge mode.

FIG. 16 illustrates a further example of a system implementing the oscillation method and a mechanism for reduced dilution of delivery of final, increased concentration, air samples to the detector. The system 1600 includes a detector 11, and sampling pipe network 26, as described in connection with FIGS. 14 and 15, and similar features have been labelled with the same reference numerals. In this example, the process of oscillating between sucking and blowing samples is performed by the primary aspirator of the detector 11. The sampling network 26 is additionally provided with a valve 1602 located upstream of the final sampling inlet 29. After sample concentration has been increased, as described above, using the main aspirator of the detector 11, the valve 1602, which is coupled to the controller of the detector 11 by communications channel 1604, is opened. The valve 1602 is configured to open the end of the sampling network to the atmosphere such that it approximates an open pipe which has substantially less flow impedance than any one of the sampling inlets 29. When the aspirator of the detector 11 then applies suction to the sampling network 26, drawing air is preferentially drawn into the end of the sampling pipe 28, and the sample packets already within the pipe 28 are drawn along to the detector 11. Because the open pipe end has low flow impedance, the level of air drawn into each of the sampling inlets 29 is greatly reduced, thus greatly reducing dilution of the samples as they are delivered to the detector 11. The reduced tendency for air to be drawn into the sampling inlets 29, when the valve 1602 is opened will also reduce the modification of the sample packets by smoke in the environment at or near the location of other sampling holes. The reduced flow into the sampling holes 29 when the valve 1602 is open will also make the calculation of the smoke source position less dependent on the flow at the sampling holes. As described above, the system is initially trained to determine which hole a sample packet has arrived from based on how much air is drawn through the sampling network once the localisation phase has been entered. However, because the sampling holes may block in a variable way over time the reliability of volume or time measurements based on the initial training may vary over time. By opening the valve 1602 the sample inlets 29 become less influential in the flow in the sampling pipe 28 and consequently the effect of differential blocking of the sampling inlets 29 over system life will be reduced. Finally opening the valve 1602 will reduce flow impedance and the transportation phase faster. e.g. 40 sec for a 100 m pipe at 50 L/min rather than 110 sec with the end of the pipe closed.

In some embodiments the valve 1602 of sampling network 28 beyond the last sampling inlet 29 can be provide with a filter, e.g. a HEPA filter through which air is drawn. This assists the sample packet from the last sample inlet 29 in standing out from the air being drawn into the end of the pipe which might also contain particles or interest or even dust. Such a HEPA filter could also be used in conjunction with a pusher fan to implement a purging phase similar to that described in connection with FIG. 15B, by suitable operation of the valves 1602 and fans of the system.

As will be appreciated in the examples given herein, valves could additionally be applied to each of the sampling inlets 29 to further facilitate the effect of the flow control mechanisms (e.g. bellow, fan, valve and equivalent structures) applied to the end of the pipe. For example, each of the sampling inlets 29 can be provided with a valve which is controlled in concert with the pipe end flow control system to optimise its performance.

FIGS. 20A and 20B illustrate two embodiments of the present invention, which may offer a particularly convenient set up compared to some of the embodiments illustrated above. These embodiments can be used in a manner equivalent to the systems of FIGS. 14 and 15 respectively, and like features have been like numbered.

The system 2010 of FIG. 20A differs from the embodiment of FIG. 14 in that the air sampling pipe 28 is provided with a return portion 2002 connected to the upstream end of sampling pipe portion 2012. This brings the far end 1402 of the sampling network 26 back to a location near to the detector 11. In this example, the bellows 1404 and its associated actuation means 1406 along with valve 1510 are mounted together in a common module 2004. Most preferably module can be connected mechanically and electrically to the detector 11. In a similar fashion, the system 2000 of FIG. 20B differs from the embodiment of FIG. 15 in that the air sampling pipe 28 is provided with a return pipe portion 2002 connected to the upstream end of sampling pipe portion 2012. The far end 1502 of the sampling network 26 is thus located near to the detector 11 such that the fan 1504 and with valves 1506 and 1510 can be mounted together in a common module 2004.

A localisation module (e.g. module 2004) can be used to implement any embodiments of the present inventions described herein in a convenient manner. Such modules could be retrofitted to detector systems not originally intended to perform localisation or provided as optional add-on modules so that purchasers of new equipment can be provided with a choice as to whether or not to buy a detector with these features. For example a module could be provided which implements the system of FIG. 15B by housing the following equipment:
the branch 1524 with vales 1532,
valve 1506 and pusher fan 1504
branch 1522 with its fan 1526, 1528 and valve 1530 along with valve 1510.

Similarly the valve 1602 and possibly also a HEPA filter could be housed in a similar module.

Whilst these embodiments require an extra length of pipe for the pipe network to loop back to near the detector 11, they offer the advantage that power and electrical communications lines do not need to be run to a position remote from the detector 11 to power and control the components of the system mounted to the upstream end 1402/1502 of the sampling pipe network 26, This may assist in making system installation more straightforward. Moreover it facilitates commissioning and testing since the most complex components are now located at a single location.

In the various embodiments illustrated in FIGS. 8, 9a and 9b, 14 through to 20b. Various components of the systems described are required to communicate with the detector 11 or other control component of the particle detection system illustrated. In the previously described embodiments communication takes place usually over a hard wired communications channel, or optionally via a wireless (e.g. radio) communication channel, for example communications link 1408 in FIG. 14). The present inventors have realised that a hard wired communication path need not be present but that the airflow path through the detection system could be used for communication between the detector or other controlling entity and another component or accessory of the system.

In most embodiments, the accessory will comprise a flow control device such as a valve, fan, filter or other element of the system that takes part in performing localisation technique described herein for example the accessory could include the valve 1502 and/or fan 1504 as used in the example of FIG. 15. Details of an exemplary accessory, in the form of a valve, are illustrated in FIG. 28.

The accessory 2800 is mounted to a portion of a sampling pipe 28 and has access to the airflow path 2802 contained within the sampling pipe 28. The accessory 2800 includes one or more sensors 2804 which are used to sense the condition in the airflow path 2802, such as flow speed, direction and/or pressure. The sensors 2804 are connected to controller 2806 and pass output signals indicative of their sensed condition to it. The controller 2806 receives sensor signals and processes these, and in turn controls the operation of the accessory as required.

In the present example the accessory 2800 includes a valve 2808 which may be selectively opened and closed under control of the controller 2806. The accessory 2800 is preferably powered by a battery 2810, rather than by hard wired power connection (although this is possible) in order to minimise wiring and installation requirements for the accessory.

In use, sensors 2804 are used by the accessory 2800 to sense the present state of the primary particle detector by receiving and detecting changes in airflow in the air sampling pipe 28. The controller 2806 interprets changes in the air flow 2802 as a communication from the detection system, and in response determines what action it should be taking at for the present instant. For example, in the localisation techniques described herein, the localisation phase may be begun by temporarily shutting down, slowing or changing direction of the main aspirator of the detector 11 or by changing the condition of one or more valves at the detector end of the system. This in turn causes the air flow 2802 in the sampling pipe 28 to change. The variation in air flow is sensed by the sensors 2804 as a changing air flow speed and pressure in the pipe 28. The change is interpreted by the controller 2806 to be a control signal from the detector 11 to take an appropriate control step in response to the sensed change in flow pattern. For example, detecting a cease in airflow 2802 may signal to the controller 2806 that the detection system has gone into a localisation mode and that the valve 2808 should be opened. Alternatively, more complex operations may be performed upon detection of a control signal through the air flow path 2802. For example, when the accessory 2800 senses that the system had entered localisation mode, the accessory enters its localisation mode in which a localisation routine is performed. This may involve the accessory operating in a first condition for first time period and then in second condition for a second time period and so on. To give a more concrete example, the valve 2802 may be controlled to remain closed for a predetermined period of time, say one minute while the other elements of the particle detection system perform a sample amplification routine. After the predetermined time elapses the controller may cause the valve 2808 to open in order for the detector to operate in a "transportation phase" of the localisation process to enable the delivery of concentrated sample "packets" back to the detector 11 for analysis.

As would be appreciated, if the localisation process includes an oscillation in flow in order to perform sample amplification, the sensors 2804 can sense the oscillation and the controller can respond to this to ensure that the valve or other flow control structure of the like is set in its appropriate operating condition.

Patterns of temporal changes in airflow can also be created by the detection system to encode control messages for an accessory, or to allow addressing of particular accessories in systems with multiple accessories that require independent control (e.g. the valves 802, 902 in FIGS. 8 and 9A)

This principle of operation to be extended to use the air flow path within the air sampling system 26 of a detector system to communicate in other ways such as by the application of sound pulses or the like. Clearly in such embodiments sensors in the form of suitable acoustic transducers would be needed in the accessory to sense these communication signals.

FIG. 29 illustrates a particle detection system 2900 including a particle detector 11, a localisation module 2004 and sampling pipe network 26 and an accessory 2902 similar to that described in connection with FIG. 28. The sampling pipe network 26 includes a sampling pipe 28 having a series of sampling inlets 29 spaced along its length. The localisation module includes 2004 includes a reciprocating piston 2904 which acts as a sample amplification arrangement in the localisation process.

The accessory 2900 in this example includes a fan 2908 and a valve 2910 which are controlled by a controller of the accessory in response to the accessory's sensors (being a flow sensor and pressure sensor, that are not shown) detecting signals in the sampling pipe 28 that indicate the state of the system.

In ordinary detection mode the accessory has its valve 2910 closed so that samples are drawn through the sample inlets 29. When the detector 11 detects particles at a predetermined level it enters a localisation mode. This initially involves a purge phase in which the main aspirator is reversed and air blown out of the sampling pipe 28. This causes an increase in pressure in the (previously slightly negatively pressurised) sampling pipe. The sensors of the accessory 2900 detect this and it interpreted by the accessory's controller as a signal that localisation mode has been activated. The controller then opens the valve and allows air to be purged out through the end of the pipe 28 to atmosphere instead of out through the sample inlets.

When this flow ceases the reduction in pipe pressure and flow is detected by the sensors of the accessory 2900 and the processor interprets this as a signal to close the valve 2910.

Next the localisation module 2004 performs sample amplification by using the piston to oscillate the sample flow in the sampling pipe in a manner described above. The sensors of the accessory 2900 and detect the oscillations in flow and/or pressure and the processor interprets this as a signal to keep the valve 2910 in the closed position while sample amplification occurs.

Upon detecting ceasing of the oscillation phase, the accessory 2900 interprets this as an instruction that the transportation phase has begun and opens its valve 2910 and activates its pusher fan 2908 to push the sample to the detector 11 for analysis.

The transportation phase is stopped upon the accessory 2900 sensing a change flow caused by the detector or localisation module. For example, the main aspirator of the detector 11 could be temporarily stopped, slowed or reversed, a valve closed, to cause a pressure change that signals the end of the transportation phase to the accessory 2900. In embodiments with a pusher fan 2908 such as this one, the transportation phase could be run for a predetermined time if running the pusher fan makes receiving a signal from the detector via the airflow path unreliable.

At the end of the transportation phase the accessory closes the valve 2910 and the system returns to normal detection operation.

FIG. 21 illustrates a further embodiment of an aspect of the present invention that leverages the existence of a pair of side by side pipe portions provided in embodiments like that of FIGS. 20A and 20B. The particle detection system 2100 is similar to the system of FIGS. 20 and 20A, however the positioning of the sample inlets along the pipe network 26 have been adjusted to aid the process of localisation. In this regard one of the difficulties in a practical implementation of the localisation techniques described herein is that of the ability to resolve neighbouring addresses, i.e. if the sample inlets join a sampling pipe too close together, it can be very difficult to detect when an air sample from one sampling inlet ends and an air sample from the next sample inlet begins. In the present embodiment, and that of FIGS. 22 and 23, the ability to resolve samples has been enhanced by arranging the position of the sampling inlets along the sampling points such that they are spaced out further than the minimum spacing. Turning now to FIG. 21 which illustrates a particle detection system 2100 including a particle detector 11, a localisation module 2004 and sampling pipe network 26. The sampling pipe network includes a sampling pipe 28 having a series of sampling inlets 29 spaced along its length. Similar to FIGS. 20A and 20A, the sampling pipe is a loop arrangement, or rather has two pipe portions following a similar path, e.g. two pipes 28A and 28B running parallel or generally in a side by side arrangement. However in contrast to the embodiment of FIGS. 20A and 20B the sampling inlets 29 in the system 2100 are spaced along both pipes portions 28A and 28B, thus the upstream pipe 28B is not provided to simply allow convenient connection of the upstream end of pipe particle portion 28A to the localisation module 2004. Instead, some of the sampling inlets 29 are positioned along the upstream pipe portion 28B and others on the downstream pipe portion 28A. This enables the spacing between sampling inlets to be increased by interleaving sampling points 29 positioned along the upstream pipe portion 28B with those positioned on the downstream pipe portion 28A as the sampling pipe 28 traverses neighbouring regions R1 to R8. As will be appreciated, in some embodiments the sampling pipe 28 extends through the regions R1 to R8 being monitored and the sampling inlets may be directly coupled to the sampling pipes or even be a hole directly formed in the pipe wall, however, a sampling pipe 28 does not need to actually pass through the regions R1 to R8 in order to service the region. In fact in many installations a sampling pipe will pass by the region but just outside it, e.g. above a ceiling panel of a room being monitored for particles, outside a housing of a series of cabinets being monitored or the like. These installations may use a length of pipe connected to the main sampling pipe which leads to a sampling point arrangement that is in fluid communication with the region being monitored.

In embodiments of this aspect of the present invention, the spacing of the sampling point arrangements of neighbouring regions is closer together than the distance between their points of connection to the sampling pipe network when measured along the flow path in the pipe.

FIGS. 22 and 23 illustrate additional implementations. FIG. 23 illustrates a system 2300 including a particle detector 11 connected to an air sampling network 26. The air sampling network includes a single run of three side-by-side, preferably parallel sampling pipe portions 2202, 2204, 2206. The downstream pipe portion 2202 is connected to the particle detector 11 on one end and to the next sampling pipe portion 2204 on its other end. The sampling pipe portion 2204 is also connected to the upstream sampling pipe portion 2206. The sampling points 29 are arranged such that each sampling point 29 connects to a different sampling pipe portion to its neighbours. That is, the sampling point servicing R1 connects to pipe portion 2202, whereas the sampling point servicing R2 connects to sampling pipe portion 2204, and the sampling point servicing R3 is connected to sampling pipe portion 2206. This pattern is repeated such that the sampling point servicing R4 connects to sampling pipe portion 2202 etc. In this way the distance between the sampling points 29, when measured along the length of the flow path of the sampling pipe is three times what it would be if a single run sampling pipe is used. The added separation between the points of connection makes resolving samples that are drawn from one sampling inlet from another more straightforward.

A further advantage that may be realised, in addition to the spreading out of the sampling points along the pipe network, arises from the (relative) re-ordering of the connection order to the pipe network, which it may increase reliability of localisation. In some cases the mixing or merging of samples in the sampling pipe network may mask (or falsely suggest) the presence of particles in physically neighbouring regions. By separating the points of connection of the air sampling points of one region, from that of its neighbours, in the sampling pipe network (most preferably by connecting a sampling point servicing at least one non-neighbouring region between them) the level independence of the air samples within the sampling system may be maintained to a higher degree.

Accordingly there is provided an air sampling system for a particle detection system for monitoring a plurality of regions, said regions being arranged such that at least one region physically neighbours another of the regions, wherein the air sampling system includes a sampling pipe network including a plurality of sample inlet arrangements, each of which services a respective region, and which is connected to the sampling pipe such that the sampling inlet arrangement of at least one region has a point of connection that is separated from the point of connection of a physically neighbouring region. Most preferably the point of connection of a sampling point arrangement of at least one non-neighbouring region is located between the points of connection of sampling inlet arrangements of the neighbouring regions. A particle detection system, including the air sampling system and at least one particle detector is also provided.

FIG. 23 illustrates another embodiment which implements this scheme. In this example the particle detector 11 is coupled to a localisation module 2004 and sampling pipe network 26. The sampling pipe network 26 includes a single sampling pipe 28 having four air sampling pipe portions 2302, 2304, 2306, 2308 connected to each other and co-extending past (or through) the regions R1 to R8. In this example, the far upstream end of the pipe 28 connects to the localisation module 2004 as described above. The downstream end of the pipe 28 connects to the detector 11, via the localisation module 2004. Localization can be performed using any of the methods described herein.

The sampling inlets of each region R1 to R8 are connected to the pipe segment 2302 to 2308 as follows:

| Region | R1 | R2 | R3 | R4 | R5 | R6 | R7 | R8 |
|---|---|---|---|---|---|---|---|---|
| Pipe segment | 2302 | 2304 | 2308 | 2306 | 2302 | 2306 | 2304 | 2308 |

Thus the regions are connected to the pipe network from downstream to upstream (i.e. the end nearest the detector to the end farthest from the detector) in the following order:
R1, R5, R7, R2, R4, R6, R8, R3

In this way no region has its air sampling arrangement 29 connected to the sampling pipe 28 next to a neighbouring region, and the points of connection are widely spaced along the pipe network.

In all other respects this embodiment can operate in accordance with the other schemes described herein.

The pipe portions may be individual lengths of pipe interconnected with fittings at their ends as will be known to those skilled in the art, or alternatively special purpose multi channel pipes can be used. The interconnections of pipe segments then takes place using interconnection fittings e.g. that may be attached over or into the ends of the channels of the pipe. The use of multi channel pipes can offer an installation advantage in that the installation technician need only handle a single element instead of multiple pipes.

Whilst the present example has been described with reference to a group of regions R1 to R8 that are arranged in a straight line, there is no reason that this need be the case. In reality the regions may be arranged in any geometry. Moreover there is no requirement that the regions need to be physically separated, e.g. as rooms are, but may be regions within one larger space or volume.

In order for the above techniques to work reliably in the field, it is necessary to calibrate or train the system e.g. to as to the volume of air moved before an air sample entering each sampling inlet arrives at the detector (or each detector), thus effectively characterising the system. Most preferably the system is trained while the air is being moved through the system in the same way as during the system's localisation mode. For example, if the system uses a pusher fan method, described below in connection with FIG. 15, a significant localisation error is likely to occur if the system is trained using normal detection operation when the pusher fan is not running. In one form, in which the system has a single air moving device, e.g. fan or the like or there is no mechanism to dramatically change the flow impedance or flow path through the detection system when changing from the detection mode to localisation mode, a relatively simple, but time consuming process can be implemented in training mode. In this case the system can be trained as follows. With the system operating normally, the system measures the volume of air moved starting from the time at which a test smoke e.g. smoke spray is dispensed, until the smoke arrives at the detector. This measurement is made for each sampling inlet. However this is can be time consuming as the training sequence needs to be performed for each inlet separately and the system may need to be left to return to normal operation between each cycle. Preferably the training mode uses a modified behaviour to reduce training time.

In other embodiments, e.g. a system which has an open valve plus a filter at end of the pipe during its transportation phase, the training mode involves opening the valve at the end of the pipe for a period of time. Smoke can then be selectively administered to each sample hole (or to multiple holes in selected patterns) so that the system will still suck smoke through the holes.

In training mode the system operates as follows:
 a. The system then opens valve at the end of the pipe.
 b. User then inputs to the detector when smoke is administered at a sampling inlet.
 c. The detector measures the volume of air moved starting from the indicated time until smoke is detected for each sample inlet.

In embodiments with a pusher fan (and preferably a valve and filter at the end of the pipe) it is more difficult to simulate smoke entering a sampling pipe. For example, it is not possible to get spray smoke into a sampling inlet with the pusher fan continuously running. Therefore an alternative method is needed. Such as:
a. Replicate the standard bellows operation, but with introduced smoke, including:
 i. Run the system normally;
 ii. Enter the calibration process;
 iii. Activate the bellows as if particles had been detected, and indicate to a user that this process has begun;
 iv. User applies spray smoke at the sampling inlet under test.

v. Deactivate the bellows and turn on the pusher fan to go into the transportation phase as normal, and record the volume of air transported before the smoke arrives at the detector.
vi. System indicates that the hole has been calibrated.
vii. System closes valve and turns off pusher fan.
viii. Other sample inlets are then calibrated in the same way.
b. A Special training mode:
i. System running normally.
ii. User puts the system into the test mode.
iii. The system continues to draw air in normally and the user applies spray smoke at hole and indicates this to the system.
iv. The system then immediately turns on pusher fan.
v. The system then records volume of air through flow sensor between indication of "spray start" and smoke being detected.
vi. The system then indicates that a sample inlet has been calibrated.
vii. System closes valve and turns off pusher fan.
viii. The next hole is then calibrated using the same process.
c. Special smoke injector.

This method is faster for the user but the user needs special equipment. This method involves use of an injection device which allows smoke to be sprayed into a sample inlet in a manner that other positive pressure in the pipe. One way of doing this involves use of a test smoke generator unit that seals around the sample inlet and sprays smoke into the inlet. For example the smoke generator can have an outlet that includes a foam gasket which clamps around the sample inlet so air is not coming out the sample hole. Once fitted and a sample is injected into the sampling inlet the user inputs to the system that this smoke was sprayed. The system records the volume of air moved before the smoke pulse arrives at the detector. FIG. 27 shows an example device. Although this device includes adaptations that can advantageously be used with video verification systems, this device may be used without these adaptations if needed.

Rather than empirically testing the behaviour of the system a simulator can be used. The simulator is similar to Aspire (from Xtralis Pty Ltd). The simulator works out the expected volumes per hole during the transportation phase based on the actual system hole dimensions and distances.

In the above testing methods a user can either interact with the detector directly to communicate inputs to it, e.g. to enter training mode, or indicate when test smoke has been sprayed etc. However in a preferred embodiment the detector system includes an interface, preferably wireless, by which the detector communicates with a user device, e.g. a portable computer, tablet computer, smart-phone or the like, and the user device runs an application that allows the detector to be controlled to operate as described.

In some particle detection systems, an enhancement can be provided by interfacing the particle detection system with a video security or surveillance system. Such systems use the images captured by the video security system either to perform additional particle detection methods (e.g. by performing video analytics to attempt to verify the detection of particles) or to allow a human operator of a monitoring station (CMS) to view an area in which particles have been detected so as to have human verification of the particle detection event. This may aid in determining threat level and determining an appropriate response to the detection event. An example system including a particle (in particular smoke) detector and video security system is illustrated in FIG. 24. Further details of such systems and their operation are described in the Applicant's co-pending PCT application filed on 7 Jun. 2013 and entitled Multi-Mode Detection.

FIG. 24 is a floor plan of a building 2400 including plurality of rooms. Each of the rooms is indicated as belonging to a zone which is monitored by a respective camera. In this regard, zone 1 is monitored by camera 2401; zone 2 by camera 2402; zone 3 by camera 2403; zone 4 by camera 2404; zone 5 by camera 2405; zone 6 by camera 2406; zone 7 by camera 2407; and zone n by camera 2408.

Each of the zones also includes a means for detecting particles 2410.1 to 2410.$n$. means for detecting particles 2410.1 to 2410.$n$ could be of any type, including point detectors, aspirated detectors, beam detectors, open area active video detectors. In the present example the means for detecting particles 2410.1 to 2410.$n$ is an air sampling inlet to an air sampling pipe 2413 that is connected to a particle detector 2411 thus forming a particle detection system of any one of the types described herein. The particle detection system is arranged to determine which sampling point 2410.1 to 2410.$n$ particles entered, as described herein and indicates a particle level or alarm level for each detector point 2410.1 to 2410.$n$. The particle detector 2411 connected to sampling points 2410.1 through 2410.$n$ and is connected to a building fire alarm system either in the form of an FACP or central controller 2412, and arranged to individually identify each sampling point as having an address on that system to enable the location of fire detection within the building 2400 to be indicated by the fire alarm system. Each of the cameras 2401 to 2408 are connected to a central control system 2412. The central control system 2412 is a video analytics system which receives and analyses video feeds from the multiple cameras. The central controller can also store and transmit video feeds to a central monitoring station either in real time or on demand as events are detected. The controller 2412 is connected via a communications channel to a central monitoring station (CMS) 2414, at which alarm situations, both fire related and security related, can be monitored. In alternative embodiments the functions of the controller 2412 and FACP can be combined into a single device. Also the functions of the central monitoring station 2414 could be performed at the controller 2412. Similarly the cameras and other security systems (not shown) and fire and/or smoke can connect directly to a remote CMS which performs all monitoring and analysis (i.e. the functions of the controller 2412 and FACP) directly.

Consider now a situation in which a fire starts in zone 2 of the building 2400 of FIG. 24. In this case, the sampling point 2410.2 located within the room will draw a sample air indicating the presence of smoke particles in plume 2413. Once an initial detection is made the detector 2411 will then perform localization as described above and send an alert signal to the fire alarm control panel (FACP) indicating the position of the suspected fire. As is conventional in such systems the output signal of the detector 2411 can indicate a level of particles detected or an alarm state determined according to alarm logic of the detector. The fire alarm control panel will communicate this alert data via central controller 2412 back to the central monitoring station 2414 where staff can monitor conditions in the building 240. Because the system includes video verification capabilities, upon detection of particles in zone 2 via inlet 2410.2, video verification using camera 2402 is activated. The camera 2402 begins either capturing (if it was not previously capturing images) images or analysing images to determine whether smoke can be verified to be present from the images. The video feed from the camera 2402 is provided to the central controller 2412. The central controller 2412 performs video analytics on a series of frames captured by camera 2402 to determine if there are visual features in the images which indicate either the presence of smoke or flame within the field of view 2402.1 of the camera 2402. This video analytics can be performed either in the controller 2412 or at the central monitoring station 2414. If the analysis is to be performed at the central monitoring station 2414 the video images, perhaps in a compressed form, will need to be transmitted from the site controller 2412 to the central monitoring station 2414 for analysis. Upon detection of smoke or fire in the images captured by camera 2402 the alert system running at the central monitoring station 2414, can modify its output to indicate that the alert condition indicated by the smoke detector 2410.2 is verified by the video analytics system. From this verification a user can infer that the chance of a false alarm is low.

By indicating to the user monitoring the central monitoring station 2414 that a fire or smoke alarm has been verified, the importance level of that alarm will be raised. Accordingly the person monitoring the system will be encouraged to act more quickly on the alert. FIGS. 25 and 26 show two alternative interfaces which can be provided for the central monitoring station according to embodiments of the present invention. Turning firstly to FIG. 25, the interface includes a plurality of video display panes 2501, 2502, 2503 and 2504 each of which displays images captured from different cameras within the building 2400 which is being monitored. The large viewing pane 2501 is provided in order to give a closer view of a location to the user of the monitoring system such that they can visually inspect a scene at which an alert has occurred. The smaller display panes 2502 through 2504 may cycle according to an appropriate scheme or alternatively be ranked in a priority order according to alert levels in the corresponding zones. The bottom portion of the interface 2500 includes a list of events 2507. For each event, event data is displayed and the user of the system is provided with a series 2509 of buttons for performing certain response actions. For each event the following data is displayed: an event number 2512 being a numerical listing of events, an "Event ID 2514 being a system-wide unique identifier for the event used for indexing logged event data for access at a later time; an event description 2516 explaining the nature of the event; an event level 2518 being a priority ranking for the event; an indicator of the status 2520 of the event e.g. whether it is an alarm or fault or other particular type of alert a series of action buttons 2522.1, 2522.2, 2522.3.

Event number 5 in the present example, has the highest alert status and will be described herein in more detail. Event number 5 is an indication that smoke has been detected in zone 2. The smoke in this example has been detected by particle detector 2410.2 at a level indicating that alarm should be raised. In the status column, the event is indicated as "alarm verified" because the video analytic system has analysed the output of camera 2402 and determined that smoke and fire is present. In order to indicate the verification to the user of the system, the interface has highlighted the status box corresponding to event number 5 and indicated in text form that the alarm is "verified". As will additionally be noted the image of zone 2 includes a visual indicator 2508 of the location of the smoke and fire detected by video analytics system. In this regard, the video analytic system has performed an analysis of a series of images captured by camera 2402 and has indicated a boundary or edge around a region within the image which is determined to represent smoke. Additionally, an indication of a zone within the image 2510 is indicated as appearing to represent flame which is causing the fire.

FIG. 26 shows an alternative interface to that of FIG. 25 the only difference between the interfaces of the two figures is that rather than simply indicating that the status of event number 5 has been "verified" the interface of FIG. 26 orders each of the events in the event list according to their alarm level and verification level. This additionally highlights that greater priority should be given to event number 5 compared to the other events within the system.

Once an event has been detected and verified by the automatic video verification system it will be up to a human user of the system to determine an action to be performed in response to the event. The person may choose to dismiss the event (2522.2) or view the video feed (button 2522.1) corresponding to the event to further investigate or to raise an external alarm (2522.3) by either calling Police, fire brigade or other appropriate emergency response services. This can be performed using the interfaces of FIGS. 25 and 26 using the buttons view (2522.1), dismiss (2522.2) or call (2522.3) as indicated.

In an additional embodiment of the present invention, it is advantageous that the video analytic system further assists the user in their investigation of pending events. In this regard, a user of the system may wish to investigate the cause of an alert, for example by determining where the event has originated, or what the true cause of an event is, for example what or thing is on fire or in danger of being set alight and is causing a smoke detection event. Such information can be particularly valuable in determining a response strategy to an alert condition. For example, if it is known exactly what is on fire an appropriate suppression strategy can be implemented. Moreover, anything surrounding the fire can be visually inspected to determine what level of response is needed. For example, if important equipment or hazardous or flammable items surround the area above the fire is, a faster response may be needed or total evacuation whereas if a fire is detected in a relatively open area or area in which non-flammable items are located a slower (or at least different) response may be acceptable.

In order to assist in the investigation process, the central monitoring station can be provided with software which analyses alarm outputs from one or more cameras and condition sensors and makes a recommendation to a user as to the order of recommended investigation as to the source or nature of the event. For example, the software system can store a map or other geographical data as to the relative position of rooms and items in the premises being monitored, and using data representing which sampling inlets have received particles, determine either a likely central point at which the fire has originated or an investigation priority. For example, in FIGS. 25 and 26 a verified alarm has been sensed in zone 2 and an unverified alarm has been sensed in zone 3. A pre-alarm has also been sensed in zone 1. In a situation in which verification of the presence of flame (indicated at 2510 in FIG. 25) is not possible, the central monitoring station will recommend an order of manual analysis of other zones in order of zone 2, then zone 3, followed by zone 1, followed by zone N. This is based on received alert levels of zones 2, 3 and 1 and the proximity of the doorways of zones 2, 3, N and 7, and the fact that zone 1 is a corridor between them. In other embodiments other factors can also play a role in determining investigation order, e.g. if the building's air conditioning return duct is located at position 2420 abnormal particle levels detector via points 2410.12 may be treated as lower priority other air sampling points as it will tend to indicate smoke more often than other air sampling points.

Thus should smoke be detected at in e.g. zone 2 and zone 1 at sampling point 2410.12 then zone 2 is likely to be the source of the fire. Conversely if only sampling points 2410.11 and 2410.12 are determined to have drawn a sample containing smoke, but no other sampling points, then zone 1 is the likely source of the fire condition.

It is also useful to note that without the video verification process applied to event 5 in FIG. 25 the alarm level of zones 2 and 3 would be otherwise identical. Without video verification there will be no additional information on which to base a decision that the fire is actually present in zone 2 and not zone 3 other than physical inspection. This clearly aids with the response strategy which because of the video verification process described herein enables a response to be targeted on zone 2 first which is where the fire is actually present.

The sensors (e.g. cameras) described in the illustrated may be fixed cameras or be capable of changing their field of view, e.g. be pan-tilt-zoom (PTZ) cameras. If a PTZ camera is used the camera can be programmed to pan, tilt, and zoom either to isolate locations that are identified as potentially causing an alert condition to enable investigation, Alternatively or additionally the PTZ camera can be controlled such that is captures images of a first view, and then moves to a second view and possibly one or more additional views successively, pausing for a specified time at each view. The sequence can be repeated indefinitely.

Video analysis can be performed on each view independently of the other views. In general terms this can be considered a process of performing time division multiplexing of images taken with the one camera at different PTZ settings, with each PTZ setting corresponding to a time slot. The video analytics can be performed on a series of images from successive instances of each PTZ time slot. Images captured in corresponding PTZ time slots can be treated as a "camera" and video analytics can be performed using the techniques described in earlier examples for a single camera.

Systems such as this add an extra dimension to the commissioning/calibration process described above, in that it is necessary to correlate the location of the air sampling inlets with their physical locations and also with the views of the cameras of the security system. In some cases it might even be desirable to correlate PTZ parameters of a particular cameras with a sampling point.

An apparatus and method for correlating an address in a particle detection system, said address corresponding to a physical location, with a location being monitored in a video capture system that monitors a plurality of locations will now be described in connection with FIG. 27. FIG. 27 illustrates an exemplary apparatus 2700 that can be used for conveniently commissioning, calibrating and/or testing particle detection systems. It could also be used in non-video enabled particle detection systems such as conventional Aspirating particle detections systems, as will be apparent from the following description.

The apparatus is arranged to provide a mechanism to perform smoke tests such that the location of the smoke can be learned by the smoke detector system and in the case of a system with video verification of alerts, the security system also in a simultaneous fashion. The apparatus enables the operator to inject smoke (or other test particle) at each sampling inlet of an air sampling particle detection system, point detector or other smoke sensing device, preferably in no particular sequence, and record e.g. on an integral computer device such as tablet computer or the like, the physical location of the inlet or sensing device. The data can be transferred to the particle detector either in real time or afterwards, so that the particle detector knows which inlet is mapped to which physical location. Preferably (but not essentially) the apparatus enables the security system to identify which particular camera (and optionally PTZ parameters) is associated with each inlet's address location. Association of the inlet or sensor location with a location in the video security may be achieved by visible means. As the smoke injection occurs, the visual indicator is activated, e.g. by flashing a code for a time. The security system searches for the visual indicator and identifies images of it amongst the images captured by its various cameras. The security system can then correlate the right camera and optionally PTZ position with location of the air sampling inlet or sensor. Thus the apparatus 2700 according to the preferred embodiment includes:

- a mechanism for delivering (and preferably generating) smoke to the a sampling inlet;
- means for enabling detection of the apparatus in an image captured by the video security system, and optionally means to communicate data over this optical means.
- means for synchronising the actions of the apparatus with the particle detection system and/or security system.

More particularly the exemplary device 2700 includes:

- A controller 2702 that controls operation of the device apparatus 2700.
- A power supply 2704, which will typically be a battery.
- A smoke generator 2706 to produce test smoke for introduction to the sampling points as needed.
- A fan 2710 to push the smoke to the point of delivery.
- A duct 2712 to guide the smoke generated by the smoke generator 2706 to the point of delivery. In this example the duct 2712 is an extendible, e.g. telescopic, pipe to enable convenient use with sampling points at different heights and convenient device storage. The duct 2712 terminates in an exit port 2714 that is shaped to enable easy coupling to or around a sampling point. In this example the exit port 2714 is a funnel shaped exit port, that can fit over or around a sampling point.
- A user interface 2716, which in this case includes one or more control buttons 2718 and a touch screen display 2720. These can be configured, in a manner know to those skilled in the art to control operation of the apparatus 2700 and enter data as will be described below.
- A synchronisation port 2722, which can be a wired or wireless communications means for establishing data communications with external devices, e.g. the smoke detection system, video security system or elements of these systems. In the case that the port 2722 is wireless, the port 2722 can be used for real-time communications. If the port 2722 is adapted for making a physical connection, communications could be made in real time (e.g. my being plugged into the other systems during use) or asynchronously (e.g. sharing stored data and/or synchronisation of the device with one or both of the smoke detection system and video security systems after use).
- A visual communications system 2724, which in this case includes an arrangement of radiation emitters 2724.1, 2724.2, 2724.3. The visual communications system can be used to communicate with the security system during use of the apparatus 2700, in a manner described below. The visual communications system 2724 may emit visible or invisible radiation, so long as it can be received and relayed to the video surveillance system.

Most preferably the radiation is received by the security system and captured in its video images of a region. In this way, the presence of the apparatus 2700 and (optionally data) is conveyed by the state of the visual communications system 2724.

An exemplary use of the test apparatus 2700 will now be described in connection with commissioning a particle detection system that has a video verification performed by a video security system. The objective of the apparatus 2700 is to assist and preferably automate the configuration and verification of the integration between smoke detection system and video security system. Specifically, the tool aids the smoke detection system and video security system to have the same sense of physical locations that is being protected.

Prior to the start of the training process, the particle detector system and video security system is set to a "training" mode.

At each sampling inlet of the particle detector system smoke is generated by the technician using the apparatus 2700. When triggered, the apparatus 2700 generates an amount of smoke sufficient to trigger the particle detection system to detect particles. The trigger to generate smoke will also switch on a visual indicator that is distinguishable from background entities in the images captured by the security system. While in the "training" mode the video security system analyses the imaged captured by it, and searches (either periodically or continuously) for the visual indicator 2724 in the images. Once found, it will record the apparatus's location (camera and PTZ presets if necessary) to identify which video camera will have the area surrounding the sampling hole in its field of view.

At the point of generating the smoke, the technician also records a name (and optionally a description) of the physical space e.g. using a keyboard interface on the touch screen display 2720. This text is stored along with the smoke test start and end time, and is optionally transmitted to the smoke detector and/or security system for correlating with detected events in these systems. During normal operation the text entered at this point can be presented to the CMS operator when the sampling hole is identified during actual use of the system.

The apparatus 2700 is configured e.g. programmed to guide the technician as to what action to take next, e.g. when move to a new sampling point, whether the technician needs to wait before triggering the smoke, the period that the technician needs to dwell with the smoke generator at the current hole, prompt for technician for name of the sampling hole etc.

Sampling points are typically located near the ceiling though there will be exceptions. The generated smoke needs to reach the sampling hole quickly and directly. However, it is strongly desirable that the technician always remain on the ground even when they trigger smoke to be presented in close proximity to a sample hole mounted high up in the ceiling, thus all controls are located at the bottom of duct 2712, and the duct 2712 is extensible.

The smoke generation start and end events for each sampling hole is synchronised with the particle detection system and video security system. This synchronisation can be done in real time over a wireless network. Optionally or alternatively the apparatus 2700 can provide the same capability without the real time use of wireless networks in an offline mode. For this later case, at the completion of the commissioning process the apparatus 2700 will need to be connected with the particle detection system and video security system to synchronise the recorded data including the name of the physical spaces. This could be performed via any communications medium or channel, including but not limited to, USB, Ethernet or WiFi.

In the example of FIG. 24 the following series of data are generated in the "training" mode by the test apparatus, smoke detection system and security system respectively.

TABLE 1

Test Apparatus data table

| Start time | End time | Physical location name | Co-ordinate (optional) |
|---|---|---|---|
| 1:00 | 1:01 | Main Corridor | −37.813621 144.961389 |
| 1:05 | 1:06 | Boardroom | −37.813637 144.961398 |
| 1:08 | 1.09 | Library | −37.813824 144.961398 |
| ... | ... | ... | ... |
| 1:30 | 1:31 | Cleaner's Cupboard | −37.813610 144.961372 |

TABLE 2

Smoke Detector table

| Start | End | Location parameter | Inlet number |
|---|---|---|---|
| 1:00 | 1:01 | 130 Liters | 5 |
| 1:05 | 1:06 | 125 Liters | 4 |
| 1:08 | 1.09 | 100 Liters | 2 |
| ... | ... | ... | ... |
| 1:30 | 1:31 | 16 Liters | 1 |

TABLE 3

Security System table

| Start | End | Camera | PT2 |
|---|---|---|---|
| 1:00 | 1:01 | 2401 | P = 5 T = 20 Z = 200 mm |
| 1:05 | 1:06 | 2403 | — |
| 1:08 | 1.09 | 3402 | — |
| ... | ... | ... | ... |
| 1:30 | 1:31 | 2405 | — |

Once the training data has been recorded by the test apparatus 2700, smoke detector system and security system, this data needs to be correlated in order for the video verification system and smoke detection systems to work together in the event of an actual smoke detection event. As can be seen the start and end times in each table can be used to correlate smoke test data with the smoke detector data and security system data.

In use, in the event that smoke is detected by the smoke detection system it will determine where in its system smoke was detected. If the system includes one or more point detectors "addressing" i.e. determining where the event was detected is relatively straightforward and only requires knowledge of which detector has detected smoke. If the system includes or is an aspirated particle detection system with an air sampling network the system can performs one of the localisation methods in any one of the following Australian patent applications 2012904516, 2012904854 or 2013200353 filed by the applicant or other localisation technique to identify the location of the source of the particles. The output could be a location, name (e.g. the name given by the technician during commissioning) room address or a smoke localization parameter (such as a volume of air sample that has passed through the detector between detection events whilst in the localisation phase, which identifies which of the sampling holes the smoke entered the smoke detection system through, using any of the methods described herein. This output is passed to the security system. On the basis of this name, identifier or localization parameter the security system is able to determine which of its cameras provide a view of the determined air sampling point.

In this case, the security system will identify camera 2405 as the camera which will show a view of the region in which the smoke detection event has taken place.

As will be appreciated, additional information could be gathered during commissioning to aid the CMS operator in determining an appropriate action when smoke or a fire is detected.

Additional features can also be included in some embodiments of the apparatus 2700. For example, in some embodiments other methods can be used to determine the location of the apparatus 2700 to assist or automate identification of the location and sampling inlet. For example satellite positioning (e.g. GPS or DGPS) or triangulation from electromagnetic emitters, could be used to determine which room the apparatus is in, thereby obviating or minimising the need to enter data into the system. The sampling point may be provided with a short range communications mechanism, e.g. an RFID tag, that is read by a reader mounted near the end of the duct 2712 to identify which sampling point is being commissioned in each step. This communication could also be used as the trigger for beginning the test procedure for the sampling point.

FIG. 17 illustrates a variant of the system of FIGS. 14A to 14E. The system 1700 is identical in all respects to the system of FIGS. 14A to 14E and operates in the same manner, with the exception that the sample amplification arrangement 1702 is located at the upstream end of the sampling pipe 28. This simplifies the detector end of the sampling network 26 and facilitates retrofitting of a sample amplification arrangement 1702 to a legacy detection system that was originally installed without such a capability.

FIG. 18 illustrates a particle detection system including an air sampling network that has a sample amplification arrangement comprising a plurality vibrating membranes. Essentially this system 1800 is a double ended version of the systems of FIG. 14A to 14E and FIG. 17. In this embodiment the two pistons 1802, 1804 (formed from the vibrating membranes of loudspeakers) act together to form the sample amplification arrangement. These can be operated in concert as described in connection with opposing fans of FIG. 15. However, being loudspeakers (or other similar air movement device capable of causing rapidly oscillating air flow) these pistons 1802, 1804 offer new the ability to selectively perform sample amplification at one or more sample inlets 29 along the sampling pipe 28. This can be achieved by oscillating the pistons with a selected phase difference between them. This causes selective reinforcement or cancellation of the sample amplification action at different places along the sampling pipe 28.

FIG. 19 illustrates another particle detection system including an air sampling network with branched sampling pipes and which has a sample amplification arrangement comprising a plurality vibrating membranes. The system 1900 includes a particle detector 11, coupled to an air sampling system 26. The air sampling system 26 is branched such that it has sampling pipes 28A and 28B each of which includes a plurality of sample inlets 29A and 29B arranged in series along their length. At the upstream ends of the pipes 28A and 28B are located pistons 1902, 1904. A common piston 1906 is placed at the downstream end of the sampling network 26. The sample amplification arrangement comprising the pistons 1902, 1904, 1906 can be operated to selectively cancel its oscillation effect by choosing appropriate phase differences between oscillation of the pistons in the sample amplification phase. For example in the example the downstream piston 1906 is operated in phase with the upstream piston 1902 on the pipe 28A, but out in anti-phase to the upstream piston 1904 on the pipe 28B. The result is that sample amplification occurs only on the sample inlets 29A but not on inlets 29B.

This process can be extended and combined with the method described in connection with FIG. 18. In this regard, greater selectivity can be achieved by operating the downstream piston 1906 is with a selected phase difference to the with the upstream piston 1902 on the pipe 28A, and no oscillation of piston 1904. Most preferably, if a node in the oscillation pattern coincides with the junction between the pipes 28A and 28B sample amplification will be minimised (or possibly eliminated) on pipe 28B and selective sample amplification can be achieved along the length of pipe 28A.

As will be appreciated the double-ended sample oscillation techniques described in connection with FIGS. 18 and 19 could also be implemented with other types of air flow movement devices, e.g. bellows, fans (as illustrated in FIG. 15) or the like.

The systems of FIGS. 17 to 19 could be implemented such that the localisation hardware is provided in a detector-end module, such as module 2004, described above. As will be appreciated this may necessitate the use of a return pipe segment to enable location of the upstream components (e.g. pistons 1702, 1804, 1902) physically near to the downstream end of the pipe 28 so that they can be housed together in the module.

Although a purge step is only described in connection with the example of FIG. 15B, it should be appreciated that a purge phase may optionally be used in all embodiments described herein to improve accuracy of localisation. A purge step, generally speaking involves filling the air sampling network with clean air (or at least air that is distinguishable from sample air), which will typically necessitate means for providing said air, e.g. a filter arrangement that is selectively insertable into the system to enable delivery of clean air. Therefore, where applicable such means can be provided in the systems described herein.

As will be appreciated from the foregoing, a number of techniques have been described within this document to improve addressing in aspirated particle detection systems which include centralised detector and a plurality of sample inlets placed along a duct or pipe of an air sampling system. It will be apparent to those skilled in the art that elements of each of the systems could be combined to further enhance system performance. To give but one example, the pipe network work system of FIG. 14, 15 or 16 could be used to increase smoke concentrations within the pipe network to deliver a clearer smoke concentration front to the detector for use in the cross-correlation method described in connection with FIGS. 5 and 6. Moreover, instead of using time based correlation, volume based correlation could be used as described above. Other combinations will be readily apparent to those skilled in the art.

It will be appreciated that the present invention, although described in relation to the detection of smoke, can equally be applied to any other material that can be usefully detected by a sampling system, including gases, dust, vapour, or biological materials.

FIG. 30 illustrates a further embodiment of a localisation module 3000 that can be used as a localisation module 2004 in any one of the embodiments illustrated herein. The localisation module 3000 contains the following main elements:

A main flow path 3002 that extends from the sampling pipe 28 at one end (the inlet 3004 to the localisation module 3000) to the detector 11 at the other end (the outlet 3006 from the localisation module 3000). The main flow path 3002 includes an additional particle detector 3010. The particle detector 3010 may be a particle detection chamber that is either the same or different to the main particle detection chamber 14, or of a different type. In a preferred form the secondary particle detector provides a faster response to particles than the main detection chamber 14, although this is not necessary in all embodiments. The main flow path 3002 also includes a valve (3012) that can be used to close off the main flow path 3002 and divert all flow into a primary branch flow path 3014, described below in more detail.

The primary branch flow path 3014 includes a first branch 3016 leading to a sample amplification device 3018. In a preferred form the sample amplification device 3018 takes the form of a reciprocating piston that can be used to rapidly switch between pushing and pulling a small amount of air within the sampling pipe. The primary branch flow path 3014 includes a second valve (3020) that can be used to block access to the piston and divert flow from the primary branch flow path 3014 into a secondary branch flow path (3022).

The secondary branch flow path 3022 contains a fan 3024 and a filter 3026 that are arranged to enable air to be drawn into the secondary branch flow path 3022 from outside the system, filter the air, and pass it to the additional particle detector 3010 in a manner described below.

FIG. 31 illustrates a localisation module 2004 that has been extended to operate with an air sampling network 26 having multiple air sampling pipes 28.2, 28.2. The localisation module 2004 could be extended to handle multiple sampling pipes by duplicating the components described above. However, in order to reduce parts count and/or cost of goods certain components may be shared. In this embodiment independent main flow paths 3002.1 and 3002.2 are provided. In this case the valves (3012.1 and 3012.2) are operated together and connected to respective branches of the primary branch flow path and operated in concert with each other. In most multi-pipe systems e.g. Vesda Laser Scanner or Vesda Laser industrial (both sold by Xtralis Pty Ltd) the main particle detector still only has one detection chamber and the air samples from each of the pipes are mixed together in a manifold prior to analysis in the detection chamber.

In all other respects the multipipe localisation module is the same as that of FIG. 30 and matching reference numerals have been used. As will be appreciated a multipipe localisation module can be made to handle any number of sampling pipes required.

FIGS. 32 and 33 illustrate two additional embodiments of the accessory 2800. The accessories 2800 may be used as pipe end-caps that are mounted at the far upstream end of a sampling pipe 28. However, they may also be placed at other points in the sampling network e.g. at the upstream end of a branch pipe or off a T junction at an intermediate point in a sampling pipe, such that selective opening of the accessory flow path allows air into the sampling pipe The embodiment of FIG. 32 has a fan 3202 and a valve 3204 (equivalent of valve 2808 of FIG. 28) that can be activated under control of the localisation module. In normal smoke detection operation the valve 3204 is closed and the fan 3202 does not run. When activated, the valve 3204 is opened and the fan 3202 is activated so that air is drawn into the end of the pipe 28 and blown down the sampling pipe towards the detector 11. The accessory 2800 can also optionally include a filter, such as a HEPA filter so that the air entering the pipe is better able to be distinguished from sample air drawn into the system from sampling points.

The accessory 2800 of FIG. 33 is very similar to the embodiment of FIG. 28 and like features have been like numbered. The accessory includes a valve 2808 that can selectively open the pipe, but no fan. It also includes a filter 3302. The valve 2808 is actuated by the controller 2806 upon sensing low pressure or back-flow in the sampling pipe 28. When a high negative pressure is detected, the end cap is opened to allow air to be drawn into the end of the pipe.

In use in a preferred embodiment the particle detection system using a localisation module of the type illustrated in either of FIGS. 30 and 31 and an accessory illustrated in either of FIG. 32 or 33 will have the same general architecture as that show in other embodiments such as FIG. 29, with a main particle detector, localisation module 2004, sampling network 26 with sampling pipes 28 and at least one accessory mounted upstream of the localisation module. Operation of such a system will now be described assuming use of the accessory of FIG. 32.

In overview, the detector 11 operates in a normal particle mode drawing air samples and analysing them continuously. However once particles are detected above a trace level the system does into a localisation mode and activates the localisation module 2004. The main detector 11 is then de-activated and air samples cease to be drawn through the main detector 11. The localisation module 2004 then performs a sample amplification routine as described above. As noted above "amplification" mixes the air in the pipe with the local atmosphere surrounding each sample hole and causes packets of air in the sampling pipe adjacent each sampling hole to form—these packets have a composition similar to the atmosphere immediately surrounding the sampling point. As will be apparent from the foregoing description, in normal steady state operation the air sample drawn in through each sampling hole is diluted by the air drawn into all other sampling holes as it passes through the sampling network 26. However, in this embodiment, because the amplification only sucks and blows a small amount of air back and forth through the system the packets are not diluted in this way.

The contents of the sampling pipe with "packets" is then drawn back to the additional particle detector 3010 for analysis by re-activating the main fan of the main detector and, if an accessory with a fan is used (e.g. that of FIG. 32) by pushing it with the accessory's fan. During this "transportation" process the volume (or a related value) is measured. When the additional particle detector 3010 detects a packet of smoke, the drawn volume is read off and compared to a look-up table to determine which sampling hole corresponds to the smoke packet that was detected.

The secondary branch flow path does not play any part in this localisation process. However, it is only used to flood the additional particle detector 3010 with clean air for calibration. This process happens periodically, say once a day.

In tabular form the process can be viewed as follows:
Normal Operation

| Main aspirator | Main Detection chamber | Flow sensor | Valve 3012 | Valve 3020 | Sample Amplifier | Additional particle detector 3010 | Fan in branch 3024 | Volume or volume-related measure) | Valve 3204 | End cap fan 3202 (if present) |
|---|---|---|---|---|---|---|---|---|---|---|
| On | On | Active | Open | Closed | Inactive | Inactive | Off | Inactive | closed | Off |

Where for Valve 3012
  Open=main flow path open and primary branch flow path blocked
  Closed=main flow path blocked and primary branch flow path open for Valve 3020
  Open=primary branch flow path open so sampling pipe open to amplifier
  Closed=secondary branch flow path open so sampling pipe open to fan and filter If trace level smoke detected by the main detection chamber then normal detection is ceased and an amplification mode is entered.

Amplification

In this state the localisation module 2004 enters its amplification mode and in this example the sample amplification device, e.g. piston 3018, repeatedly draws and pushes air to perform sample amplification. The volume of air moved in this process is low compared to the total volume of air in the air sampling system and is preferably less than half the volume of the sampling pipe between neighbouring sampling inlets.

the sampling pipe e.g. by opening valve 3204 (and if present) activating the pusher fan 3202. Opening the pipe's 28 end and blowing into the pipe's end causes a positive pressure in at least part of the pipe (the portion closest to the fan 3202) and minimises negative pressure (reduces suction) closer to the main aspirator of the system. This minimises the suction at the sampling inlets of the sampling pipe and consequently minimises the drawing of additional air into the sampling inlets during transportation, thus minimising dilution of the sample packets as they are sent to the particle detector for analysis.

Drawback is also preferably done at high enough speed to ensure turbulent flow in the sampling pipe, which minimises smearing out of packets along the pipe (as described elsewhere herein). A further advantage of high speed drawback during transportation is that it reduces transport time of packets from the far end of the sampling pipe 28 to the detector(s) enabling quicker response

| Main aspirator | Main Detection chamber | Flow sensor | Valve 3012 | Valve 3020 | Sample Amplifier 3018 | Additional particle detector 3010 | Fan in branch 3024 | Volume or volume-related measure) | Valve 3204 | End cap fan 3202 (if present) |
|---|---|---|---|---|---|---|---|---|---|---|
| Off | Off | inactive | closed | Closed | Oscillating | Inactive | Off | Inactive | Closed | Off |

After some predetermined time or number of oscillations, amplification is ceased and the system moves into Transportation mode.

| Main aspirator | Main Detection chamber | Flow sensor | Valve 3012 | Valve 3020 | Sample Amplifier 3018 | Additional particle detector 3010 | Fan in branch 3024 | Volume or volume-related measure) | Valve 3204 | End cap fan 3202 (if present) |
|---|---|---|---|---|---|---|---|---|---|---|
| On | Off or on | Active | open | Closed | inactive | Active | Off | Active | open | On |

Transportation

In this mode the system moves the amplified sample packets back to the additional particle detector 3010 for analysis. The volume of sample air that has passed through the system since transportation started, or a volume related value is measured, e.g. by integrating flow rate. This value is correlated with detection events in the additional particle detector 3010 to determine entry point of smoke.

As noted elsewhere herein transportation is preferably done at high speed. This is aided by opening a large port into After drawback is complete, the system goes back into normal operation.

The process can be cycled so as to update localisation data periodically, and also monitor smoke development.

Use of the Secondary Branch Flow Path 3022

As will be appreciated from the above description the secondary branch flow path 3022 plays no role in normal detection, amplification or transportation phase. The main use of the secondary branch flow path is to provide a source of clean air that can be used to calibrate or zero either one or both the main detection chamber 14 or additional particle detector 3010 either periodically or when needed. This is performed by going into a zeroing mode in which filtered air is blown back through the secondary branch flow path into the main flow path until at least the additional particle detector 3010 is full of clean, filtered air. In the zeroing phase the system configuration is as follows:

| Main aspirator | Main Detection chamber | Flow sensor | Valve 3012 | Valve 3020 | Sample Amplifier 3018 | Additional particle detector 3010 | Fan in branch 3024 | Volume or volume-related measure) | Valve 3204 | End cap fan 3202 (if present) |
|---|---|---|---|---|---|---|---|---|---|---|
| Off | Off | Inactive | Closed | open | inactive | Active | On | inactive | closed | Off |

It is only necessary to blow enough clean air into the localisation module 2004 to fill the additional particle detector 3010. This can be done, for example, by running the fan 3024 for some pre-set time that is sufficient to blow as acceptable volume of clean air into the system. Alternatively clean air could be blown back into the additional particle detector 3010 until a relatively steady minimum particle reading is detected by the additional particle detector 3010.

In a further embodiment there is provided a method in a particle detection system having a particle detector in fluid communication with an air sampling network including at least one air sampling pipe and a plurality of air sampling points. The method generally involves, filling at least one air sampling pipe which has a plurality of air sampling inlets with a calibration substance (e.g. test smoke, or other substance detectable by the particle detector such as FM200 or the like) that is able to be detected by the particle detection system, said air sampling pipe being filled with said substance at a level detectable by the particle detection system. Next the method involves drawing an air sample into the sampling pipe to cause localised dilution of the substance around at least one air sampling inlet. Preferably the dilution process involves changing flow direction in the sampling pipe. Most preferably the dilution process is similar to sample amplification as described elsewhere herein. The contents of the sampling system are then moved to the detector whilst detecting the level of calibration substance in the contents of the air sampling system, whilst also monitoring a quantity that can be correlated with the movement of the contents of the sampling system (e.g. volume, a volume related value, or time (although this is not preferred). Detecting said localised dilution in the substance in the contents of the sampling pipe and correlating said detection with the monitored quantity, to determine a value of said quantity corresponding to a sampling hole that caused the localised dilution. Detecting said localised dilution in the substance in the contents of the sampling pipe comprises detecting a reduction in particle level by a particle detector of the system.

The present method can form part of a commissioning process and in essence is the converse of the typical localisation technique, insofar as instead of amplifying a sample to create packets of sample, the substance-laden (e.g. smoke filled) sampling pipe has diluted packets created within it by the "amplification" process. Since the whole pipe can be flooded with the calibration substance simultaneously and multiple, and physically separated dilution packets created simultaneously, calibration can be performed of a greater number of sampling holes at the same time.

In order to implement such a system a method, filling of the sampling pipe can be manual via a sampling inlet or more preferably the sampling network can be fitted with an inlet such as a spigot (e.g. as part of the accessory 2800 or localisation module 2004). The latter is probably more convenient since in multi-pipe embodiments all pipes can be calibrated at once. The inlet is in fluid communication with a supply of calibration substance that has an approximately regulated output. The source of calibration substance can be connected to the inlet temporarily during calibration or permanently and enable periodic calibration and self test.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method of determining a point of entry of smoke into a smoke detection system, the system having a sampling pipe network including at least one sampling pipe and a plurality of sampling inlets through which an air sample can enter the at least one sampling pipe of the smoke detection system for analysis by a particle detector, said method including:
   detecting smoke in an air sample drawn via the sampling pipe network to a particle detector connected to the sampling pipe network;
   triggering a localization process in response to the detection of smoke to determine said point of entry of the smoke into the sampling network, the localization process including:
   changing an air sample flow characteristic in the smoke detection system;
   determining a volume of sample air that has passed through at least part of the smoke detection system after a change in the air sample flow characteristic or a value corresponding to said volume;
   detecting smoke in the air sample from which the volume or value is determined; and
   determining through which sampling inlet of the plurality of sampling inlets the smoke entered the smoke detection system based, at least in part, on the determined volume or value;
   wherein the localisation process includes opening said at least one sampling pipe at a position upstream of its respective at least one sampling inlet of the plurality of sampling inlets to provide a flow impedance that is lower than a flow impedance provided by any one sampling inlet.

2. The method according to claim 1, which includes continuously determining a flow rate of the air sample passing through at least part of smoke detection system.

3. The method according to claim 1, wherein the method includes commencing determination of the volume or value of sample air upon the occurrence of a predetermined event.

4. The method according to claim 1, wherein the volume of the air sample that has passed through at least part of smoke detection network is determined by accumulating a flow rate measurement over time.

5. The method according to claim 4, wherein the rate of flow measurement is a volumetric flow rate measurement.

6. The method according to claim 5, wherein the flow rate measurement is determined using an ultrasonic flow sensor.

7. A method according to claim 1, which further includes collecting all or a proportion of the sample air that has passed through at least part of the smoke detection system since the predetermined event.

8. The method according to claim 1, wherein the step of changing an air sample flow characteristic in the smoke detection system includes at least one of the following:
   opening a valve;
   closing a valve;
   changing a direction of an air sample flow in at least part of the smoke detection system;
   changing a rate of air sample flow in at least part of the smoke detection system;
   starting an aspiration system; and
   stopping an aspiration system.

9. The method according to claim 3, wherein the predetermined event comprises at least one of:
   the detection of smoke in an air sample drawn via the sampling pipe network to a particle detector connected to the sampling pipe network which triggers the localization process; and
   the change in the air sample flow characteristic in the smoke detection system.

10. The method of claim 1, wherein the localisation process includes moving the air sample to a particle detector, wherein said moving of include a low-dilution transportation phase of motion in which drawing of air into the plurality of sampling inlets is reduced.

11. The method of claim 10, wherein the low-dilution transportation phase includes any one or more of the following:
   closing one or more of the plurality of sampling inlets; and
   blowing the air sample along the duct from an upstream position thereof.

12. The method of claim 1, further including a purge phase of operation in which the air sample is purged from the sampling pipe.

13. The method of claim 12, wherein purge air to purge the air sample is introduced, via the opening in said at least one sampling pipe, at a position upstream of one or more of the plurality of sample inlets.

14. The method of claim 13, further including filtering the purge air introduced to purge at least one sampling pipe.

15. An apparatus for determining at least one point of entry of smoke into a smoke detection system of the type having a particle detector in fluid communication with an air sampling network, the air sampling network having at least one sampling pipe and a plurality of sampling inlets through which an air sample can enter the at least one sampling pipe of the smoke detection system for analysis by the particle detector, and an aspirator for drawing the air sample through the air sampling network to the detector, the apparatus including:
   an input configured to receive an indication of a detection of a smoke by the particle detector;
   a flow modifying mechanism configured to change an air sample flow characteristic in the smoke detection system in response to a first indication of the detection of smoke by the particle detector;
   means for determining a volume of sample air that has passed through at least part of the smoke detection system after the changing of the sample flow characteristic in the smoke detection system and until a second indication of a detection of a smoke by the particle detector is received or a value corresponding to said volume;
   at least one accessory configured to open said at least one sampling pipe at a position upstream of its respective at least one sampling inlet of the plurality of sampling inlets to provide a flow impedance that is lower than a flow impedance provided by any one sampling inlet; and
   means for identifying at least one point of entry of particles into the sampling network based on the detected volume or value.

16. The apparatus according to claim 15, wherein the apparatus identifies one or more of said points of entry by reference to one or more corresponding sampling inlets through which smoke determined to have entered the system.

17. The apparatus according to claim 15, wherein the means for determining a volume of sample that has passed through at least part of the particle detection system includes a volumetric flow sensor.

18. The apparatus according to claim 17, wherein the flow sensor comprises an ultrasonic flow sensor.

19. The apparatus of claim 15, wherein the at least one accessory includes one or more of the following:
   a valve;
   a fan;
   a flow control device; and
   a filter.

20. A smoke detector including;
   a particle detection chamber to detect particles in an air sample;
   an inlet to receive an air sample from an air sampling network, the air sampling network having at least one sampling pipe and a plurality of sampling inlets through which a sample can enter the at least one sampling pipe for analysis by the particle detection chamber;
   an aspirator for drawing the sample through the air sampling network to the detector;
   a flow modification system arranged to change an air sample flow characteristic in the air sampling network connected to the inlet; and
   a processor configured to determine a point of entry of the smoke into the sampling pipe network in response to a smoke detection event, by:
   causing the flow modification system to change an air sample flow characteristic in the air sampling network;
   determining a volume of sample air that has passed through at least part of the smoke detection system after the change in the air sample flow characteristic;
   determining a second smoke detection event in the air sample subject to the determination of the volume or a value corresponding to said volume; and
   identifying at least one point of entry of smoke into the air sampling network based, at least in part, on the volume or value;
   wherein the processor is further configured to cause an accessory to open said at least one sampling pipe at a position upstream of its respective sampling inlet or sampling inlets of the plurality of sampling inlets to provide a flow impedance that is lower than a flow impedance provided by any one sampling inlet.

21. The smoke detector as claimed in claim 20, wherein the smoke detector includes a flow sensor configured to detect a rate of flow of sample air passing through at least a part of the smoke detector.

22. The smoke detector as claimed in claim 21, wherein the smoke detector includes an ultrasonic flow sensor.

23. The smoke detector of claim 20, wherein the processor is further configured to cause the air sampling network to enter a low-dilution transportation phase of operation in which the drawing of air into the plurality of sampling inlets is reduced.

24. The smoke detector of claim 20, wherein the process is further configured to cause the air sampling network to enter a purge phase in which air to purge the air sample from the sampling pipe network is introduced, via said opening in said at least one sampling pipe, at a position upstream of the one or more sampling inlets of the plurality of sampling inlets.

* * * * *